United States Patent
Esfandyarpour et al.

(10) Patent No.: US 11,015,219 B2
(45) Date of Patent: May 25, 2021

(54) SYSTEMS AND METHODS FOR DETECTION AND ANALYSIS OF BIOLOGICAL SPECIES

(71) Applicant: GenapSys, Inc., Redwood City, CA (US)

(72) Inventors: Hesaam Esfandyarpour, Redwood City, CA (US); Max Greenfeld, Palo Alto, CA (US); Meysam R. Barmi, Menlo Park, CA (US); Kosar B. Parizi, Redwood City, CA (US); Hamid Rategh, Cupertino, CA (US); Amirhossein Samakar, Fremont, CA (US)

(73) Assignee: GENAPSYS, INC., Redwood City, CA (US)

(*) Notice: Subject to any disclaimer, the term of this patent is extended or adjusted under 35 U.S.C. 154(b) by 0 days.

(21) Appl. No.: 15/662,692

(22) Filed: Jul. 28, 2017

(65) Prior Publication Data

US 2018/0119215 A1  May 3, 2018

Related U.S. Application Data

(63) Continuation of application No. PCT/US2016/016813, filed on Feb. 5, 2016.

(60) Provisional application No. 62/113,283, filed on Feb. 6, 2015, provisional application No. 62/119,083, filed on Feb. 20, 2015.

(51) Int. Cl.
| | |
|---|---|
| *C12Q 1/6869* | (2018.01) |
| *C12Q 1/68* | (2018.01) |
| *C12Q 1/6825* | (2018.01) |
| *G01N 33/543* | (2006.01) |
| *G16B 20/00* | (2019.01) |
| *G16C 99/00* | (2019.01) |
| *G01N 27/07* | (2006.01) |
| *G01N 27/22* | (2006.01) |

(52) U.S. Cl.
CPC ............ *C12Q 1/6869* (2013.01); *C12Q 1/68* (2013.01); *C12Q 1/6825* (2013.01); *G01N 27/07* (2013.01); *G01N 27/226* (2013.01); *G01N 33/5438* (2013.01); *G16B 20/00* (2019.02); *G16C 99/00* (2019.02)

(58) Field of Classification Search
CPC ...... C12Q 1/6869; C12Q 1/68; C12Q 1/6825; G01N 33/5438
See application file for complete search history.

(56) References Cited

U.S. PATENT DOCUMENTS

| | | |
|---|---|---|
| 9,399,217 B2 | 7/2016 | Oldham et al. |
| 2011/0224914 A1 | 9/2011 | Messing |
| 2013/0034800 A1 | 2/2013 | Pavlik et al. |
| 2014/0329246 A1 | 11/2014 | Rigatti et al. |

FOREIGN PATENT DOCUMENTS

| | | | |
|---|---|---|---|
| CN | 104105797 A | 10/2014 | |
| CN | 104145026 A | 11/2014 | |
| EP | 2711415 A2 | 3/2014 | |
| GB | 2496932 A | 5/2013 | |
| WO | WO-2012047889 A2 | 4/2012 | |
| WO | WO-2012076350 A1 * | 6/2012 | ........... C12Q 1/6825 |
| WO | WO-2012166742 A2 | 12/2012 | |
| WO | WO-2013082619 A1 * | 6/2013 | ......... G01N 27/3278 |
| WO | WO-2013184416 A2 * | 12/2013 | ............ G01R 35/00 |
| WO | WO-2014152625 A1 | 9/2014 | |
| WO | WO-2015089238 A1 | 6/2015 | |
| WO | WO-2015138696 A1 | 9/2015 | |
| WO | WO-2015161054 A2 | 10/2015 | |
| WO | WO-2016127077 A2 | 8/2016 | |

OTHER PUBLICATIONS

Betz et al. KlenTaq polymerase replicates unnatural base pairs by inducing a Watson-Crick geometry. Nat Chem Biol 8:612-614 (2012).
International Search Report and Written Opinion dated Jul. 29, 2016 for International PCT Application No. PCT/US16/16813.
Liu, et al. Immobilization of DNA onto poly(dimethylsiloxane) surfaces and application to a microelectrochemical enzyme-amplified DNA hybridization assay. Langmuir. Jul. 6, 2004;20(14):5905-10.
EP16747351.1 Extended Search Report dated Jun. 18, 2018.
Polonschii et al. Multi Frequency, Multi Channel, Differential Impedance Analyzer for Rapid Assays. IFMBE Proceedings—13th International Conference on Electrical Bioimpedance and the 8th Conference on Electrical Impedance Tomography 2007 vol. 17, pp. 229-231 (2007).

* cited by examiner

*Primary Examiner* — Angela M. Bertagna
(74) *Attorney, Agent, or Firm* — Wilson Sonsini Goodrich & Rosati

(57) ABSTRACT

Provided herein are systems and methods for sequencing, amplifying, detecting, analyzing, and/or performing sample preparation procedures for nucleic acids and other biomolecules.

18 Claims, 41 Drawing Sheets
Specification includes a Sequence Listing.

```
                        SEQUENCE LISTING

<160> NUMBER OF SEQ ID NOS: 6

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
attatataag ctagctcggc cgcgatataa tt                                32

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ttaatattag ctcgatcgcc gcgc                                         24

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tagctcgatc g                                                       11

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tttttataag ctagctcggc cgcgatataa tt                                32

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tttatataag ctagctcggc cgcgatataa tt                                32
```

```
-continued

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttaatataag ctagctcggc cgcgatataa tt                                   32
```

SYSTEMS AND METHODS FOR DETECTION AND ANALYSIS OF BIOLOGICAL SPECIES

CROSS-REFERENCE

This application is a continuation of PCT Application No. PCT/US2016/016813, filed Feb. 5, 2016, which claims the benefit of U.S. Provisional Patent Application No. 62/113,283, filed Feb. 6, 2015 and U.S. Provisional Patent Application No. 62/119,083, filed Feb. 20, 2015, each of which applications is incorporated herein by reference in its entirety and for all purposes.

SEQUENCE LISTING

The instant application contains a Sequence Listing which has been submitted electronically in ASCII format and is hereby incorporated by reference in its entirety. Said ASCII copy, created on Apr. 18, 2019, is named 42808_735_301.txt and is 1,789 bytes in size.

BACKGROUND

The goal to elucidate the entire human genome has created interest in technologies for rapid nucleic acid (e.g., DNA) sequencing, both for small and large scale applications. Important parameters are sequencing speed, sequencing accuracy, length of sequence that can be read during a single sequencing run, and amount of nucleic acid template required to generate sequencing information. Large scale genome projects are currently too expensive to realistically be carried out for a large number of subjects (e.g., patients). Furthermore, as knowledge of the genetic basis for human diseases increases, there will be an ever-increasing need for accurate, high-throughput DNA sequencing that is affordable for clinical applications. Practical methods for determining the base pair sequences of single molecules of nucleic acids, preferably with high speed, high accuracy and long read lengths, may provide measurement capability.

Nucleic acid sequencing is a process that can be used to provide sequence information for a nucleic acid sample. Such sequence information may be helpful in diagnosing and/or treating a subject with a condition. For example, the nucleic acid sequence of a subject may be used to identify, diagnose and potentially develop treatments for genetic diseases. As another example, research into pathogens may lead to treatment for contagious diseases. Unfortunately, though, existing sequencing technology of the status quo is expensive and may not provide sequence information within a time period and/or at an accuracy that may be sufficient to diagnose and/or treat a subject with a condition.

SUMMARY

Recognized herein is the need for improved devices and methods for sequencing, amplifying, detecting, analyzing, and/or performing sample preparation procedures for nucleic acids and other biomolecules. The devices and methods described herein can perform a sequencing reaction a plurality of times, using different sequencing conditions. In some cases, signals derived from the sequencing reaction are analyzed at a plurality of frequencies or phases. This is in contrast to optimizing a single sequencing condition. The different sequencing conditions have various biases that can be leveraged, when combined, to provide a higher quality sequence (e.g., accurate, long read length) than can be achieved with any single condition. The disclosure also provides sensors, fluidic delivery systems and methods for fluid processing and analyte detection.

An aspect of the disclosure provides a method for a method for characterizing a biological molecule or a biological reaction associated with the biological molecule. The method comprises: (a) in a first solution, coupling the biological molecule to the Debye layer of a plurality of electrodes such that the plurality of electrodes and the biological molecule provide an electrical current flow path for detecting a signal indicative of the biological molecule or the biological reaction; (b) detecting the biological molecule or the biological reaction using the plurality of electrodes in the first solution; (c) replacing the first solution with a second solution, where the first solution is different than the second solution with respect to at least one of a type of polymerase, a concentration of the polymerase, a type of ion(s) and a concentration of the ion(s); and (d) in the second solution, detecting the signal indicative of the biological molecule or the biological reaction using the plurality of electrodes.

In some cases, the method further comprises repeating (c) and (d). Additionally, the first solution can have a different temperature, pressure, and/or composition than the second solution. In some cases, the method further comprises using one or more computer processors to analyze a first data set associated with the detecting in (b) and a second data set associated with the detecting in (d) to arrive at a characterization of the biological molecule or the biological reaction. The characterization can comprise one or both of identifying or sequencing the biological molecule; and quantifying the amount of the biological molecule or the extent of the biological reaction.

In some cases, detecting in the first solution has a higher quality bias than detecting in the second solution. In such cases, an associated analysis of the first data set and the second data set may provide relatively more weight to the detection associated with the higher quality bias. Moreover, the higher quality bias can have greater accuracy than other biases with respect to detecting the biological molecule or the biological reaction than other biases.

Furthermore, the biological molecule may be attached to a bead, optionally through a linker (e.g., a linker covalently or non-covalently attached to the bead). In some cases, the biological molecule is a nucleic acid molecule and the method may further comprise sequencing the nucleic acid molecule. In some cases, the plurality of electrodes comprises at least two electrodes. In some cases, the plurality of electrodes may be exposed to the first solution and second solution.

An additional aspect of the disclosure provides a method for characterizing a biological molecule or a biological reaction associated with a biological molecule. The method comprises: (a) distributing a plurality of biological molecules into an array of sensors comprising at least a first sub-set and a second sub-set of sensors, where each sensor comprises a plurality of electrodes for detecting a signal indicative of a biological molecule or a reaction associated with the biological molecule; (b) directing a first solution to the first sub-set of sensors and using the plurality of electrodes of each sensor of the first sub-set of sensors to detect signals indicative of a first sub-set of the biological molecules or a reaction associated with the first sub-set of the biological molecules in the first subset of sensors; and (c) directing a second solution to the second sub-set of sensors and using the plurality of electrodes of each sensor of the second sub-set of sensors to detect signals indicative of a second sub-set of the biological molecules or a reaction associated with the second sub-set of the biological molecules in the second subset of sensors, where the second solution is different than the first solution.

In some cases, the method further comprises repeating (b) and/or (c) with one or more additional solutions. In some cases, (b) and (c) are performed simultaneously. Additionally, the first solution can have a different temperature, pressure, and/or composition than the second solution. In some cases, the method further comprises using one or more computer processors to analyze a first data set associated with the detecting in (b) and a second data set associated with the detecting in (c) to arrive at a characterization of the biological molecule or the biological reaction. The characterization can comprise one or both of identifying or sequencing the biological molecules; and quantifying the amount of the biological molecule or the extent of the biological reactions.

In some cases, detecting in the first solution has a different bias than detecting in the second solution and an associated analysis of the first data set and the second data set gives relatively more weight to the detection associated with the higher quality bias. The higher quality bias can be more accurate when detecting the biological molecules or the biological reactions from other biases. In some cases, the first sub-set of sensors has a different bias than the second sub-set of sensors, and the one or more computer processors give relatively more weight to the detection associated with the higher quality bias.

In some cases, the biological molecules are attached to beads. Moreover, the biological molecules can be nucleic acid molecules and the method may further comprise sequencing the nucleic acid molecules. In some cases, the first sub-set of sensors has different geometries or materials of construction than the second sub-set of sensors. In some cases, the method further comprises detecting the biological molecule or the biological reaction using at least 2, at least 3, at least 4, at least 5, at least 6, at least 7, at least 8, at least 9, at least 10, at least 15, at least 20 or more sub-sets of sensors, each having a different geometry or material of construction. In some embodiments, the plurality of electrodes comprises at least two electrodes and/or may be exposed to the first solution and second solution.

In another aspect, the disclosure provides a method for sequencing a nucleic acid molecule. The method comprises (a) positioning a nucleic acid molecule adjacent to a sensor having at least two electrodes such that the at least two electrodes are electrically coupled to a Debye layer having at least a portion of the nucleic acid molecule, thereby providing an electrical current flow path for detecting a signal(s) indicative of the nucleic acid molecule or complement thereof; (b) subjecting the nucleic acid molecule to a primer extension reaction under at least two different reaction conditions that are selected for a sequencing bias selected from the group consisting of G-C bias and A-T bias; and (c) using the sensor to detect the signal(s) during the primer extension reaction, thereby sequencing the nucleic acid molecule at an accuracy of at least about 75%, at least about 80%, at least about 85%, at about 90%, at least about 95%, at least about 99% or more. In some cases, at least a portion of the nucleic acid molecule is electrically coupled to a Debye layer associated with the at least two electrodes. The at least two electrodes may be exposed to a solution having the nucleic acid molecule.

In an additional aspect, the disclosure provides a system for delivering a plurality of fluids to a sensor array for processing or analyzing a biological sample. The system comprises: (a) a plurality of reservoirs, each reservoir adapted to contain a separate reagent; (b) a sensor array in fluidic communication with each of the reservoirs by way of an individual reagent channel fluidically connecting each reservoir to the sensor array, where the sensor array comprises individual sensors each having at least two electrodes that, during use, are electrically coupled to a Debye layer associated with the biological sample; (c) a wash channel in fluidic communication with each individual reagent channel and a wash reservoir; (d) a plurality of pneumatic channels adapted to individually adjust a pressure of each of the plurality of reservoirs; and (e) a plurality of valves on any combination of the individual reagent channels and the wash channels, where the plurality of pneumatic lines and the plurality of valves are configured to deliver a given reagent from a given one of the plurality of reservoirs to the sensor array without contamination from other reagents in a remainder of the plurality of reservoirs. In some cases, the plurality of pneumatic channels are pressurized such that the wash channels have a higher pressure than the individual reagent channels.

In some cases, the system further comprises a waste channel in fluidic communication with each individual reagent channel and a waste reservoir. In some cases, the sensor array is capable of detecting nucleic acid sequencing reactions. In some cases, the reservoirs each contain one or more of the nucleotides adenine, guanine, thymine and cytosine. Moreover, reagents contacting the sensor array can be changed with relatively short times. For example, the reagent contacting the sensor array can be changed in less than about 30 seconds, in less than about 25 seconds, in less than about 20 seconds, in less than about 15 seconds, in less than about 10 seconds, in less than about 7 seconds, in less than about 5 seconds, in less than about 3 seconds, in less than about 1 second or less.

Furthermore, in some cases, the individual reagent channels and the wash channels can be positioned at an angle with respect to each other. For example, each of the individual reagent channels and the wash channels form an angle of at least about 5°, at least about 10°, at least about 15°, at least about 20°, at least about 25°, at least about 30°, at least about 40°, at least about 45°, at least about 50°, at least about 55°, at least about 60°, at least about 65°, at least about 70°, at least about 75°, at least about 80°, at least about 85° or at least about 89°. In some cases, each of the individual reagent channels and the wash channels form a right angle with respect to each other.

In some cases, each of the individual reagent channels and the wash channels form a right angle with respect to the sensor array. In some cases, each of the individual reagent channels and the wash channels form an angle that is from about 10° to 90° from, from about 30° to 90°, from about 45° to 90° or from about 60° to 90° with respect to the sensor array. In some cases, each of the individual reagent channels and the wash channels form an angle that is about 5°, at least about 10°, at least about 15°, at least about 20°, at least about 25°, at least about 30°, at least about 40°, at least about 45°, at least about 50°, at least about 55°, at least about 60°, at least about 65°, at least about 70°, at least about 75°, at least about 80°, at least about 85° or at least about 89° with respect to the sensor array.

In another aspect, the disclosure provides a method for delivering a plurality of fluids to a sensor array for processing or analyzing a biological sample. The method comprises: (a) injecting a first reagent from a first reservoir, through a first reagent channel into a sensor chamber comprising an array of sensors, where the array of sensors comprises individual sensors each having at least two electrodes that, during use, are electrically coupled to a Debye layer associated with the biological sample; (b) detecting a first signal from the array of sensors in the presence of the first reagent; (c) injecting a first wash fluid through a first wash channel, which first wash channel intersects the first reagent channel at a junction point between the first reservoir and the sensor chamber, such that the first wash fluid flows into the sensor chamber and the first wash fluid displaces at least a portion of the first reagent in the first reagent channel between the bisection point and the first reservoir; (d) injecting a second wash fluid through a second wash channel, which second wash channel intersects a second reagent channel at a junction point between a second reservoir and the sensor chamber, such that the second wash fluid flows into the sensor chamber and the second wash fluid displaces the first reagent in the second reagent channel; (e) injecting a second reagent from the second reservoir, through the second reagent channel into a sensor chamber; and (f) detecting a second signal from the array of sensors in the presence of the second reagent. In some cases, the method further comprises pressurizing the first wash channel, the second wash channel and the third wash channel to a pressure that is greater than a pressure of the first reservoir and the second reservoir.

In some cases, the method further comprises, prior to (e), injecting a third wash fluid through a third wash channel, which third wash channel intersects with a third reagent channel at a junction point between a third reservoir and the sensor chamber, such that the third wash fluid flows into the sensor chamber and the third wash fluid displaces the first reagent in the third reagent channel. Moreover, in some cases, the sensor the sensor array can detect a nucleic acid sequencing reaction of the biological sample and/or the first reagent and the second reagent may comprise different nucleotides.

Via the aid of systems described herein, time elapsed of fluidic delivery method execution can be reduced or minimized. For example, the time elapsed between (b) and (f) can be less than about 30 seconds, less than about 25 seconds, less than about 20 seconds, less than about 15 seconds, less than about 10 seconds, less than about 7 seconds, less than about 5 seconds, less than about 3 seconds or less than about 1 second.

Furthermore, in some cases, the individual reagent channels and the wash channels can be positioned at an angle with respect to each other. For example, each of the individual reagent channels and the wash channels form an angle of at least about 5°, at least about 10°, at least about 15°, at least about 20°, at least about 25°, at least about 30°, at least about 40°, at least about 45°, at least about 50°, at least about 55°, at least about 60°, at least about 65°, at least about 70°, at least about 75°, at least about 80°, at least about 85° or at least about 89°. In some cases, each of the individual reagent channels and the wash channels form a right angle with respect to each other.

In some cases, each of the individual reagent channels and the wash channels form a right angle with respect to the sensor array. In some cases, each of the individual reagent channels and the wash channels form an angle that is from about 10° to 90° from, from about 30° to 90°, from about 45° to 90° or from about 60° to 90° with respect to the sensor array. In some cases, each of the individual reagent channels and the wash channels form an angle that is about 5°, at least about 10°, at least about 15°, at least about 20°, at least about 25°, at least about 30°, at least about 40°, at least about 45°, at least about 50°, at least about 55°, at least about 60°, at least about 65°, at least about 70°, at least about 75°, at least about 80°, at least about 85° or at least about 89° with respect to the sensor array.

Moreover, in another aspect, the disclosure provides a sensor for sensing a biological molecule. The sensor comprises: (a) a first electrode having a first surface and a second electrode having a second surface, which electrodes are electrically isolated from one another in the absence of a bead situated adjacent to the first electrode and second electrode, which surfaces are oriented at an angle that is greater than 0° with respect to one another such that, during sensing, the bead is substantially immobile; and (b) a securing member that is adjacent to the first electrode and/or second electrode, where during sensing, the securing member positions the bead adjacent to the surfaces such that the electrodes are within a Debye layer of the bead.

In some cases, the surfaces are oriented at an angle that is greater than 5°, greater than 10°, greater than 15°, greater than 20°, greater than 25°, greater than 30°, greater than 35°, greater than 40°, greater than 45°, greater than 50°, greater than 55°, greater than 60°, greater than 65°, greater than 70°, greater than 75°, greater than 85°, greater than 89° or they are at a right angle (e.g., orthogonal) with respect to one another such that, during sensing, the bead is substantially immobile. In some cases, the biological molecule is a nucleic acid. In some cases, the securing member is adjacent to the first electrode and the second electrode. In some cases, the first electrode and/or the second electrode comprise an indentation for restricting movement of the bead. In some cases, the securing member comprises a magnet (e.g., an electromagnetic, a permanent magnet, a magnetic material, etc.).

An additional aspect of the disclosure provides a method for detecting an analyte. The method comprises: (a) activating a sensor comprising at least two electrodes by (i) applying at least two voltage waveforms with different frequencies to the at least two electrodes, and (ii) deriving one or more first electrical parameters from first signals indicative of first impedances each associated with one of the at least two voltage waveforms; (b) coupling the analyte to a support proximate to the at least two electrodes or a molecule coupled to the support; (c) applying the at least two voltage waveforms to the at least two electrodes and deriving one or more second electrical parameters from second signals indicative of second impedances each associated with one of the at least two voltage waveforms; and (d) determining a presence of the analyte by comparing at least one of the first electrical parameters with at least one of the second electrical parameters.

In some cases, the analyte comprises a biological molecule, which may be, for example, a nucleic acid, a protein and/or a peptide. In the case of nucleic acid sequencing, the analyte may comprise a nucleotide base that is a component of a nucleic acid sequencing reaction. Moreover, in some cases, the support comprises a bead and/or at least one of the at least two voltage waveforms comprises a square wave. Frequencies of the at least two waveforms can comprise frequencies along a continuous frequency sweep.

Additionally, the one or more first and/or second electrical parameters may selected from a resistance associated with the support; a fluid capacitance associated with fluid proximate to at least one of the at least two electrodes; an electrode capacitance associated with one or more of the at least two electrodes; and a combination thereof. In some cases, the first signals comprise a first current and a second current each associated with one of the at least two waveforms. The first impedances can be derived from the first current and the second current. In some cases, in (a), the one or more first electrical parameters are derived using the first impedances.

In some cases, the second signals comprise a first current and a second current each associated with one of the at least two waveforms. The second impedances can be derived from the first current and the second current and, in (c), the one or more second electrical parameters can be derived from the second impedances.

In some cases, one or more of the first impedances and/or the second impedances are an impedance associated with a Debye layer of the support or a molecule coupled to the support. Moreover, in some cases, one or more of the at least two electrodes is positioned within a Debye layer of the support. Additionally, (a) and/or (c) may be performed in the presence of a fluid (e.g., a buffer) to which one or more of the at least two electrodes are exposed. In some cases, the deriving in (a) and/or (c) is completed with the aid of one or more computer processors.

In an additional aspect, the disclosure provides a method for detecting an analyte. The method comprises: (a) activating a sensor comprising at least two electrodes by (i) applying at least two voltage waveforms with different phases to the at least two electrodes, and (ii) deriving one or more first electrical parameters from first currents each associated with one of the at least two voltage waveforms; (b) coupling the analyte to a support proximate to the at least two electrodes or a molecule coupled to the support; (c) applying the at least two voltage waveforms to the at least two electrodes and deriving one or more second electrical parameters from second currents each associated with one of the at least two voltage waveforms; and (d) determining a presence of the analyte by comparing at least one of the first electrical parameters with at least one of the second electrical parameters.

In some cases, the analyte comprises a biological molecule such as, for example, a nucleotide base, a nucleic acid, a protein and/or a peptide. In some cases, the analyte comprises a nucleotide base that is a component of a nucleic acid sequencing reaction. In some cases, the support comprises a bead. Moreover, at least one of the at least two voltage waveforms may comprise a square wave.

Additionally, in (a), the deriving one or more electrical parameters can comprise deriving phase derivatives for the first currents and deriving a Fourier transform (e.g., a Fast Fourier Transform (FFT)) for the phase derivatives. In such cases, the method can further comprise deriving an impedance from the Fourier transform and, in some cases, deriving the one or more first electrical parameters from the impedance.

Moreover, in (c), the deriving can comprise deriving phase derivatives for the second currents and deriving a Fourier transform (e.g., Fast Fourier Transform (FFT)) for the phase derivatives. In such cases, the method can further comprise deriving an impedance from the Fourier transform and, in some cases, deriving the one or more second electrical parameters from the impedance.

Additionally, the one or more first and/or second electrical parameters can be selected from a resistance associated with the support; a fluid capacitance associated with fluid proximate to at least one of the at least two electrodes; a capacitance associated with one or more of the at least two electrodes; and a combination thereof. In some cases, one or more of the at least two electrodes is positioned within a Debye layer of the support. Furthermore, (a) and/or (c) may be performed in the presence of a fluid (e.g., a buffer). One or more of the at least two electrodes may be exposed to the fluid. Moreover, the deriving in (a) and/or (c) can be completed with the aid of one or more computer processors.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1:
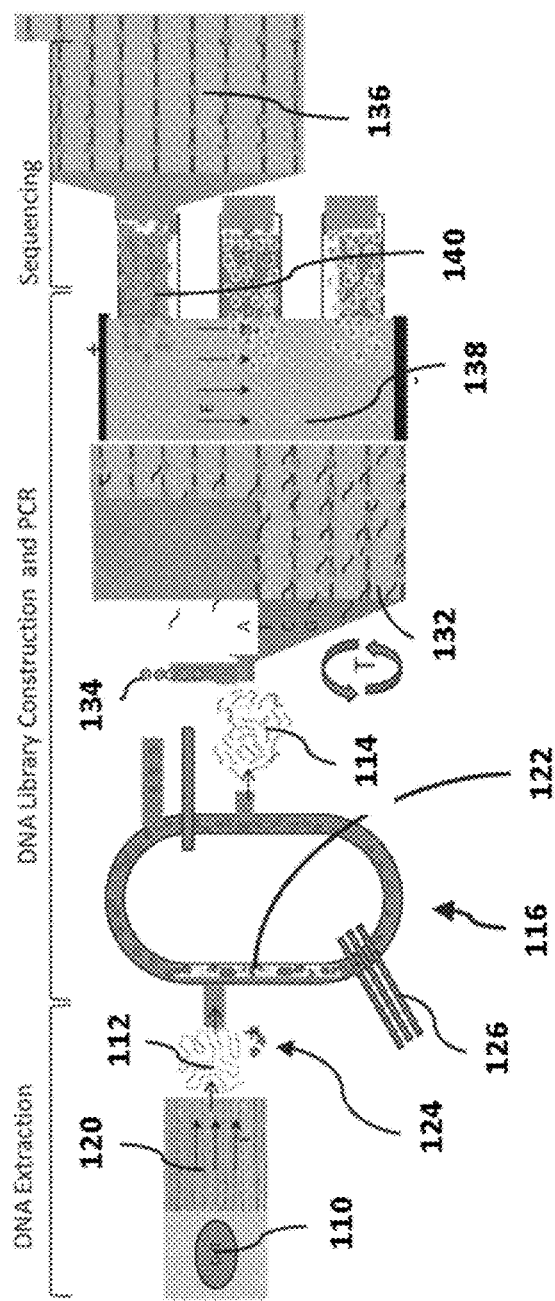
FIG. 1 is a schematic of an example integrated sequencing platform.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "adjacent to," as used herein, generally means next to, in proximity to, or in sensing or electronic vicinity (or proximity) of. For example, a first object adjacent to a second object can be in contact with the second object, or may not be in contact with the second object but may be in proximity to the second object. In some examples, a first object adjacent to a second object is within about 0 micrometers ("microns"), 0.001 microns, 0.01 microns, 0.1 microns, 0.2 microns, 0.3 microns, 0.4 microns, 0.5 microns, 1 micron, 2 microns, 3 microns, 4 microns, 5 microns, 10 microns, or 100 microns of the second object.

The term "nucleic acid," or "polynucleotide," as used herein, generally refers to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double stranded. In some cases, a nucleic acid molecule is circular.

The terms "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or ribonucleotides (RNA), or analogs thereof. A nucleic acid molecule can have a length of at least about 100 bases, 200 bases, 300 bases, 400 bases, 500 bases, 1 kilobase (kb), 2 kb, 3, kb, 4 kb, 5 kb, 10 kb, or 50 kb. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may include one or more non-standard nucleotide(s), nucleotide analog(s) and/or modified nucleotides.

Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyfluracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A. *Nat. Chem. Biol.* 2012 July; 8(7):612-4, which is herein incorporated by reference for all purposes.

The term "polymerase," as used herein, generally refers to any enzyme capable of catalyzing a polymerization reaction. Examples of polymerases include, without limitation, a nucleic acid polymerase. The polymerase can be naturally occurring or synthesized. An example polymerase is a Φ29 polymerase or derivative thereof. A polymerase can be a polymerization enzyme. In some cases, a transcriptase or a ligase is used (i.e., enzymes which catalyze the formation of a bond). Examples of polymerases include a DNA polymerase, an RNA polymerase, a thermostable polymerase, a wild-type polymerase, a modified polymerase, *E. coli* DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Tth polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some embodiments, the polymerase is a single subunit polymerase. The polymerase can have high processivity, namely the capability of the polymerase to consecutively incorporate nucleotides into a nucleic acid template without releasing the nucleic acid template.

The term "subject," as used herein, generally refers to an individual having a biological sample that is undergoing processing or analysis. A subject can be an animal or plant. The subject can be a mammal, such as a human, dog, cat, horse, pig or rodent. The subject can have or be suspected of having a disease, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease.

Integrated Sensing Platforms

The present disclosure provides an integrated sequencing platform that can include various components. The integrated sequencing platform can be used in various applications, such as sequencing a nucleic acid sample from a subject.

An integrated sequencing platform may include a nucleic acid (e.g., DNA) extraction system, a library construction system, an amplification system, an enrichment system, and a sequencing system. In some embodiments the systems may be separate and/or in modular format. In some embodiments, the integrated sequencing platform can include one, two, three, four, or all five of these systems. In some cases, the systems can be integrated within a single microfluidic device and/or a single array (e.g., a re-usable array). An example of such an integrated platform is depicted in FIG. 1. Other examples of such integrated sequencing platforms can be found in PCT Patent Application No. PCT/US2011/054769, PCT Patent Application No. PCT/US2012/039880, PCT Patent Application No. PCT/US2012/067645, PCT Patent Application No. PCT/US2014/027544, PCT Patent Application No. PCT/US2014/069624 and PCT Patent Application No. PCT/US2015/020130 each of which is incorporated herein by reference in its entirety for all purposes.

An integrated system may comprise a library construction system (e.g., nucleic acid library construction system), which may include a fragmentation and/or size selection element. An example of a library construction system is shown in FIG. 1. As shown in FIG. 1, a library construction system may include a nucleic acid (e.g., DNA) fragmentation and size selection element 116. Nucleic acid 112 provided to the fragmentation and size selection element 116 can be extracted from a biological sample (e.g., a cell 110) and separated 120 from other biological materials prior to fragmentation. The fragmentation and size selection element 116 can be configured to produce nucleic acid fragments, such as double-stranded nucleic acid fragments, which may or may not have blunted ends, via the elements and methods described below. The fragmentation and size selection element 116 can include one or more microfluidic channels 122 within which nucleic acid may be disposed along with a set of fragmentation beads 124. Nucleic acid 112 collected in a nucleic acid (e.g., DNA) extraction system (shown for example in FIG. 1) can be conveyed or "injected" into the nucleic acid (e.g., DNA) fragmentation and size selection element 116 by any suitable method (e.g., pressurized injection, electrophoretic movement, gravity feed, heat-induced movement, ultrasonic movement and/or the like). Similarly, fragmentation beads 124 can be conveyed into the nucleic acid (e.g., DNA) fragmentation element and size selection element 116 by any suitable method.

The fragmentation element and/or size selection element 116 may include a pump 126 to produce movement of a fluid (e.g., a fluid comprising nucleic acid (e.g., DNA) and fragmentation beads 124) within a microfluidic channel 122. The pump 126 can be, for example, a peristaltic pump. In some embodiments, the pump 126 can include one or more microfluidic elements in fluid communication with the microfluidic channel 122, and may have a flexible side-wall that, when deformed, produces a flow within the microfluidic channel 122. In other embodiments, however, any other suitable mechanism can be used as an alternative or in addition to produce movement fluid within the microfluidic channel 122, with non-limiting examples, that include selective heating and cooling of the fluid, pneumatic pressurization of the microfluidic channel, electrophoretic motion, or the like.

The fragmentation beads 124 can be constructed from any material suitable for separating, cutting and/or otherwise dividing a nucleic acid (e.g., DNA) into nucleic acid fragments (e.g., DNA fragments). In some embodiments, the fragmentation beads 124 can be constructed from glass, polydimethylsiloxane (PDMS), ceramic or the like. Moreover, the fragmentation beads 124 can have any suitable size and/or geometry such that the fragmentation element produces fragments having the desired characteristics (e.g., length, strand characteristics, or the like). For example, in some embodiments, the fragmentation beads 124 can be substantially spherical and can have a diameter of 50 micrometers (µm) or less. In other embodiments, the fragmentation beads can have a diameter of 500 nm or less, or any diameter between 50 µm and 500 nm.

Moreover, the size and/or geometry of the microfluidic channel 122 (e.g., cross-sectional shape, aspect ratio or the like) can be selected such that the movement of the nucleic acid (e.g., DNA) within the microfluidic channel 122 and contact of the nucleic acid with the fragmentation beads 124 fragments (e.g., via shearing) the nucleic acid as desired. In some embodiments, the microfluidic channel 122 may be in the range of 1 to 500 µm in hydraulic diameter (i.e., the cross-sectional area of the microfluidic channel 122 can be substantially rectangular, thus the size can be represented as a hydraulic diameter). In other embodiments, the hydraulic diameter of the microfluidic channel 122 can be in the range of 10 to 200 µm. In yet other embodiments, the hydraulic diameter of the microfluidic channel 122 can be in the range of 500 nm or less. In other embodiments, the microfluidic channel 122 can have any suitable shape, such as semicircular, oval, tapered or the like. In some embodiments enzymatic polishing of sheared nucleic acid (e.g., DNA) ends can be done such that the ends are blunt ends. In other embodiments, an enzymatic solution can be conveyed into the microfluidic channel 122 to, at least partially, produce enzymatic fragmentation of nucleic acid (e.g., DNA).

As shown in FIG. 1, The fragments 114 that are generated by the by the size selection element 116 can be transferred to an amplification unit 132 along with beads 134 that are capable of binding the fragments 114. The flow rates of beads 134 and fragments 114 supplied to the amplification unit 132 can be carefully controlled such that on average less than 1 fragment is associated with a given bead. Binding of the fragments 114 to beads can be via any suitable route, including hybridization, covalent linkages, an associated binding ligand pair, etc. The amplification unit 132 can include an array of features that are each capable of retaining a bead. Beads may be bound to the array via magnetic (e.g., via a magnetic feature), electrostatic (e.g., via one or more electrodes) or via a member of a binding pair (e.g., via hybridization of nucleic acid with nucleic acid coupled to the array). Amplification of fragments bound to beads can then proceed in any suitable fashion, including via amplification methods described elsewhere herein, to generate a clonal population of beads. In some cases, a virtual well, as described elsewhere herein can be used to concentrate, direct and/or confine reagents to individual array sites.

Once amplification is complete, the clonal beads can be transported to a separation unit 138 that separates beads having amplicons from those without nucleic acid. In some cases, separation methods may make use of electrophoretic methods, as described elsewhere herein. Once separation is complete, beads 140 that have amplicons can be provided to a sensor array 136 (e.g., including a type of sequencing array described herein) and sequenced (e.g., including via a detection method described herein).

In some embodiments, nucleic acid (e.g., deoxyribonucleic acid (DNA)) amplification and sequencing may be performed sequentially within the same system. In such cases, sample nucleic acid may be associated with a plurality of carriers, such as, for example, beads or other types of particles. In some cases, the carriers may be magnetic carriers, such as, for example, magnetic beads or paramagnetic beads. In some cases, the magnetic carriers can be entered into an array (e.g., a substantially planar array comprising a substantially planar substrate) of magnetic features such that the magnetic carriers are held in place by a localized magnetic field at each position (e.g., pixel) of the array. In some embodiments, carriers (including magnetic carriers) can be held in place at each position of an array (e.g., a substantially planar array) by electrostatic force via one or more electrodes due to the charge of the carrier or the associated nucleic acid. In other embodiments, the carriers can be held in place at each position of the array by physical trenches or wells. In some embodiments, the carriers can be held in place at each position of the array by interaction of a species bound to the carrier with a species bound to the array (e.g., hybridization of oligonucleotides or via ligand-capture moiety pairs). Upon immobilization of the carriers to an array, amplification of the associated nucleic acid and sequencing of the amplified nucleic acid can be completed sequentially or simultaneously.

In some embodiments, carriers may be first entered into an array (e.g., via flow through microfluidic channels associated with the array) and captured by the array. After carrier capture, sample nucleic acid may be contacted with the array (e.g., via flow through microfluidic channels associated with the array) and subsequently captured by the carriers. Capture may occur, for example, via nucleic acids associated with the carriers and capable of hybridizing with the sample nucleic acid. Such nucleic acids may also be used as primers for amplification reactions described elsewhere herein. In some embodiments, nucleic acid to be amplified and/or sequenced is associated with carriers prior to their capture by an array.

Alternatively, a surface of the array (e.g., sensor surface, array substrate surface, etc.) may comprise elements suitable for capturing sample nucleic acid, including nucleic acids capable of hybridizing with the sample nucleic acid. Such nucleic acids may also be capable of serving as primers for amplification reactions described elsewhere herein. Such a configuration may be suitable for amplifying and sequencing a nucleic acid in the absence of a carrier.

In some embodiments, the sample nucleic acid may be provided to an array at dilute concentrations in order to obtain a desired ratio of molecules of sample nucleic acid to carrier. For example, ratios of one molecule of nucleic acid for one carrier (e.g., bead), one molecule of nucleic acid for two carriers, one molecule of nucleic acid for three carriers, one molecule of nucleic acid for five beads, or less, etc. may be desired.

During amplification reactions, one or more electrodes at a sensor position of the array may be used for concentration of reagents useful for nucleic acid amplification, forming a "virtual well" associated with a carrier, sensor, or substrate at the array position via an electric field. Virtual wells can permit amplification of nucleic acids at a sensor position without cross-contamination of reactants with those of other sensors of the array. In certain embodiments, amplification within a virtual well can generate a clonal population of nucleic acid associated with a carrier, sensor surface, or substrate associated with the virtual well.

Nucleic acid amplification may be performed in multiple cycles if desired. Once a first round of amplification is completed after contacting an array with sample nucleic acid, an array may be washed in order to remove any unbound amplicons and other reagents in solution. Following washing, a second round of amplification may be completed, by contacting the array with sample nucleic acid and subjecting captured sample nucleic acid to appropriate conditions. Where clonal populations are generated, the sample may bind only to sites (e.g., carriers, sensor surfaces, etc.) not already comprising amplicons, as sites with amplicons from first round of amplification may be fully loaded amplicons. The process may be repeated for any number of amplification cycles until capture sites are exhausted. Utilizing multiple rounds of amplification may help eliminate double Poisson distribution problems and help ensure that each sensor site is associated with only nucleic acid sequence, such as a clonal population of amplicons attached to a carrier (e.g., bead). Such attachment may be direct attachment of an amplicon to the carrier, or attachment of the amplicon of the carrier through a linker, such as a nucleic acid molecule directly bound to the carrier. Moreover, multiple rounds of amplification may also help maximize the use of an array, as each round of amplification can better ensure that all of the pixels of the array of occupied with amplicons for sequencing.

Moreover, during sequencing reactions, one or more of the same electrodes and/or different electrodes may be used to detect a reaction of interest, such as nucleotide incorporation. In some cases, a sensor may include at least two electrodes that measure signals indicative of a change of impedance, a change in charge, a change in ion concentration, and/or a change in conductivity associated with a biological reaction (e.g., nucleotide incorporation during a primer extension reaction) or binding of a biological species with another biological species (e.g., hybridization of a nucleic acid to another nucleic acid, protein binding, etc.). In some cases, sensing may be completed using a NanoNeedle and/or NanoBridge sensor, or other electrical or optical sensors suitable for detection. A NanoBridge sensor may function as a pH or charge sensor, as described in U.S. Patent Publication No. US 2012/0138460, which is incorporated herein by reference in its entirety. A sensor (e.g., NanoNeedle sensor) may function as a charge, conductivity and/or impedance sensor, as described in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624 and PCT Patent Application No. PCT/US2015/020130 each of which is incorporated herein by reference in its entirety. In some embodiments, a sequencing reaction may be DNA sequencing.

The detection may be based on at least one of local pH change, local impedance change, local heat detection, local capacitance change, local charge concentration (or change thereof), and local conductivity change associated with a biological reaction, such as nucleotide incorporation, hybridization and ligand binding. In some embodiments, detection may be based on a local conductivity change, local impedance change, local capacitance change, local charge concentration (or change thereof) of a carrier, a nucleic acid, or other analyte associated with the carrier and/or a sensor. Such measurements may be made by directly detecting (or detecting signals that are indicative of) a local pH change, local impedance change, local heat detection, local capacitance change, local charge concentration (or change thereof), and local conductivity change, such as local conductivity change of a carrier, a nucleic acid (or other analyte) associated with the carrier and/or a sensor. In some cases, one or more of these changes may be a change within the Debye layer of a carrier (e.g., bead) or species coupled to a carrier (e.g., nucleic acid). In some cases, detection occurs within the Debye length (e.g., Debye layer) of (i) a carrier, (ii) a nucleic acid associated with a carrier or sensor, and/or (iii) a sensor. The Debye length can characterize a thickness of a charge or conductivity boundary layer (e.g., Debye layer) around the carrier, nucleic acid associated with the carrier or sensor, and/or sensor. For example, the detection can occur within a Debye layer of the carrier. As another example, the detection occurs within the Debye layer of the sensor (e.g., one or more electrodes of the sensor). As another example, the detection occurs within the Debye layer spanning the sensor and the carrier. Such a sensor configuration is described, for example, in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which is incorporated herein by reference in its entirety. Where a sensor comprises at least two electrodes, the two electrodes may be electrically coupled to the Debye layer of a carrier (e.g., a bead) or a species coupled to a bead (e.g., a nucleic acid). In some cases, one or more of the at least two electrodes may be within the Debye layer of a carrier (e.g., a bead) or a species coupled to a bead (e.g., a nucleic acid).

Following the completion of sequencing, carriers/nucleic acids may be dissociated from the array, the carriers and array optionally separated from bound species and washed, and either or both of the carriers and array subsequently re-used for another round of amplification and/or sequencing. Dissociation of a carrier from the array may be completed, for example, by removal/reversal of a magnetic and/or electric field used to hold the carrier in place. In addition or as an alternative, fluid flow and/or other type of field (e.g., external magnetic field, external electric field) capable of exerting forces sufficient for overcoming magnetic and/or electrostatic forces used to hold a carrier in place may also be used to dissociate the carrier from an array. Where nucleic acids are directly associated with the array, in the absence of a carrier, the array may be treated with appropriate reagents or energy (e.g., enzymatic reagents, chemical reagents, thermal energy, etc.) to remove bound nucleic acids from the array. In some cases, though, it may be desirable to remove a carrier or nucleic acid from an array prior to amplification and/or sequencing. Such removal can be achieved in analogous fashion as described herein.

In some embodiments, a combined amplification and sequencing system may comprise a magnetic array that can trap a magnetic bead or particle by magnetic force at a plurality of the array positions. In some cases, a magnetic bead may be a paramagnetic bead. Each of the array positions may also comprise electrodes capable of producing electric fields and/or functioning as sensors. Each magnetic bead or particle can comprise a nucleic acid (e.g., DNA) segment that may be clonally amplified, for example, with the aid of electric fields generated by one or more of the electrodes at each array position.

In some embodiments, a combined amplification and sequencing system may comprise an array of electrodes that can trap a magnetic bead or particle by electrostatic force at a plurality of the array positions. In some cases, a magnetic bead may be a paramagnetic bead. One or more of the same electrodes or different electrodes at each of the array positions may also be capable of producing electric fields and/or functioning as sensors. Each magnetic bead or particle can comprise a nucleic acid (e.g., DNA) segment that may be clonally amplified, for example, with the aid of electric fields generated by one or more of the electrodes at each array position.

Figure 2A:
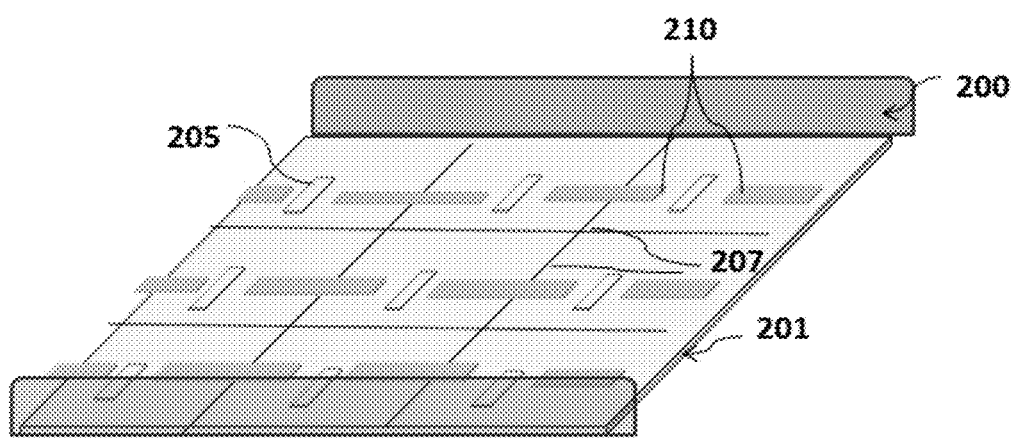
FIG. 2A shows a schematic of an example sensor array.

An example of a combined amplification and sequencing system and use of the example system is depicted in FIGS. 2A-2F. As shown in FIG. 2A, the system 200 may include an array on a substrate 201 that can comprise sensors (e.g., nanosensors) sometimes in communication with microfluidic channels defined within the platform. Sensors may be associated with substrate 201, and substrate 201 may also be associated with magnetic 210 and electrode 205 and 207 elements. Magnetic beads may be positioned over the sensors by magnetic 210 or electrode 205 and 207 elements. The magnetic elements may form localized magnetic fields and the electrode elements may form localized electric fields in order to position a carrier at each sensor of the array. Moreover, the magnetic and/or electric fields may create an area of confinement for carriers at each position of the array.

Figure 2B:
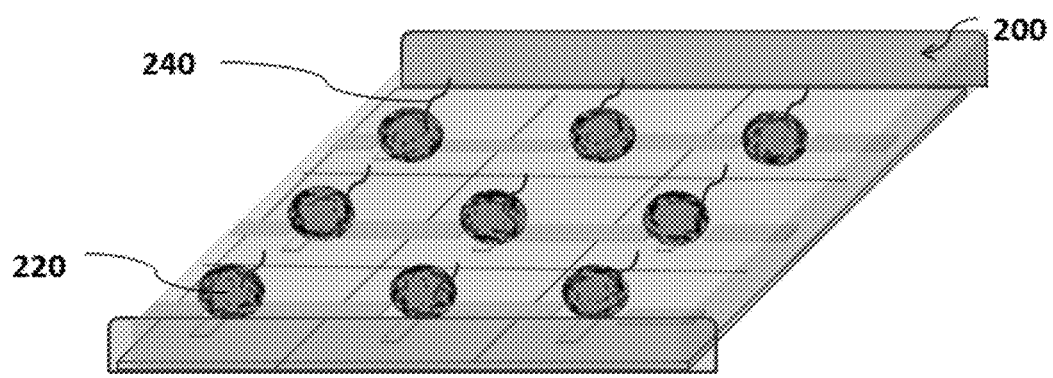
FIG. 2B shows a schematic of an example sensor array with carriers immobilized to the sensor array.

As shown in FIG. 2B, a sample comprising DNA 240 (e.g., DNA fragments) may be conveyed into the system 200. As can be appreciated, DNA 240 is shown as an example and may be any suitable type of nucleic acid, including types of nucleic acids described elsewhere herein. In some cases, introduction of the DNA 240 may be via microfluidic channels associated with the array. As shown, the array may be configured with pre-localized magnetic beads 220 and the magnetic beads may be associated with primers capable of hybridizing with DNA 240, such that DNA 240 is captured by and becomes associated with the beads 220. The magnetic beads 220 may be positioned on the array via the magnetic elements 210 and/or electrode 205 and 207 elements. Alternatively or in addition, primers may be attached, bound, or associated with a sensor at a position of the array and used to trap DNA 240 at the sensor.

Figure 2C:
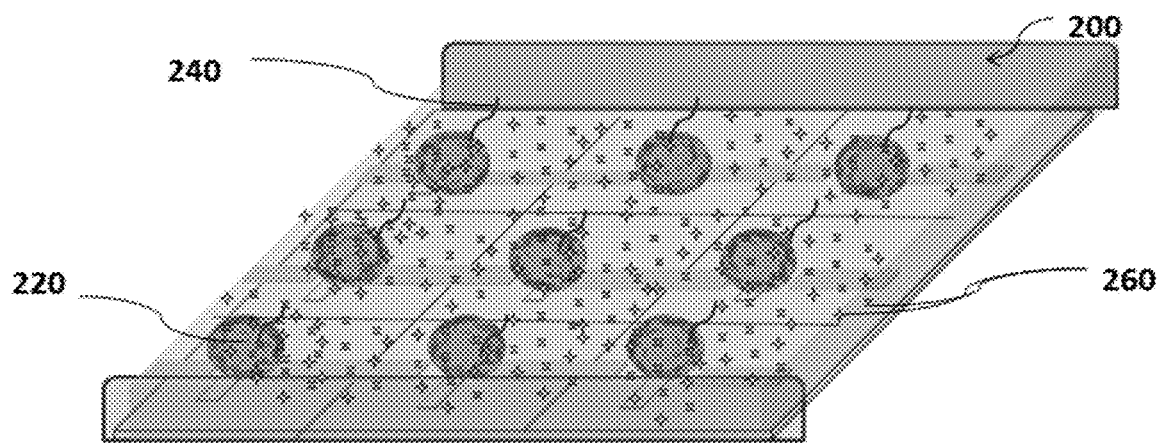
FIG. 2C shows a schematic of an example sensor array with carriers immobilized to the sensor array and in contact with reagents suitable for nucleic acid amplification.

As shown in FIG. 2C, reagents 260 (e.g., polymerase, deoxyribonucleotides (dNTPs), and additional primers) may be simultaneously, previously, or subsequently introduced to the array. In some cases, introduction of the reagents 260 may be via flow through microfluidic channels associated with the array, such that the reagents 260 are contacted with the magnetic beads 220 via flow. Via magnetic and/or electrostatic forces from the appropriate array elements, the magnetic beads 220 can be maintained in the desired position as reagents 260 make contact with the magnetic beads 220 via flow.

Figure 2D:
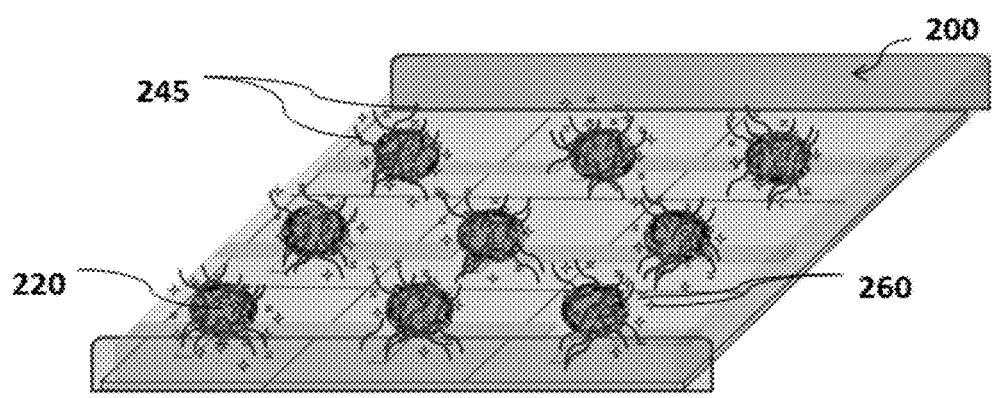
FIG. 2D shows a schematic of an example sensor array where nucleic acid amplification occurs at each array pixel of the sensor array.

As shown in FIG. 2D, the DNA 240 associated with magnetic beads 220 can be clonally amplified to produce amplified DNA 245 on the surface of the magnetic beads 220. Clonal amplification may be completed using any suitable method including a polymerase chain reaction (PCR), a primer extension reaction, isothermal amplification, or other techniques.

Figure 2E:
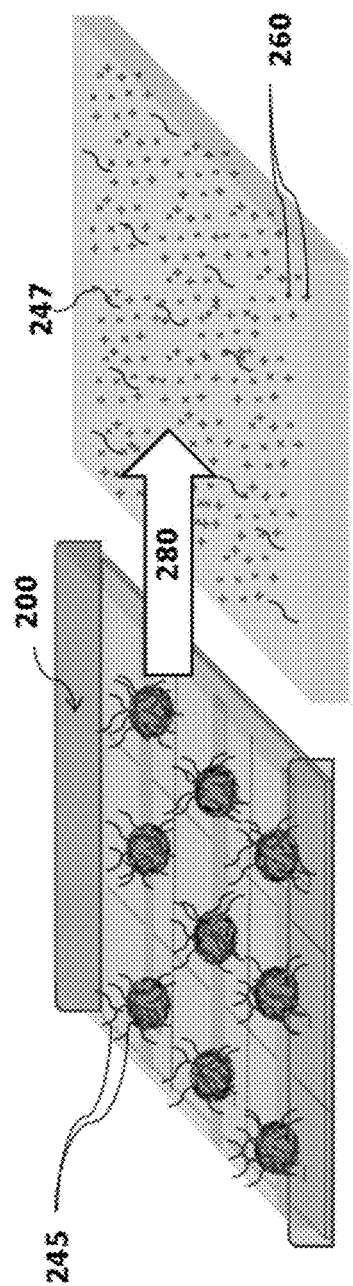
FIG. 2E shows a schematic example of removing reagents from an example sensor array.

As shown in FIG. 2E, the magnetic beads 220 in the array may be washed 280, removing unbound amplicons 247 and reagents 260 in solution following amplification of DNA 240. The result can be magnetic beads 220 comprising clonal sets of amplified DNA 255 associated with array positions. Washing 280 may be completed by any suitable method, such as, for example, washing with a buffer solution at a flow rate sufficient to remove the unbound amplicons 247 and reagents 260 in solution, but insufficient to detach the magnetic beads 220 from their respective positions on the array.

Figure 2F:
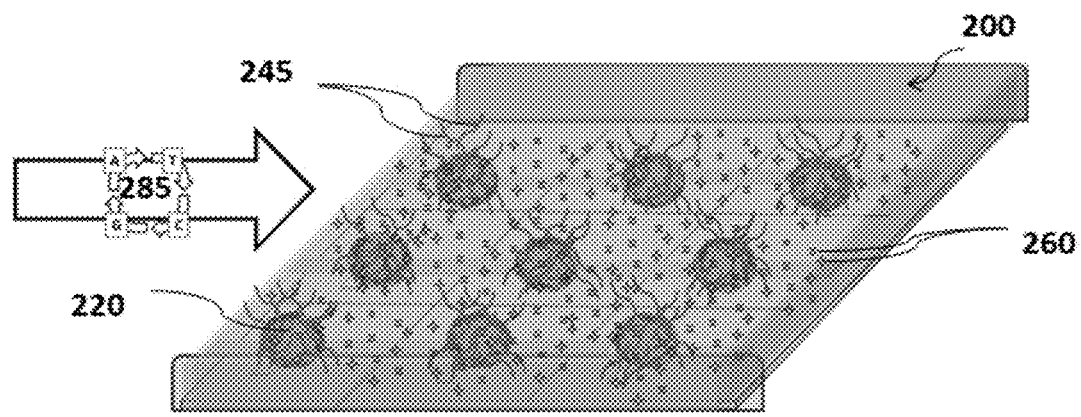
FIG. 2F shows a schematic of an example sensor array where nucleic acids are sequenced at each pixel of the sensor array.

As shown in FIG. 2F, another aliquot of reagents 260 (e.g., polymerase, primers, etc.) and sequential cycles of individual nucleotides 285 may then be contacted (e.g., via flow) with the sensor array, permitting incorporation of the nucleotides into the amplified DNA 255 of magnetic beads 220. nucleotides may be introduced in individual cycles, (e.g., cycle 1=A, cycle 2=T, etc.). where there may be a wash step with buffer in between each cycle to help reduce the chance of contamination from unincorporated nucleotides. Polymerase used for the sequencing reaction, may be the same type of polymerase that is used for the amplification reaction, or may be a different type of polymerase, and can be introduced prior to or with introduction of the nucleotides. Detection of the incorporated nucleotides during each cycle can be used to sequence the amplified DNA 245, and, thus, the original sample DNA 240. Detection may occur, for example, via one or both of electrodes 205 and 207. In some cases, electrodes 205 and 207 can detect nucleotide incorporation events by measuring local impedance changes of the magnetic beads 220 and/or the amplified DNA (or other nucleic acid) 255 associated with the magnetic beads 220. Such measurement can be made, for example, by directly measuring local impedance change or measuring a signal that is indicative of local impedance change. In some cases, detection of impedance occurs within the Debye length (e.g., Debye layer) of the magnetic beads 220 and/or the amplified DNA 245 associated with the magnetic beads 220. Nucleotide incorporation events may also be measured by directly measuring a local charge change or local conductivity change or a signal that is indicative of one or more of these as described elsewhere herein. Detection of charge change or conductivity change can occur within the Debye length (e.g., Debye layer) of the magnetic beads 220 and/or amplified DNA 245 associated with the magnetic beads 220.

Additional examples of combined amplification and sequencing systems, for example, may be found in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, which are incorporated herein by reference in their entireties.

In some embodiments, after amplification of sample nucleic acid onto carriers, but before sequencing, the carriers subjected to amplification conditions may be sorted in an enrichment system, such as, for example, an electrophoretic sorter, where sorting is achieved via electrophoretic force applied to carriers. The electrophoretic sorter may be part of a system used to conduct amplification and sequencing, or it may be part of a different system. In the electrophoretic sorter, null carriers (e.g., carriers without amplicons), as well as carriers subject to incomplete amplification or those comprising overly short amplicons, can be sorted from carriers comprising the desired amplicons. Additional examples of enrichment systems and electrophoretic sorters are described in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, which are incorporated herein by reference in their entireties.

An electrophoretic sorter may comprise channels capable of accepting sorted carriers. Carriers (e.g., beads) with appropriate amounts of amplified product and with amplicons of adequate length may have sufficient charge to be pulled off to an outlet channel. Where the electrophoretic sorter is a separate system, such carriers can be collected from the outlet channel and provided back into the amplification/sequencing system for sequencing, where the steps of introducing reagents and detecting nucleotide incorporation events may occur as described above.

Carriers (e.g., beads) without appropriate amounts of amplified product and/or without amplicons of adequate length may flow through the electrophoretic sorter and, instead, be directed into a waste channel. The carriers may be collected from the waste channel and may be reused for another cycle of amplification or other purpose upon appropriate cleaning to remove any undesirable species. For example, carriers may be washed with a bleaching agent, such as hydrogen peroxide, to help ensure that no contaminants remain on the carriers so that they may be reused.

The arrays and methods described herein can be used for a variety of applications and detection of different biological or biochemical moieties in addition to nucleic acids, such as antibody-antigen detection, protein detection, cell analysis, drug-discovery or screening, ligand, small molecules or other types of analysis. Moreover, the devices and methods described herein are not limited to DNA applications, and may be used for reactions and analysis of interest for RNA, protein detection, small molecules, etc. or other biomolecules.

Moreover, devices, systems and methods of the present disclosure may be used for various types of measurements, such as pathogen detection, protein detection and nucleic acid sequencing, including measuring a nucleic acid sequence and single-nucleotide polymorphism (SNP) detection. Such methods may be used by a subject, a healthcare provide to diagnose and/or treat the subject, or in forensics analysis.

In addition to sequencing reactions and/or nucleotide incorporation events, arrays and associated sensors may also be useful in sensing other biomolecules (e.g., oligonucleotides, proteins, small molecules, peptides, etc.) and/or reactions of interest using any of the methods and devices described herein, including directly measuring local impedance change, local charge change or local change in conductivity or measuring a signal that is indicative of local impedance change, local charge change or local change in conductivity.

In some embodiments, a sensor may detect a nucleic acid hybridization reaction. For example, a carrier (e.g., a bead) may be linked to a nucleic acid and hybridization of the nucleic acid with another nucleic acid (e.g., a primer or oligonucleotide probe) may be detected. In some embodiments, a sensor may detect a protein-protein interaction. For example, a carrier (e.g., a bead) may be coupled to a protein species (e.g., antibody, antibody fragment, peptide, etc.) capable of binding with an additional protein (e.g., a ligand). Binding of the additional protein to the protein species coupled to the carrier may be detected. Binding of small molecules to species linked to carriers may also be detected. In some cases, a plurality of detection methods may be employed to detect a biomolecule or a biological reaction of interest. Non-limiting examples of additional detection methods include an enzyme-linked immunosorbent assay (ELISA), detection of a tag (e.g., optical dyes, fluorescent dyes), detection of a released or generated species during a biological reaction of interest, etc.

A sensor (e.g., an individual sensor) described herein may be independently addressable. An independently addressable sensor as used herein, can refer to an individual sensor in an array whose response can be independently detected from the responses of other sensors in the array. An independently addressable sensor can also refer to an individual sensor in an array that can be controlled independently from other sensors in the array.

In some embodiments, the nucleic acids are not on carriers (e.g., beads). The nucleic acid can be immobilized directly onto a surface, such as a chip and/or sensor surface. For example, in order to integrate detection on-chip, various types of biomolecules may be patterned on-chip. Methods described herein may be used to covalently immobilize nucleic acids (e.g., DNA) directly onto a microchannel surface, a configuration which may be useful, for example, for an enzyme-linked DNA hybridization assay. In some embodiments, DNA or other nucleic acids can be directly attached to PDMS (polydimethylsiloxane) microfluidic channels, and the use of these PDMS-immobilized capture probes can be used for further immobilization of proteins. Such an approach may be used with other approaches for controlling surface properties of PDMS and the use of surface modifications for immobilization of DNA, RNA, and proteins, such as those described in D. Liu, R. K. Perdue, L. Sun, R. M. Crooks, Langmuir 20, 5905, which is entirely incorporated herein by reference.

In some embodiments, the immobilization of nucleic acid (e.g., DNA) onto a PDMS surface may involve a plurality of steps which can include: plasma-induced oxidation of the PDMS surface, functionalization of the oxidized surface with a silane coupling agent bearing a distal thiol group (mercaptopropylsilane, MPS), and subsequent reaction of the thiol groups with acrylamide-modified DNA. The silanization step can be carried out using a vapor-phase reaction method. The plasma-treated PDMS may be exposed to acid (e.g., HCl) vapor before the MPS vapor, as the acid can act as a catalyst that increases the rate of MPS immobilization on the PDMS surface. Subsequent exposure of the PDMS-linked DNA to its biotinylated complement can provide a platform for immobilization of a protein (e.g., alkaline phosphatase (AP)). PDMS immobilization of species can be compatible with a variety of species, including those described herein. In some cases, PDMS immobilization can provide for immobilizing any suitable oligonucleotide or streptavidin-modified protein onto a PDMS surface.

Devices for Biological Detection

The methods and systems described herein can be performed in a device. The device can perform any one or more of the operations of a method, including but not limited to nucleic acid extraction, fragmentation, library preparation, immobilization (e.g., on a carrier), amplification, confinement, bead enrichment, sequencing, or data analysis and communication.

Figure 3:
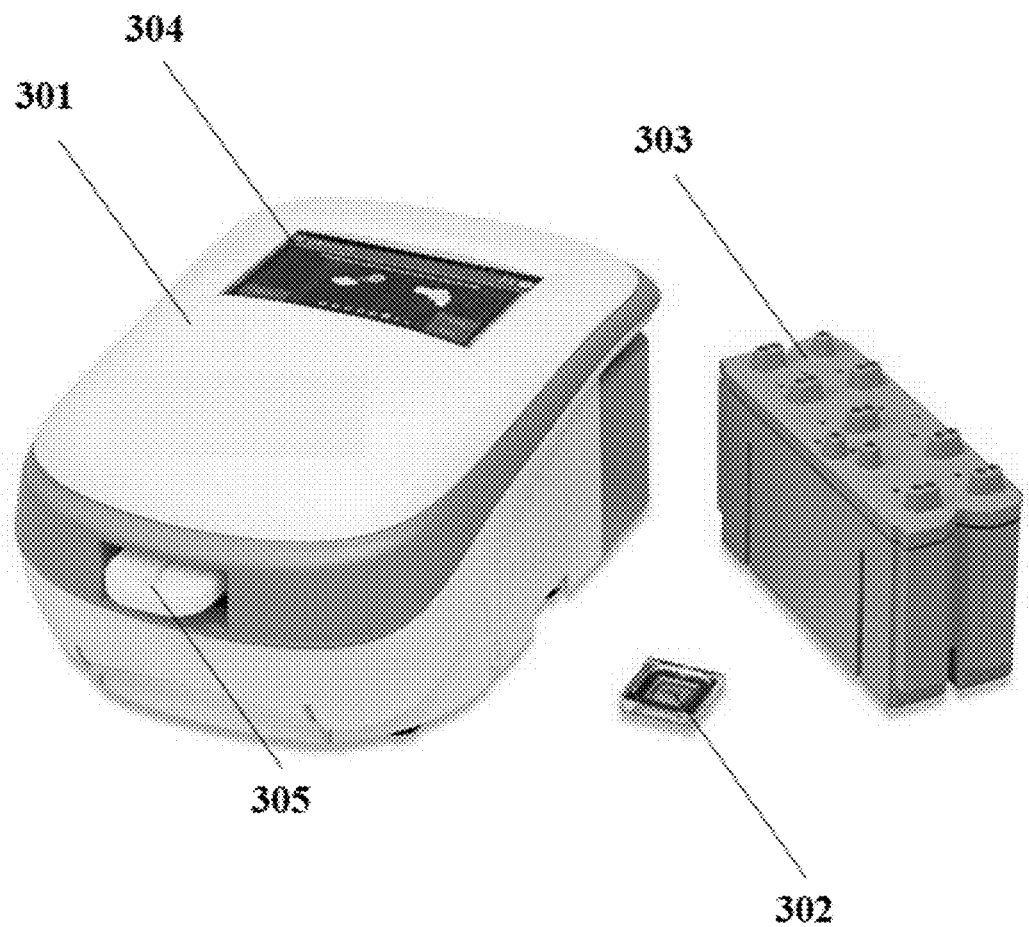
FIG. 3 shows a an example detection device comprising a housing, a removable chip and a removable reagent reservoir.

FIG. 3 shows a biological detection device 301, a removable chip 302 with an array of sensors, and a reagent reservoir 303 that can be inserted into and removed from the biological detection device 301. In some examples, the reagent reservoir 303 includes primers, nucleotides and polymerase enzymes for nucleic acid sequencing.

The biological detection device 301 can include a screen 304 that can include a user interface, such as a graphical user interface. The screen 304 can enable a user to operate the device 301, such as for nucleic acid sequencing.

The biological detection device 301 can include a port 305 that is configured to accept the removable chip 302. In some examples, upon insertion of the removable chip 302 into the device 301, nucleic acid sequencing can be performed using the array of sensors of the chip 302 and the reagents in the reagent reservoir 303.

An aspect of the present disclosure provides a sensing device comprising a sensing array with a plurality of sensors in a housing, where at least a subset of the plurality of sensors is individually addressable, where each sensor of the plurality is adapted to directly measure an electronic signature (e.g., a change of impedance, a change in charge, a change in conductivity, a change in ion concentration, etc.) associated with a biological species or reaction associated with a biological species in solution, where the housing has a footprint that is less than or equal to about 250,000 (square millimeters) $mm^2$, and where the device has a weight that is less than or equal to about 200 pounds, 175 pounds, 150 pounds, 125 pounds, 100 pounds, 75 pounds, 50 pounds, 25 pounds, 10 pounds or less. In some embodiments, the sensing device does not include wells. As an alternative, the sensing device can include wells. The sensing array can be removable from the housing.

In an embodiment, the device further comprises a fluid flow path in fluid communication with the sensing array. The fluid flow path can be in communication with a repository comprising one or more reagents for a biological reaction (e.g., nucleic acid sequencing). In some cases, the fluid flow path can provide beads to the sensing array in an emulsion or, alternatively, without an emulsion.

In some situations, at least some, all or substantially all of the plurality of sensors can be individually addressable. For instance, each sensor of the array can be addressed (e.g., read) separately from other sensors in the array. Each sensor can have one or more electrodes for measuring the electronic signature. Examples of electrodes and electrode configurations that may be employed for use with sensors of the present disclosure are provided in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which applications is entirely incorporated herein by reference for all purposes.

In some embodiments, a biological species can be a molecular species such as biomolecule, with non-limiting examples that include polynucleotides, polypeptides, proteins, carbohydrates and fatty acids. In some examples, the biological species is a nucleic acid, including any type of nucleic acid described elsewhere herein. In some embodiments, the nucleic acid can be single stranded or double stranded. In some examples, the nucleic acid is circular.

In some embodiments, the sensing array can provide a single-pass bead loading fill factor of at least about 50%, 60%, 70%, 80%, 90%, 95%, 96%, 97%, 98%, 99%, or 99.9% (i.e., the fill factor is the percentage of the array having a bead). In some embodiments, the sensing array can provide a nucleic acid sequencing read length of at least about 20 base pairs (bp), 25 bp, 30 bp, 31 bp, 32 bp, 33 bp, 34 bp, 35 bp, 40 bp, 50 bp, 100 bp, 500 bp, 1000 bp, 5000 bp, 10,000 bp, or 100,000 bp with a non-linearity of less than or equal to about 10 bases, 5 bases, 4 bases, 3 bases, 2 bases, 1 base, or 0.5 bases. The read length can be for a nucleic acid homopolymer (e.g., all A, C, T or G).

The sensing array can be part of a chip that is removable from the housing. The chip can be a single-use chip or multi-use chip. The chip can be disposable (e.g., formed of an environmentally friendly material) and/or can be reusable. The sensing array can be substantially planar.

The sensing array can provide a nucleic acid sequencing throughput of at least about 100 base pairs (bp), 500 bp, 1000 bp, 20,000 bp, or 100,000 bp, in a time period that is less than or equal to about 2 days, 1 day, 12 hours, 6 hours, 3 hours, 2 hours, 1 hour, 45 minutes, 30 minutes, 15 minutes, 10 minutes, or 5 minutes. In some cases, a sensing array can be used to perform targeted sequencing and/or whole genome sequencing.

In some situations, the device further comprises a computer processor (or other electronic logic) coupled to the sensing array. The computer processor can be programmed to receive signals from the sensing array that are indicative of a direct electrical signature of the species or reaction associated with the species.

In some cases, the sensing array is adapted for nucleic acid sequencing, proton detection, protein detection, or pathogen detection. The sensing array can be adapted for nucleic acid amplification and/or fluid enrichment.

The device can be portable such that it can be readily transported by a user or a machine. For example, the machine may be transportable on a vehicle. In some examples, the vehicle is an automobile, motorcycle, scooter, helicopter, airplane, truck, military vehicle, spacecraft, or robot.

The measured electronic signature can be an impedance or a change in impedance associated with (i) a bead adjacent to the sensor, (ii) an electrode of the sensor or (iii) a species in a fluid adjacent to the sensor. As an alternative or in addition to, the electronic signature can be a charge or a change in charge associated with (i) a bead or other type of particle adjacent to the sensor, (ii) an electrode of the sensor or (iii) a species in a fluid adjacent to the sensor. As an alternative or in addition to, the electronic signature can be a conductivity or a change in conductivity associated with (i) a bead or other type of particle adjacent to the sensor, (ii) an electrode of the sensor or (iii) a species in a fluid adjacent to the sensor. Various details for measuring an electronic signature can be as described in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which applications is entirely incorporated herein by reference for all purposes.

In some cases, the device is part of a system for biological detection. The system can include a single device of multiple devices. Moreover, such a system can include a single module or may include a plurality of modules. Each device can be for the same biological detection or different biological detection. The devices can be in communication with each other through any suitable type of connectivity, including, for example, wireless connectivity.

Another aspect of the present disclosure provides a method for biological detection, comprising providing a sensing device comprising a sensing array with a plurality of sensors in a housing, where at least a subset of the plurality of sensors is individually addressable, where each sensor of the plurality is adapted to directly measure an electronic signature associated with a biological species in solution, where the housing has a footprint that is less than or equal to about 250,000 (square millimeters) $mm^2$, 200,000 $mm^2$, 150,000 $mm^2$, 100,000 $mm^2$, 50,000 $mm^2$, 10,000 $mm^2$, 5,000 $mm^2$, or 1,000 $mm^2$ and where the device has a weight that is less than or equal to about 200 pounds, 175 pounds, 150 pounds, 125 pounds, 100 pounds, 75 pounds, 50 pounds, 25 pounds or 10 pounds. Next, a solution comprising the biological species can be directed to the sensing array. The solution can be directed using a fluid flow system comprising, for example, one or more pumps and/or flow actuators. In some embodiments, an electronic signature associated with the biological species or a reaction associated with the biological species can be directly measured (or via signals indicative of the electronic signature) using the sensor, as described elsewhere herein. The sensing device can be as described above or elsewhere herein.

In some cases, the sensing device can be provided on a vehicle. The vehicle can be an automobile, motorcycle, scooter, helicopter, airplane, truck, military vehicle, spacecraft, or robot. The vehicle can be moved from a first location to a second location that can be different than the first location. In some situations, while the vehicle is moving from the first location to the second location, (i) the solution is directed to the sensing array and (ii) an electronic signature associated with the biological species is directly measured using the sensor.

The device can be transportable by a user. In some situations, while the user is moving from a first location to a second location, (i) the solution is directed to the sensing array and (ii) an electronic signature associated with the biological species is directly measured using the sensor.

Control Systems

Figure 4:
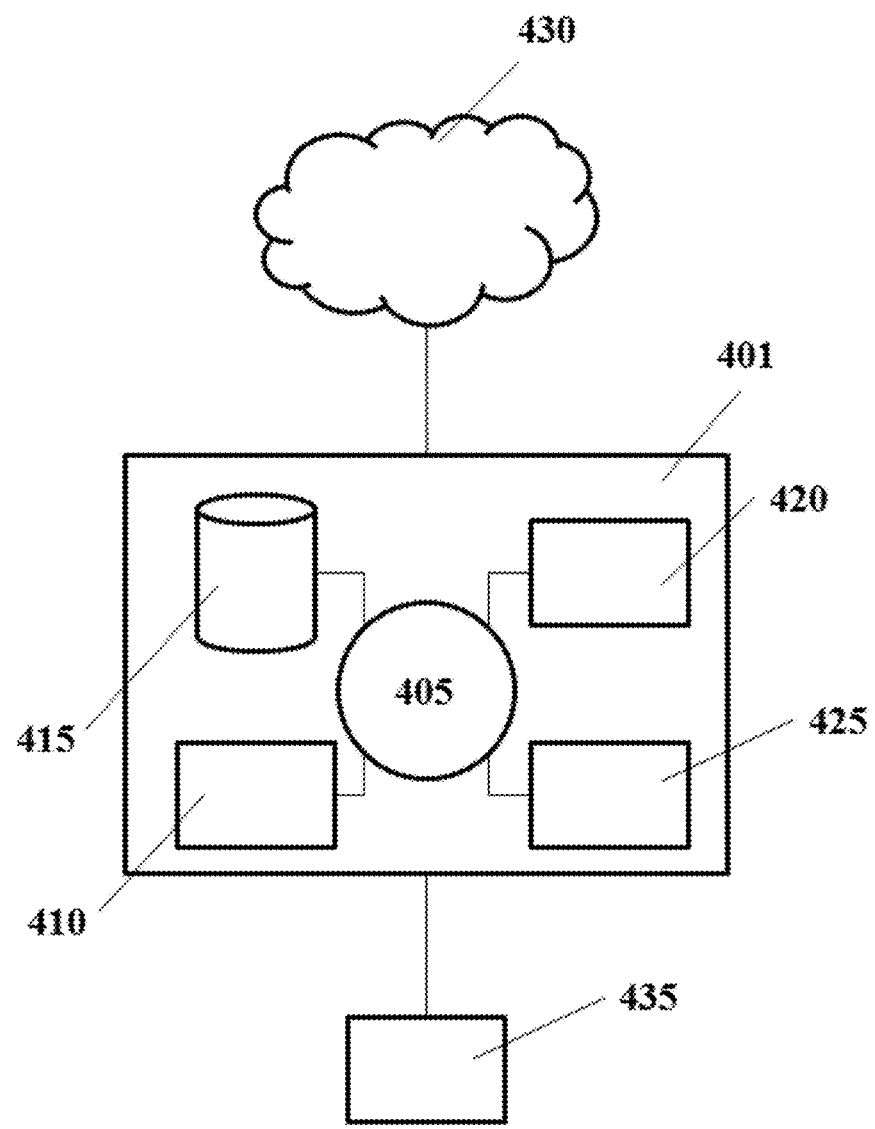
FIG. 4 shows an example computer system that is programmed or otherwise configured to control, regulate or implement devices, systems and methods of the present disclosure.

The present disclosure provides computer control systems that are programmed to implement methods of the disclosure. FIG. 4 shows a computer system 401 that is programmed or otherwise configured for biological detection. The computer system 401 can regulate various aspects of sensing devices, systems and methods of the present disclosure, such as, for example, methods for biological detection. In some embodiments, the computer system 401 can receive signals from a sensor and determine a change in local impedance, local charge and/or local conductivity as described elsewhere herein.

The computer system 401 can be part of or separate from a device or system for biological detection. In some examples, the system 401 is integrated with a device or system for biological detection, such as a nucleic acid sequencing device. For example, the system 401 can be included in a housing that also contains a sensing array, which can be provided via a removable chip.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. Examples of operations performed by the CPU 405 can include fetch, decode, execute, and writeback.

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) for providing, for example, an output or readout of a sensing device of system coupled to the computer system 401. Such readout can include a nucleic acid sequencing readout, such as a sequence of nucleic acid bases that comprise a given nucleic acid sample. Examples of UI's include, without limitation, a graphical user interface (GUI) and web-based user interface. The electronic display 435 can be a computer monitor, or a capacitive or resistive touchscreen.

Devices, methods and systems of the present disclosure can be combined with or modified by other devices, systems and/or methods, such as, for example, those described in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, each of which applications is entirely incorporated herein by reference for all purposes. These applications provide example devices and methods for directly measuring an electronic signature associated with a biological species in solution, such as impedance or charge measurement, and for making biological measurements for use in, for example, nucleic acid sequencing, including targeted sequencing and whole genome sequencing.

Multiple Sequencing Conditions

Sequencing platforms can have biases in identifying a nucleic acid sequence. A bias can arise from a number of variables, with non-limiting examples that include temperature, reagent types (e.g., buffer type, polymerase type, primer type, nucleic acid template type), nucleotide cycle order, nucleotide concentrations, material flow rates, reagent cycle time, amplification conditions and sequencer design (e.g., sensor geometry, sensor materials, surface chemistries of sequencer components such as hydrophobicity). As used herein, the term "sequencing condition" refers to a variable associated with nucleic acid sequencing that can be associated with a bias. Moreover, as used herein, the term "sequencing chemistry" refers to a sequencing condition that is associated with the chemistry of nucleic acid sequencing and generally not pertaining to sequencer design. Effects of biases arising from underlying sequencing conditions may be reduced or eliminated by the use of multiple sequencing conditions that have distinct biases. For example, various sequencing chemistries can be biased toward regions in a nucleic acid to be sequenced that are, for example, G-C rich, A-T rich, have a defined secondary structure, are homopolymeric, have palendromes, have inverted repeats, and/or have regions where a polymerase can stall or slip. In some cases, multiple sequencing conditions may introduce various sequencing biases that can be taken advantage of to improve the quality of the sequencing result as described herein.

In some cases, a post-processing algorithm can be used to combine data generated from one or more sequencing conditions in a way that accounts for the accuracy associated with each sequencing condition. For example, a post-processing algorithm may put relatively more weight where a sequencing condition is more accurate and relatively less weight where a sequencing condition is less accurate). In some cases, a post-processing algorithm may normalize effects on sequencing results attributed to sequencing conditions. Moreover, in some embodiments, base calling algorithms may be customized, calibrated and/or trained based on known biases associated with different sequencing conditions. In this manner, data generated from the different sequencing conditions may be more accurate. Additional post processing base calls from considering one or more sequencing conditions may be used to further refine results.

In some cases, data associated with a plurality of sequencing conditions applied to the same sample may be analyzed in order to generate a final data set. The final data set, which is a product of various data sets from various sequencing conditions, can be more accurate, may include longer read lengths and may have generally higher base calling scores than any of the individual data sets. For example, if a particular sequencing chemistry is poor in one region of a genome it may lead to low quality scores for the bases called in that region. Conversely, another sequencing chemistry may lead to higher quality scores in the same region. If the sequencing platform is capable of generating both data sets, this information can be taken into account during genome assembly to weight the higher quality reads over the lower quality ones. In some cases, multiple sequencing conditions can be used to identify methylated nucleic acid bases.

In one aspect, the disclosure provides a method for a method for characterizing a biological molecule or a biological reaction associated with the biological molecule. The method comprises: (a) in a first solution, coupling the biological molecule to the Debye layer of a plurality of electrodes such that the plurality of electrodes and the biological molecule provide an electrical current flow path for detecting a signal indicative of the biological molecule or the biological reaction; (b) detecting the biological molecule or the biological reaction using the plurality of electrodes in the first solution; (c) replacing the first solution with a second solution, where the first solution is different than the second solution with respect to at least one of a type of polymerase, a concentration of the polymerase, a type of ion(s) and a concentration of the ion(s); and (d) in the second solution, detecting the signal indicative of the biological molecule or the biological reaction using the plurality of electrodes.

In some cases, the method further comprises repeating (c) and (d). Additionally, the first solution can have a different temperature, pressure, and/or composition than the second solution. In some cases, the method further comprises using one or more computer processors to analyze a first data set associated with the detecting in (b) and a second data set associated with the detecting in (d) to arrive at a characterization of the biological molecule or the biological reaction. The characterization can comprise one or both of identifying or sequencing the biological molecule; and quantifying the amount of the biological molecule or the extent of the biological reaction.

In some cases, detecting in the first solution has a higher quality bias than detecting in the second solution. In such cases, an associated analysis of the first data set and the second data set may provide relatively more weight to the detection associated with the higher quality bias. Moreover, the higher quality bias can have greater accuracy than other biases with respect to detecting the biological molecule or the biological reaction than other biases.

Furthermore, the biological molecule may be attached to a bead, optionally through a linker (e.g., a linker covalently or non-covalently attached to the bead). In some cases, the biological molecule is a nucleic acid molecule and the method may further comprise sequencing the nucleic acid molecule. In some cases, the plurality of electrodes comprises at least two electrodes. In some cases, the plurality of electrodes may be exposed to the first solution and second solution.

In another aspect, the disclosure provides a method for characterizing a biological molecule or a biological reaction associated with a biological molecule. The method comprises: (a) distributing a plurality of biological molecules into an array of sensors comprising at least a first sub-set and a second sub-set of sensors, where each sensor comprises a plurality of electrodes for detecting a signal indicative of a biological molecule or a reaction associated with the biological molecule; (b) directing a first solution to the first sub-set of sensors and using the plurality of electrodes of each sensor of the first sub-set of sensors to detect signals indicative of a first sub-set of the biological molecules or a reaction associated with the first sub-set of the biological molecules in the first subset of sensors; and (c) directing a second solution to the second sub-set of sensors and using the plurality of electrodes of each sensor of the second sub-set of sensors to detect signals indicative of a second sub-set of the biological molecules or a reaction associated with the second sub-set of the biological molecules in the second subset of sensors, where the second solution is different than the first solution.

In some cases, the method further comprises repeating (b) and/or (c) with one or more additional solutions. In some cases, (b) and (c) are performed simultaneously. Additionally, the first solution can have a different temperature, pressure, and/or composition than the second solution. In some cases, the method further comprises using one or more computer processors to analyze a first data set associated with the detecting in (b) and a second data set associated with the detecting in (c) to arrive at a characterization of the biological molecule or the biological reaction. The characterization can comprise one or both of identifying or sequencing the biological molecules; and quantifying the amount of the biological molecule or the extent of the biological reactions.

In some cases, detecting in the first solution has a different bias than detecting in the second solution and an associated analysis of the first data set and the second data set gives relatively more weight to the detection associated with the higher quality bias. The higher quality bias can be more accurate when detecting the biological molecules or the biological reactions than other biases. In some cases, the first sub-set of sensors has a different bias than the second sub-set of sensors, and the one or more computer processors give relatively more weight to the detection associated with the higher quality bias.

In some cases, the biological molecules are attached to beads. Moreover, the biological molecules can be nucleic acid molecules and the method may further comprise sequencing the nucleic acid molecules. In some cases, the first sub-set of sensors have different geometries or materials of construction than the second sub-set of sensors. In some cases, the method further comprises detecting the biological molecule or the biological reaction using at least 2, at least 3, at least 4, at least 5, at least 6, at least 7, at least 8, at least 9, at least 10, at least 15, at least 20 or more sub-sets of sensors, each having a different geometry or material of construction. In some embodiments, the plurality of electrodes comprises at least two electrodes and/or may be exposed to the first solution and second solution.

In another aspect, the disclosure provides a method for sequencing a nucleic acid molecule. The method comprises (a) positioning a nucleic acid molecule adjacent to a sensor having at least two electrodes such that the at least two electrodes are electrically coupled to a Debye layer having at least a portion of the nucleic acid molecule, thereby providing an electrical current flow path for detecting a signal(s) indicative of the nucleic acid molecule or complement thereof; (b) subjecting the nucleic acid molecule to a primer extension reaction under at least two different reaction conditions that are selected for a sequencing bias selected from the group consisting of G-C bias and A-T bias; and (c) using the sensor to detect the signal(s) during the primer extension reaction, thereby sequencing the nucleic acid molecule at an accuracy of at least about 75%, at least about 80%, at least about 85%, at about 90%, at least about 95%, at least about 99% or more. In some cases, at least a portion of the nucleic acid molecule is electrically coupled to a Debye layer associated with the at least two electrodes that may be exposed to a solution having the nucleic acid molecule.

Figure 5:
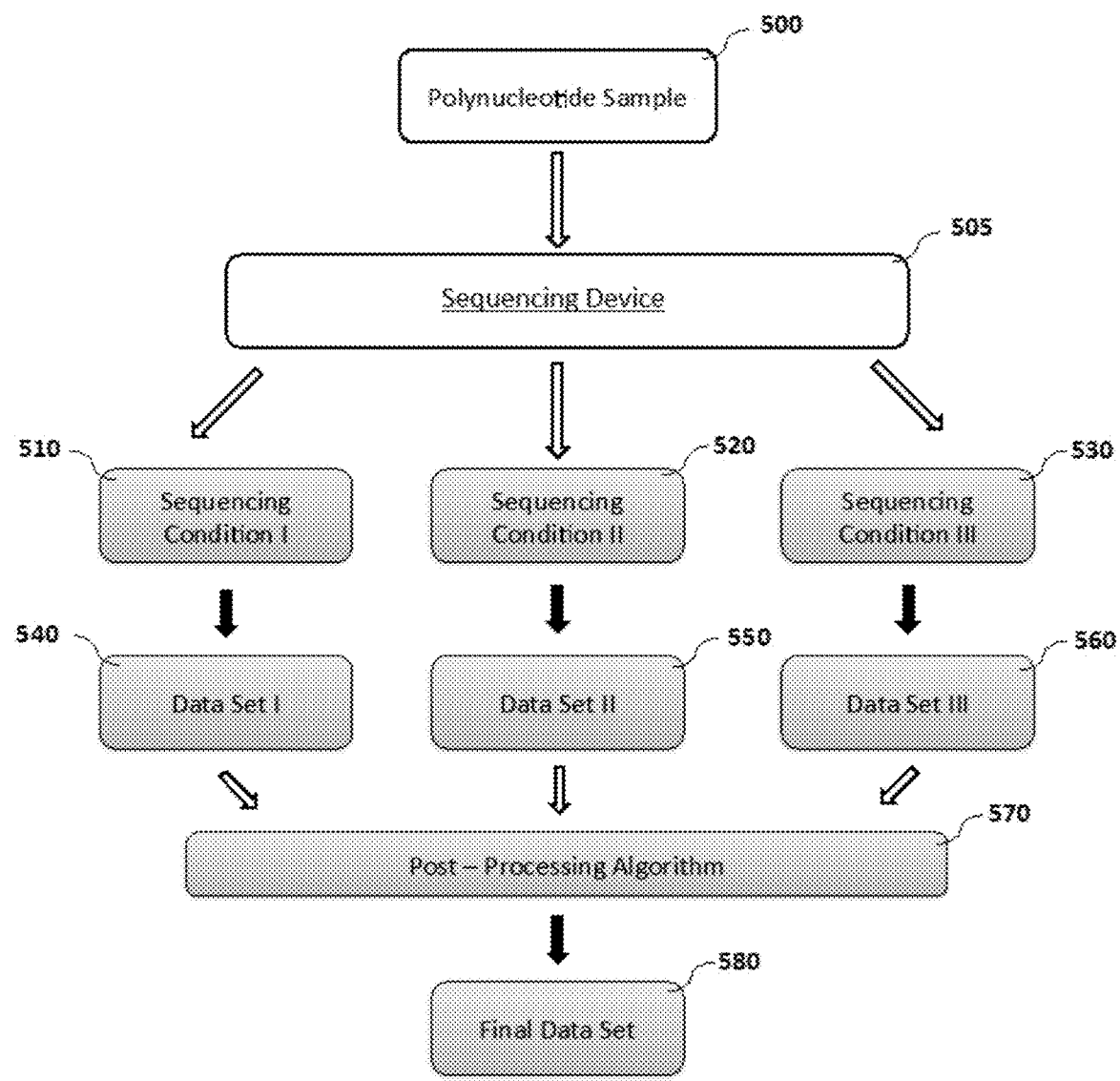
FIG. 5 shows a flow chart for an example of sequencing a sample with multiple sequencing conditions.

FIG. 5 shows, in one embodiment, a diagram showing an outline of an example sequencing process that includes analysis of sequencing data associated with multiple sequencing conditions. A polynucleotide sample 500 may be loaded in a sequencing device 505 (e.g., a high-throughput sequencing device) for sequencing analysis. The polynucleotide sample 500 may be sequenced multiple times, with a different sequencing condition being used each time. In this example, the polynucleotide sample 500 is being sequenced three times with three different sequencing conditions—Sequencing Condition I 510, Sequencing Condition II 520, and Sequencing Condition III 530. Each sequencing run and corresponding sequencing condition can yield a different data set, depending on the bias associated with each sequencing condition. In this example, Sequencing Condition I 510 yields Data Set I 540, Sequencing Condition II 520 yields Data Set II 550, and Sequencing Condition III 530 yields Data Set III 560. In this example, the resulting three data sets 540, 550 and 560 can then be analyzed using a Post-Processing Algorithm 570 that accounts for the biases in each sequencing condition. The Post-Processing Algorithm 570 can also be used to generate a Final Data Set 580. Final Data Set 580 can contain sequencing data assembled from data obtained from each sequencing condition that has a high probability of accuracy, allowing for a more accurate sequencing result.

A multiple sequencing condition method can be multiplexed (e.g., multiple lanes of an array are used for various conditions or beads with different key sequences can be loaded with different polymerases). Various sequencing conditions can be performed sequentially or simultaneously. A sample can be split into a plurality of aliquots, with each aliquot being sequenced under a different sequencing condition. Alternatively, a sample can be sequenced a plurality of times, with each sequencing being done with a different sequencing condition (e.g., recovering the bead or template after the run and adding a new primer). In some embodiments, multiple sequencing chemistries may be used to sequence the same sample. The sample may be sequenced at least two times with at least two distinct sequencing chemistries. In some cases, a sample may be sequenced with about 2, 3, 4, 5, 6, 7, 8, 9, 10, 15, 20, 50, 100 or more distinct sequencing conditions. In some embodiments, each distinct sequencing condition has a specific and/or inherent bias. In embodiments where a sample is sequenced with a plurality of sequencing conditions, one or more of the plurality of sequencing conditions may be the same sequencing condition. In some cases, all of the sequencing conditions of the plurality of sequencing conditions may be different.

Figure 6:
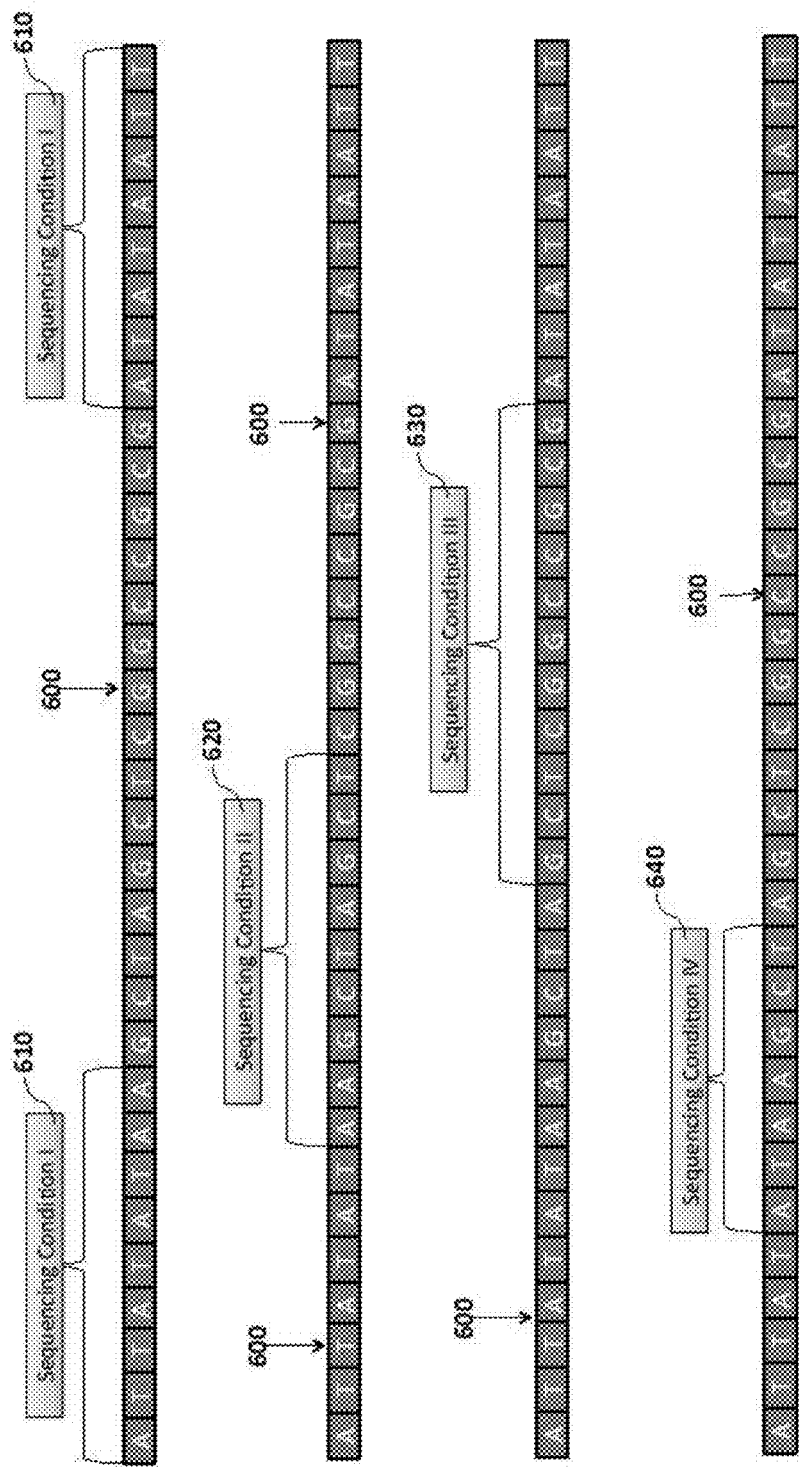
FIG. 6 shows an example of sequencing a polynucleotide sample with four sequencing conditions (SEQ ID NOS 1, 1, 1 and 1, respectively, in order of appearance)

In an example, FIG. 6 shows a sample nucleic acid sequence 600 that is sequenced with four different sequencing conditions. Each sequencing condition can be associated with a bias (e.g., an inherent bias) and may be more accurate in a particular region(s) of the sample nucleic acid sequence 600. In this example Sequencing Condition I 610 is more accurate (e.g., having accuracy of at least 70%, 75%, 80%, 85%, 90%, 95%, 99% or more) in A-T rich regions (shown in brackets). Sequencing Condition II 620 is more accurate (e.g., having accuracy of at least 70%, 75%, 80%, 85%, 90%, 95%, 99% or more) in a region where a polymerase is prone to slippage. Sequencing Condition III 630 is more accurate (e.g., having accuracy of at least 70%, 75%, 80%, 85%, 90%, 95%, 99% or more in G-C rich regions). Sequencing Condition IV 640 is more accurate (e.g., having accuracy of at least 70%, 75%, 80%, 85%, 90%, 95%, 99% or more) in a region where a polymerase is prone to stalling. In some embodiments, one sequencing condition may be more accurate in multiple regions of a sample nucleic acid sequence that are of the same type. For example, as shown in FIG. 6, Sequencing Condition I 610 is more accurate in the two A-T rich regions on the sample nucleic acid sequence 600. In some cases, one sequencing chemistry is more accurate in more than one type of region.

In some cases, after sequencing runs from various sequencing conditions is complete, a post-processing algorithm, which may be executable by a computer processor, can be used to analyze sequencing data. A final data set can be constructed based on portions of data gathered from each sequencing run. In some cases, some runs are excluded, such as in cases where the post-processing algorithm recognizes errors, determines a substantial anomaly in sequencing data or determines that a data set is not accurate in a given region based on the particular sequencing condition used to generate the date. Accordingly, portions of data gathered from each run that are used in the final data set can be selectively chosen by the algorithm based on the probability of quality (e.g., accuracy) of a given sequencing condition in a given run for a specific region of the sample nucleic acid sequence 600. Thus, in this example, data from Sequencing Condition I 610 can be used for the A-T rich region of the sample nucleic acid sequence 600 (shown in brackets); data from Sequencing Condition II 620 can be used for the region of the sample nucleic acid sequence 600 where a polymerase is prone to slippage; data from Sequencing Condition III 630 can be used for the G-C region of the sample nucleic acid sequence 600; and data from Sequencing Condition IV 640 can be used for the region of the sample nucleic acid sequence 600 where a polymerase is prone to stalling. Data obtained from each portion can then be combined to generate a final sequencing result. In some embodiments, the regions of the sample nucleic acid sequence 600 analyzed by different sequencing conditions can overlap (as shown in FIG. 6), or may not overlap.

Different sequencing conditions can be varied in any suitable way. In some cases, the device has sensors of various design and/or materials of construction that have various biases. In some cases, a plurality of sensors of the same design are used with various other sequencing conditions.

Figure 7:
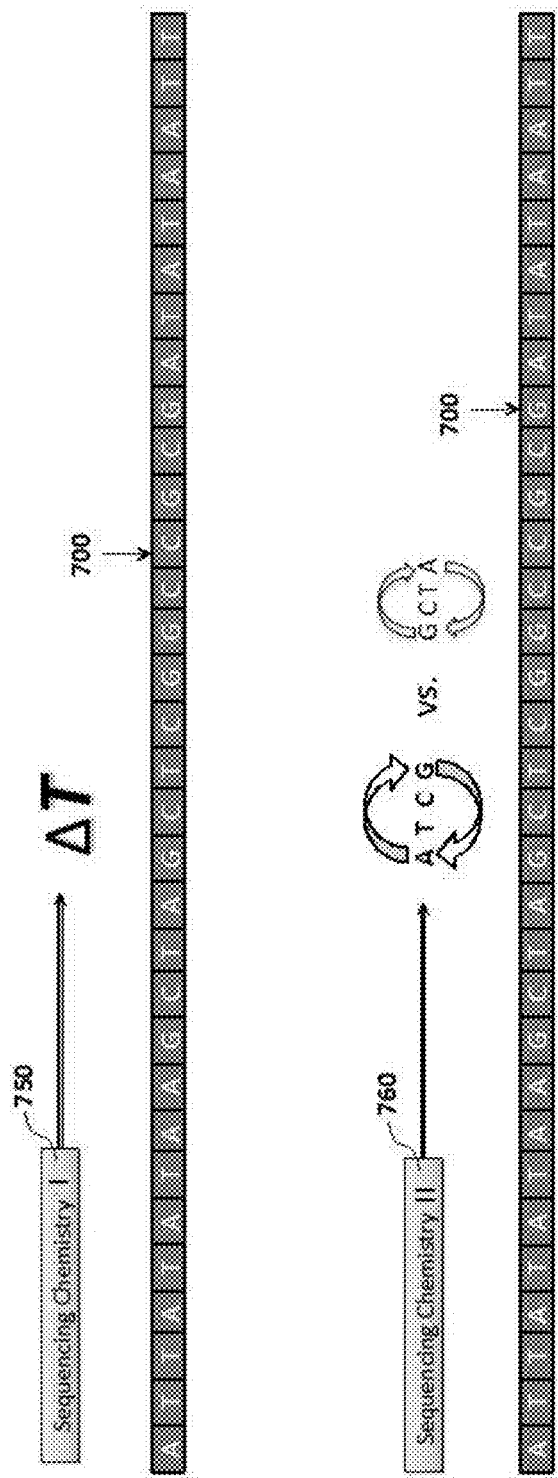
FIG. 7 shows an example of sequencing a polynucleotide sample with a plurality of conditions, such as various temperatures, or various orders or cycle times of nucleotide addition (SEQ ID NOS 1 and 1, respectively, in order of appearance)

FIG. 7 schematically depicts example sequencing chemistries that may be used. A nucleic acid strand 700 can be sequenced multiple times using various groups of sequencing chemistries, and/or several copies of the nucleic acid strand 700 can be sequenced using various groups of sequencing chemistries. The group Sequencing Chemistry I 750 includes various temperatures for nucleotide incorporation, with which temperature is varied to generate different sequencing conditions. The group Sequencing Chemistry II 760 includes various orders of nucleotide additions (e.g. A, T, C, G versus G, T, A, C and other permutations of A, T, C, G nucleotide order, etc.). The cycle time of the nucleotides can be varied, in addition to, or instead of varying the order of nucleotides. For example the time between addition of any two nucleotides can be lengthened or shortened.

In some cases, sequencing chemistries can be distinguished by nucleotide incorporation temperature. For example, a nucleotide incorporation temperature may be at least about 10° C., 15° C., 20° C., 30° C., 40° C., 50° C., 60° C., 70° C., 80° C., 90° C., 95° C., 100° C., 105° C., 110° C., or 120° C. In some cases, the difference in temperature between various sequencing chemistries is not large. For example, two nucleotide incorporation temperatures can vary by at most about 0.01° C., 0.05° C., about 0.1° C., about 0.5° C., about 1.0° C., about 1.5° C., about 2.0° C., about 2.5° C., about 3.0° C., about 3.5° C., about 4.0° C., about 4.5° C. or about 5° C. In some cases, multiple nucleotide incorporation temperatures or a nucleotide incorporation temperature gradient can be employed throughout a sequencing reaction. For example, each nucleotide incorporation cycle may start at a first temperature (e.g., 30° C.) and ramp to a second temperature (e.g., 50° C.) before switching to a new nucleotide. The ramp may be continuous over time, may comprise discrete temperature steps or may be a combination of the two.

In some cases, pressure at which a sequencing reaction takes place can be varied to generate multiple sequencing conditions. For example, pressure associated with a sequencing reaction may be varied between 15 atmospheres (atm) and 0.01 atm; between 10 atm and 0.1 atm; between 10 atm and 1 atm; 8 atm and 1 atm; and 5 atm to 1 atm.

In some embodiments, a sequencing chemistry may be made distinct by altering the order of nucleotide addition. For example, in one sequencing chemistry the order of nucleotide addition may be: A, T, C, and G. As part of the sample example, in another sequencing chemistry, the order of nucleotide addition may be G, T, A, and C. In some cases, when a base cycles through that is not the correct base pair at a given point in the sequence, known as a zero base challenge, there is a chance of misincorporation. As such, each base cycle order may have a slightly different bias. In some cases, the base cycle does not repeat through every possible base in a nucleotide set (e.g., A, T, A, T, G, C, G, C).

In some embodiments, a sequencing chemistry may be changed by altering the composition of incorporation buffer or detection buffer. In some embodiments, the incorporation buffer or detection buffer may have monovalent ions. In some embodiments, the incorporation or detection buffer may have divalent ions. Non-limiting examples of incorporation and/or detection buffers include phosphate buffer, bicarbonate buffer, Tris buffer, HEPES buffer, tricine, histidine, EPPS buffer, triethanolamine, citrate, glycine and mixtures thereof. Moreover, an incorporation buffer or detection buffer can include a surfactant, a denaturant (e.g., betaine or urea), dimethylsulfoxide (DMSO), ethanol or other organic solvent.

In some embodiments, a sequencing chemistry may be altered by changing the concentration of nucleotides that are inputted into the sequencing system and/or the incorporation times. In some embodiments, sequencing may be performed with various concentrations of nucleotides. For example, sequencing may be performed with a nucleotide concentration of least about 0.1 micromolar ($\mu M$), 0.5 $\mu M$, 1 $\mu M$, 5 $\mu M$, 10 $\mu M$, 20 $\mu M$, 50 $\mu M$, 100 $\mu M$, 150 $\mu M$, 200 $\mu M$, 500 $\mu M$, 1000 $\mu M$ or more. For example, sequencing may be performed with a nucleotide concentration of at most about 0.1 $\mu M$, 0.5 $\mu M$, 1 $\mu M$, 5 $\mu M$, 10 $\mu M$, 20 $\mu M$, 50 $\mu M$, 100 $\mu M$, 150 $\mu M$, 200 $\mu M$, 500 $\mu M$ or 1000 $\mu M$. In some cases, the concentration of any two nucleotides used for sequencing is not the same. Moreover, in some cases, different ratios of nucleotides can be used. For example, in one run 20 $\mu M$ of A is used and 2000 $\mu M$ of T, C, and G are used. In another run, for example, 50 $\mu M$ of T and A is used and 1000 $\mu M$ of G and C is used. Any permutation of concentrations and ratios among the various nucleotides used for sequencing can be used.

In some cases, multiple sequencing chemistries may be used to sequence various portions of a sample. In other embodiments, multiple sequencing chemistries may be used to sequence the whole sample. In some embodiments, the sample may be sequenced such that different portions of the sample are subjected to different sequencing chemistries (e.g., performed in one run or across multiple runs). There may be just one sequencing run for each portion, or more than one sequencing run with the same or different sequencing chemistry. In some embodiments, there may be more than one sample that is sequenced, depending on the capabilities of the sequencing device and/or method used.

Figure 8:
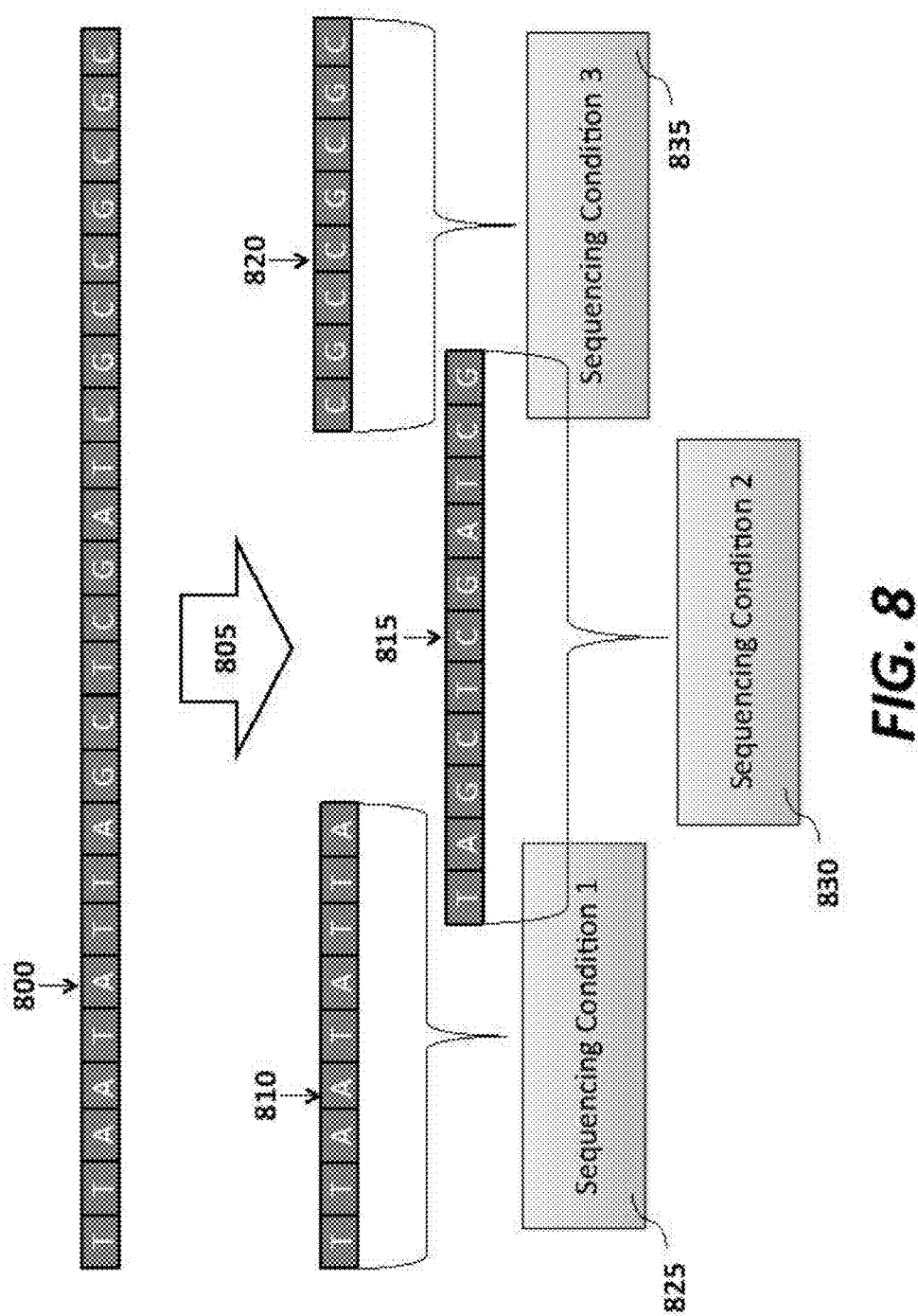
FIG. 8 shows an example of fragmenting a polynucleotide sample to generate fragments, and sequencing the fragments with a plurality of sequencing conditions (SEQ ID NOS 2 and 3, respectively, in order of appearance)

In some cases, a nucleic acid to be sequenced can be fragmented and the resulting fragments each sequenced using a given sequencing conditions. The data obtained from sequencing each fragment can be analyzed and analyses combined/weighted to determine a sequence for the original nucleic acid, as described elsewhere herein. FIG. 8 schematically depicts an example method, where a nucleic acid is fragmented and the resulting fragments sequenced using different sequencing conditions. As shown in FIG. 8, a sample nucleic acid sequence 800 is split 805 into three fragments 810, 815 and 820 encompassing three different regions. In some embodiments, the sequence of the nucleic acid fragments may overlap (as shown) or they may not overlap. Each fragment may then be sequenced using a different sequencing condition that is optimized for that region. In this example, Sequencing Condition 1 825 is more accurate (e.g., having accuracy of at least 70%, 75%, 80%, 85%, 90%, 95%, 99% or more) in A-T rich regions (shown in brackets) and thus is used to sequence nucleic acid fragment 810, an A-T rich region of sample nucleic acid sequence 800. Sequencing Condition 2 830 is more accurate (e.g., having accuracy of at least 70%, 75%, 80%, 85%, 90%, 95%, 99% or more) where a polymerase is prone to slippage and thus is used to sequence nucleic acid fragment 815, a region of sample nucleic acid sequence 800 where polymerase tends to slip. Sequencing Condition 3 835 is more accurate (e.g., having accuracy of at least 70%, 75%, 80%, 85%, 90%, 95%, 99% or more) in G-C rich regions and thus is used to sequence fragment 820, a G-C rich region of sample nucleic acid sequence 800. The results from these three runs may then combined and analyzed by a post-processing algorithm. Via the data combination and analysis, a final sequence for sample nucleic acid sequence 800 can be determined.

Figure 9:
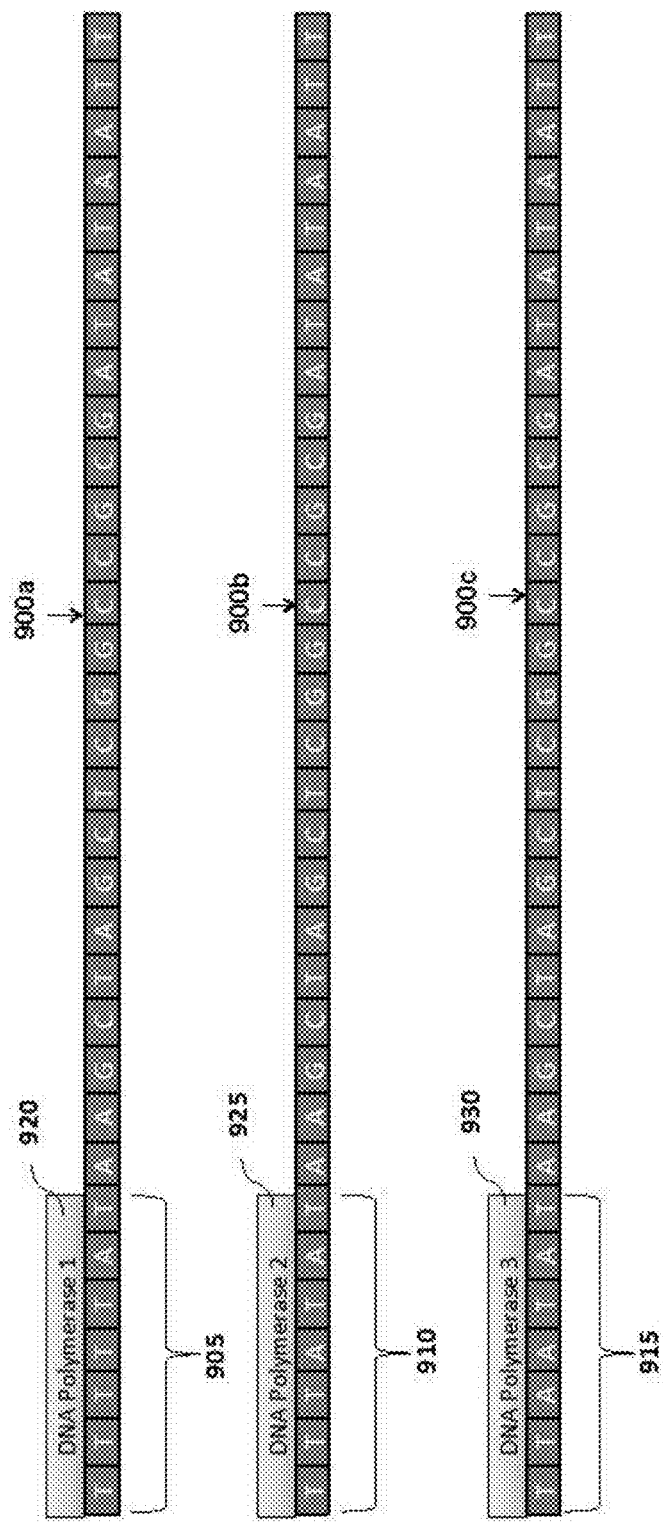
FIG. 9 shows an example of appending three different sequences to a polynucleotide sample to load, and sequence with, three different polymerases (SEQ ID NOS 4-6, respectively, in order of appearance)

In some cases, different sequencing chemistries can include the use of different polymerases, an example of which is schematically depicted in FIG. 9. As shown in FIG. 9, three variations 900a, 900b and 900c of a sample nucleic acid sequence are shown, each having a 5' region (905, 910 or 915) that has a different sequence in its first four nucleotide bases. Each of these different sequences binds a different polymerase 920, 925, and 930. Each variation 900a, 900b and 900c is sequenced using its respective polymerase. The sequencing data from each variation 900a, 900b and 900c is then combined/analyzed to determine a sequence for the sample nucleic acid sequence. In some cases, the sample nucleic acid sequence can be modified with different polymerase binding regions (e.g., 905, 910 and 915) and then subject to sequencing with different polymerases. While the example shown in FIG. 9 shows polymerase binding sequences at the 5' end of the sample nucleic acid sequence, the polymerase binding sequence may be inserted or naturally present at any location along the sample nucleic acid strand. Moreover, in some cases, a sample nucleic acid sequence may comprise and may be modified to comprise multiple polymerase binding sequences that each binds a different polymerase. Sequencing can then proceed along different locations of the sample nucleic acid sequence.

A polymerase used in conjunction with multiple sequencing chemistries include, without limitation, polymerases isolated from *Thermus aquaticus*, polymerases isolated from *Thermus thermophilus*, polymerases isolated from *Pyrococcus woesei*, polymerases isolated from *Pyrococcus furiosus*, polymerases isolated from *Thermococcus litoralis*, polymerases isolated from *Thermotoga maritime*, *E. coli* DNA polymerase, the Klenow fragment of *E. coli* DNA polymerase, T4 DNA polymerase, T7 DNA polymerase, *E. coli*, T7, T3, SP6 RNA polymerases and AMV, M-MLV and HIV reverse transcriptases. In some cases, a given polymerase (e.g., T4 DNA polymerase) is genetically engineered to have an altered bias (e.g., and various mutants of the polymerase constitute different sequencing chemistries).

In some embodiments where beads or particles are employed, the beads or particles may be "barcoded" such that different populations of beads or particles can be tracked. For example, a specific first population of beads or particles is linked to a first primer, whereas a second population of beads or particles is linked to a second primer. In some cases, bias due to use of a different polymerase may be tracked by associating a specific polymerase with a particular set of barcoded beads or particles. For example, a specific first population of beads or particles barcoded with a first primer can be associated with a first polymerase, whereas a second population of beads or particles barcoded with a second primer can be associated with a second polymerase. In some cases, there may be at least about 1, 2, 3, 5, 10, 20, 50, 100, 500, 100, 1000, or more populations of barcoded beads or particles. As an alternative to or in conjunction with barcoded beads or particles, a surface (e.g., a surface of a sensor array, a surface of a sensor, etc.) may be barcoded and marked as a specific population.

Sequencing methods described herein can provide for improved sequencing in terms of accuracy and read-length capabilities. For example, by sequencing using sequencing conditions selected to account for various sequencing bias, sequencing accuracies of at least about 70%, 75%, 80%, 85%, 90%, 95%, 99% or more can be achieved over read lengths of at least about 100 bases, 200 bases, 300 bases, 400 bases, 500 bases, 1 kilobase (kb), 2 kb, 3, kb, 4 kb, 5 kb, or even 10 kb. This may be employed in conjunction with parallel sequencing (e.g., using an array of sensors) to provide sequencing redundancy, which can provide for high accuracy and high throughput sequencing of a nucleic acid molecule.

In some embodiments, a sample nucleic acid sequence may be sequenced using various methods including, but not limited to, sequencing by synthesis, chemical ligation, shotgun sequencing, pyrosequencing, sequencing using fluorescent dyes, chemiluminescent detection, nanopore sequencing, and real-time single molecule sequencing.

Fluidic Systems and Methods

Sequencing methods and operation of sequencing systems described herein can include exposing a sensor array to a variety of fluids in succession, including fluids comprising sequencing reagents (e.g., polymerase, primers, nucleotides). In some cases, the fluids are not contaminated by each other (e.g., nucleotide solution containing A does not also contain G, C or T). The present disclosure provides systems and methods that also reduce the amount of time between fluid exchanges and reduce the amount of fluid consumed.

Described herein are systems and methods for delivering a plurality of fluids to a sensor array. In one aspect, the disclosure provides a system for delivering a plurality of fluids to a sensor array for processing or analyzing a biological sample. The system comprises: (a) a plurality of reservoirs, each reservoir adapted to contain a separate reagent; (b) a sensor array in fluidic communication with each of the reservoirs by way of an individual reagent channel fluidically connecting each reservoir to the sensor array, where the sensor array comprises individual sensors each having at least two electrodes that, during use, are electrically coupled to a Debye layer associated with the biological sample; (c) a wash channel in fluidic communication with each individual reagent channel and a wash reservoir; (d) a plurality of pneumatic channels adapted to individually adjust a pressure of each of the plurality of reservoirs; and (e) a plurality of valves on any combination of the individual reagent channels and the wash channels, where the plurality of pneumatic lines and the plurality of valves are configured to deliver a given reagent from a given one of the plurality of reservoirs to the sensor array without contamination from other reagents in a remainder of the plurality of reservoirs. In some cases, the plurality of pneumatic channels are pressurized such that the wash channels have a higher pressure than the individual reagent channels.

In some cases, the system further comprises a waste channel in fluidic communication with each individual reagent channel and a waste reservoir. In some cases, the sensor array is capable of detecting nucleic acid sequencing reactions. In some cases, the reservoirs each contain one or more of the nucleotides adenine, guanine, thymine and cytosine. Moreover, reagents contacting the sensor array can be changed with relatively short times. For example, the reagent contacting the sensor array can be changed in less than about 30 seconds, in less than about 25 seconds, in less than about 20 seconds, in less than about 15 seconds, in less than about 10 seconds, in less than about 7 seconds, in less than about 5 seconds, in less than about 3 seconds, in less than about 1 second or less.

In another aspect, the disclosure provides a method for delivering a plurality of fluids to a sensor array for processing or analyzing a biological sample. The method comprises: (a) injecting a first reagent from a first reservoir, through a first reagent channel into a sensor chamber comprising an array of sensors, where the array of sensors comprises individual sensors each having at least two electrodes that, during use, are electrically coupled to a Debye layer associated with the biological sample; (b) detecting a first signal from the array of sensors in the presence of the first reagent; (c) injecting a first wash fluid through a first wash channel, which first wash channel intersects the first reagent channel at a junction point between the first reservoir and the sensor chamber, such that the first wash fluid flows into the sensor chamber and the first wash fluid displaces at least a portion of the first reagent in the first reagent channel between the bisection point and the first reservoir; (d) injecting a second wash fluid through a second wash channel, which second wash channel intersects a second reagent channel at a junction point between a second reservoir and the sensor chamber, such that the second wash fluid flows into the sensor chamber and the second wash fluid displaces the first reagent in the second reagent channel; (e) injecting a second reagent from the second reservoir, through the second reagent channel into a sensor chamber; and (f) detecting a second signal from the array of sensors in the presence of the second reagent. In some cases, the method further comprises pressurizing the first wash channel, the second wash channel and the third wash channel to a pressure that is greater than a pressure of the first reservoir and the second reservoir.

In some cases, the method further comprises, prior to (e), injecting a third wash fluid through a third wash channel, which third wash channel intersects with a third reagent channel at a junction point between a third reservoir and the sensor chamber, such that the third wash fluid flows into the sensor chamber and the third wash fluid displaces the first reagent in the third reagent channel. Moreover, in some cases, the sensor the sensor array can detect a nucleic acid sequencing reaction of the biological sample and/or the first reagent and the second reagent may comprise different nucleotides.

Via the aid of systems described herein, time elapsed of fluidic delivery method execution can be reduced or minimized. For example, the time elapsed between (b) and (f) can be less than about 30 seconds, less than about 25 seconds, less than about 20 seconds, less than about 15 seconds, less than about 10 seconds, less than about 7 seconds, less than about 5 seconds, less than about 3 seconds or less than about 1 second.

Furthermore, in various aspects, the individual reagent channels and the wash channels can be positioned at an angle with respect to each other. For example, each of the individual reagent channels and the wash channels form an angle of at least about 5°, at least about 10°, at least about 15°, at least about 20°, at least about 25°, at least about 30°, at least about 40°, at least about 45°, at least about 50°, at least about 55°, at least about 60°, at least about 65°, at least about 70°, at least about 75°, at least about 80°, at least about 85° or at least about 89°. In some cases, each of the individual reagent channels and the wash channels form a right angle with respect to each other.

In some cases of various aspects, each of the individual reagent channels and the wash channels form a right angle with respect to the sensor array. In some cases, each of the individual reagent channels and the wash channels form an angle that is from about 10° to 90° from, from about 30° to 90°, from about 45° to 90° or from about 60° to 90° with respect to the sensor array. In some cases, each of the individual reagent channels and the wash channels form an angle that is about 5°, at least about 10°, at least about 15°, at least about 20°, at least about 25°, at least about 30°, at least about 40°, at least about 45°, at least about 50°, at least about 55°, at least about 60°, at least about 65°, at least about 70°, at least about 75°, at least about 80°, at least about 85° or at least about 89° with respect to the sensor array.

Figure 10:
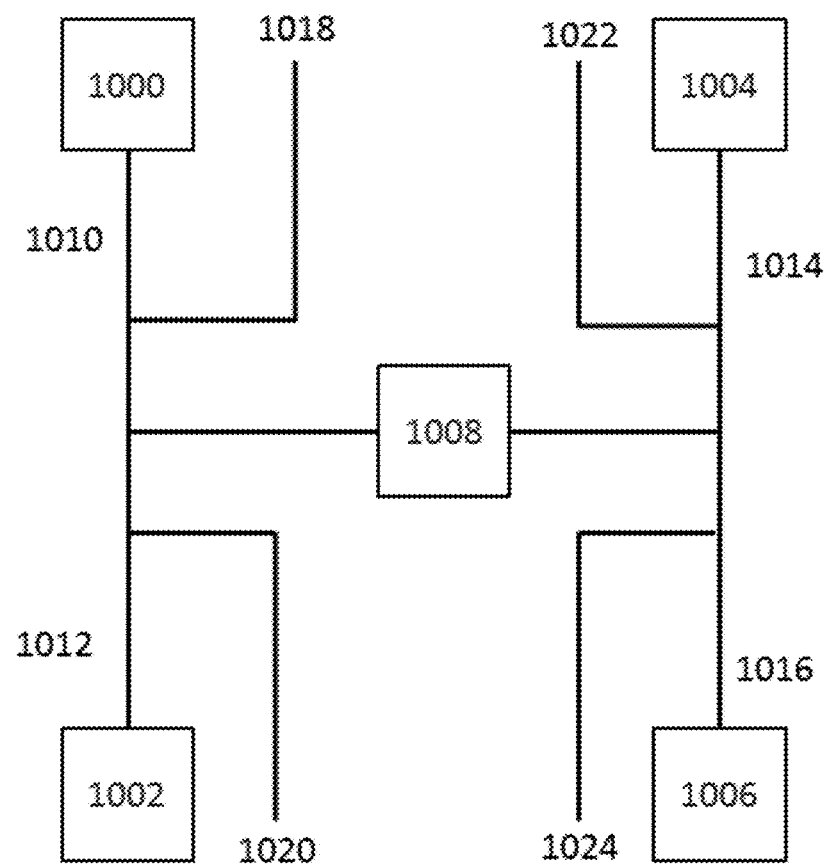
FIG. 10 shows an example of a fluidic system capable of alternately flowing reagents into a sensor chamber.

An example system configuration is schematically depicted in FIG. 10. With reference to FIG. 10, the system can comprise a plurality of reservoirs (e.g., 1000, 1002, 1004, and 1006 in FIG. 10), where each reservoir can be adapted to contain a separate reagent (e.g., a solution comprising one of the nucleotides A, T, G and C). While only four reagent reservoirs are shown in FIG. 10, FIG. 10 is not meant to be limiting. The system can include any suitable number of reservoirs. The reagents can be delivered to a sensor array 1008, such as a sensor array described herein, in an alternating fashion (e.g., to perform sequencing by synthesis) without cross-contamination of the reagents.

With continued reference to FIG. 10, the sensor array can be in fluidic communication with each of the reservoirs by way of an individual reagent line connecting each reservoir to the sensor array (e.g., 1010, 1012, 1014 and 1016 in FIG. 10). Note that, as shown in FIG. 10, some of the reagent lines may meet at a junction upstream of an inlet line to the sensor array 1008. The system can also include one or more wash lines (e.g., in FIG. 10) in fluidic communication with each individual reagent line and a wash reservoir (not shown). The wash solution can be a buffer (e.g., the same or similar buffer containing the nucleotides) or other suitable liquid material. The system can also include one or more waste lines (not shown).

Moreover, the system can include one or more pneumatic lines adapted to individually adjust a pressure of each of the plurality of reservoirs 1000, 1002, 1004, and 1006. The system can also include one or more valves on any combination of the individual reagent lines 1010, 1012, 1014 and 1016, any waste lines and the wash lines 1018, 1020, 1022 and 1024. The one or more pneumatic lines and the one or more valves can be configured such that each of the separate reagents in the reagent reservoirs 1000, 1002, 1004, and 1006 can be successively delivered to the sensor array 1008 without contamination from any other reagents. In some cases, the one or more pneumatic lines are pressurized such that the wash lines 1018, 1020, 1022 and 1024 have a higher pressure than the individual reagent lines 1010, 1012, 1014 and 1016 (e.g., a difference of at least about 0.1 pound per square inch (psi), at least about 0.5 psi, at least about 1 psi, at least about 1.5 psi, at least about 2.0 psi, at least about 2.5 psi, at least about 3.0 psi, at least about 3.5 psi, at least about 4.0 psi, at least about 4.5 psi, at least about 5 psi or more).

Opening and closing valves can create a pressure shock that can have negative effects on sensors of the sensor array 1008 and/or measurements performed by the sensors. In some cases, this pressure wave can be attenuated by creating an angle in the reagent lines 1010, 1012, 1014 and 1016 and the wash lines 1018, 1020, 1022 and 1024 such that the pressure wave does not travel directly to the sensor array 1008. In some cases, each of the individual reagent lines 1010, 1012, 1014 and 1016, any waste lines and/or the wash lines 1018, 1020, 1022 and 1024 form an angle of at least about 45°, at least about 50°, at least about 55°, at least about 60°, at least about 65°, at least about 70°, at least about 75°, at least about 80°, or at least about 85°. In some cases, each of the individual reagent lines 1010, 1012, 1014 and 1016, any waste lines and/or the wash lines 1018, 1020, 1022 and 1024 form a right angle with respect to the sensor array 1008.

Figure 11A:
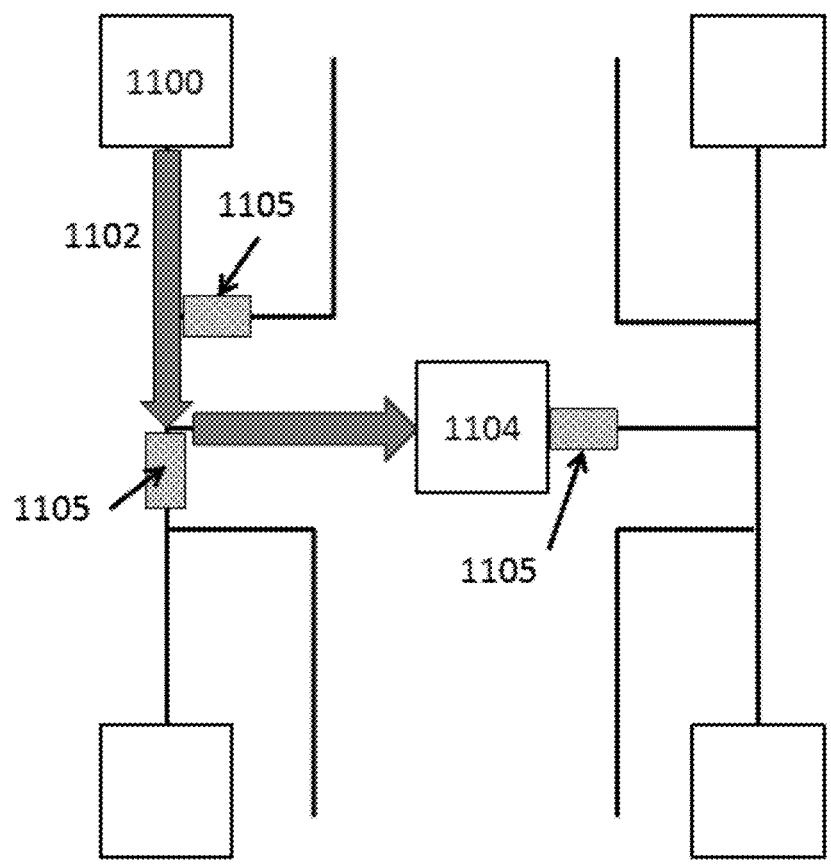
FIG. 11A-FIG. 11E show various stages of an example method for injecting reagents into a sensor chamber and washing with various wash fluids.

An example method using the system of FIG. 10 schematically depicted in FIGS. 11A-11E. With reference to FIG. 11A, the method can comprise injecting a first reagent from a first reservoir 1100, through a first reagent line 1102 and into a sensor chamber 1104 comprising an array of sensors. The method can then include deriving a first signal (e.g., indicative of an impedance change, charge change, conductivity change, ion concentration change, etc.) from the array of sensors in the presence of the first reagent. In some cases, the first reagent may not flow only in the desired path. Some of the first reagent can flow into adjoining lines through diffusion or bulk flow, as shown by textured areas 1105.

Figure 11B:
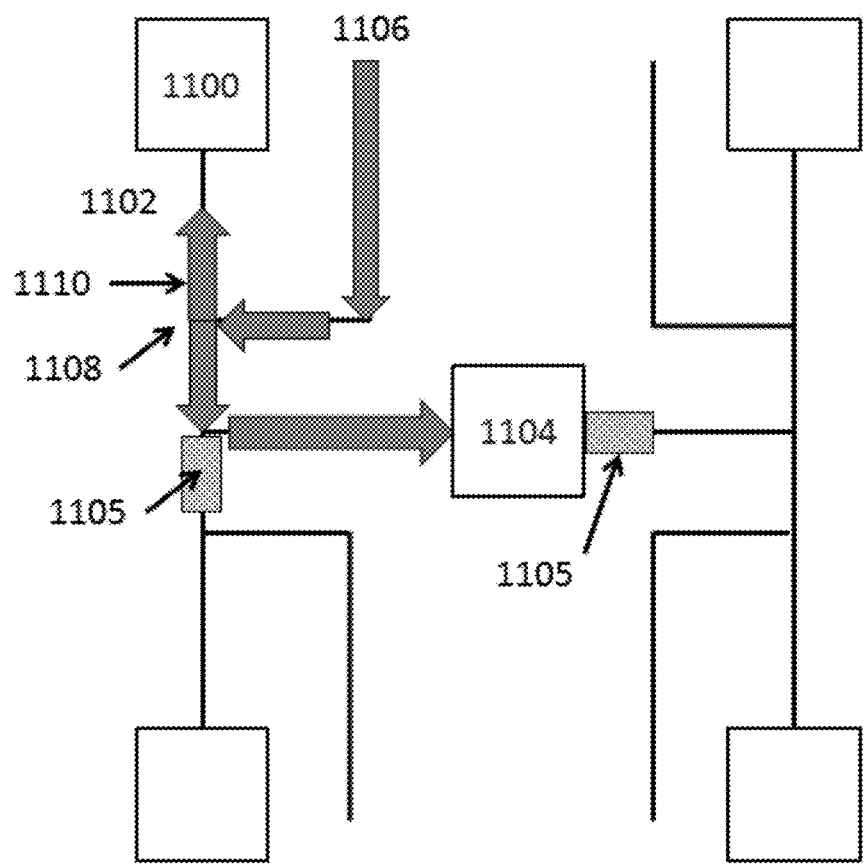

Continuing with FIG. 11B, the method can then include injecting a first wash fluid through a first wash line 1106, which first wash line combines with the first reagent line 1102 at a junction 1108 between the first reservoir 1100 and the sensor chamber 1104, such that the first wash fluid flows into the sensor chamber 1104. The first wash fluid also displaces at least some of the first reagent in the first reagent line between the junction 1108 and the first reservoir 1100 (as shown 1110).

Figure 11C:
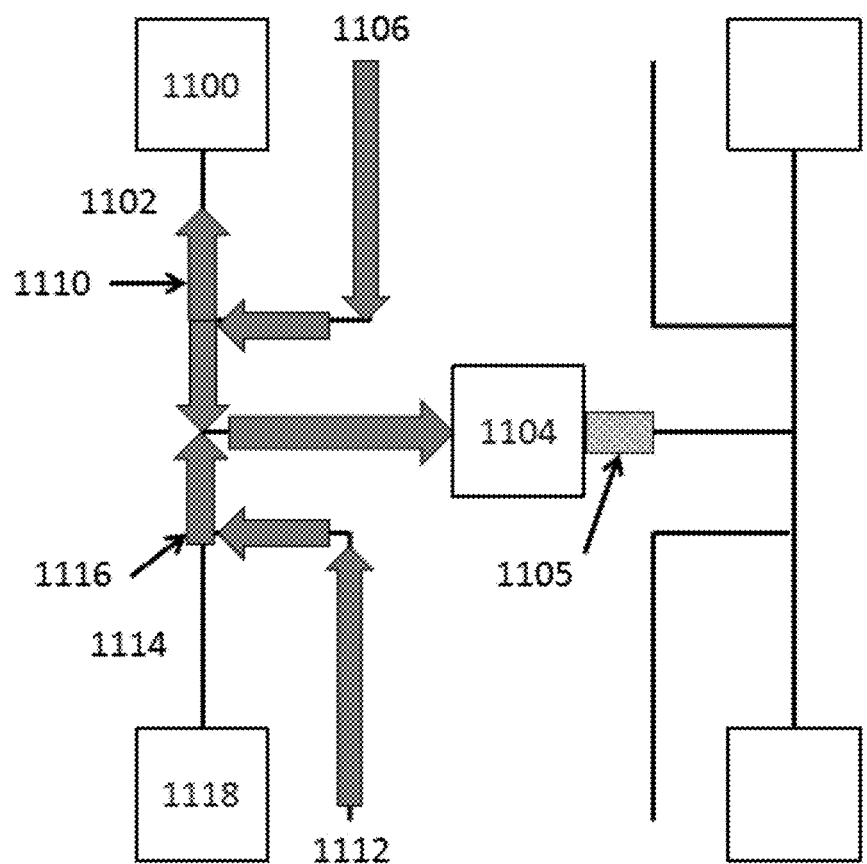

Continuing with FIG. 11C, the method can then include injecting a second wash fluid (e.g., prior to ceasing the flow of the first wash fluid) through a second wash line 1112, which second wash line combines with a second reagent line 1114 at a junction 1116 between a second reservoir 1118 and the sensor chamber 1104, such that the second wash fluid flows into the sensor chamber 1104. The second wash fluid also displaces the first reagent in the second reagent line (e.g., pushing it through the sensor chamber 1104).

Figure 11D:
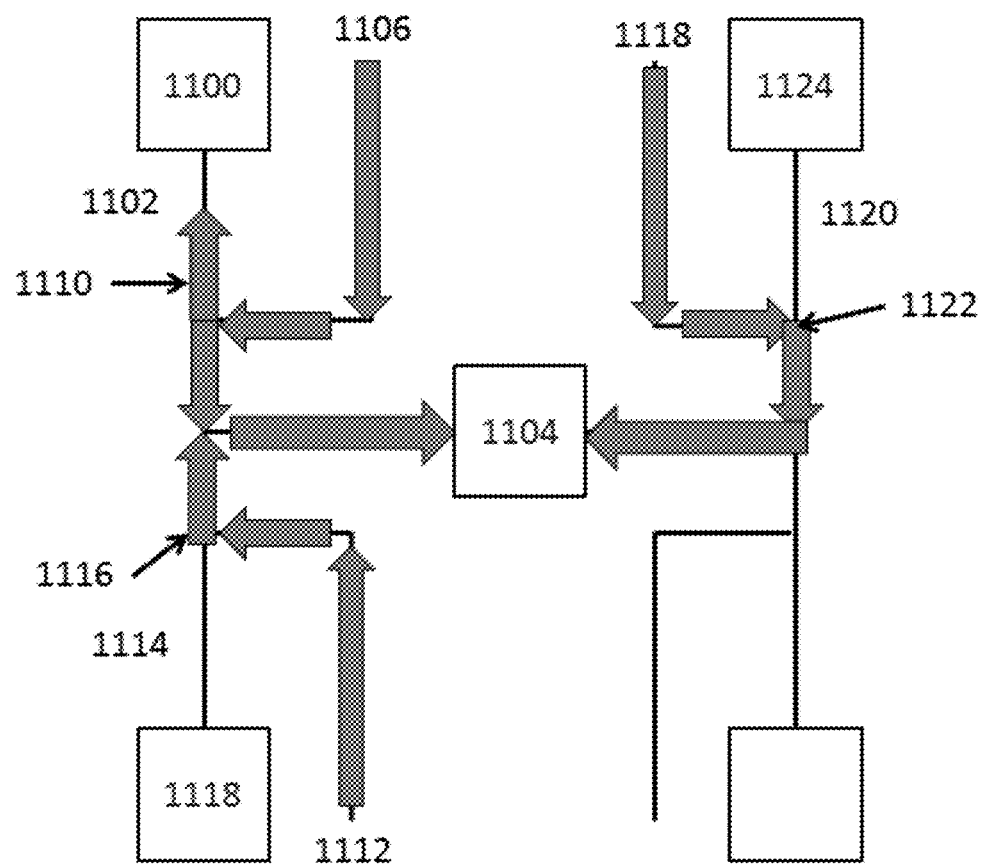

Continuing with FIG. 11D, the method can further comprise injecting a third wash fluid (e.g., prior to ceasing the flow of the first wash fluid and/or the second wash fluid) through a third wash line 1118, which third wash line combines with a third reagent line 1120 at a junction 1122 between a third reservoir 1124 and the sensor chamber 1104, such that the third wash fluid flows into the sensor chamber 1104. The third wash fluid also displaces the first reagent in the third reagent line (e.g., pushing it through the sensor chamber).

Figure 11E:
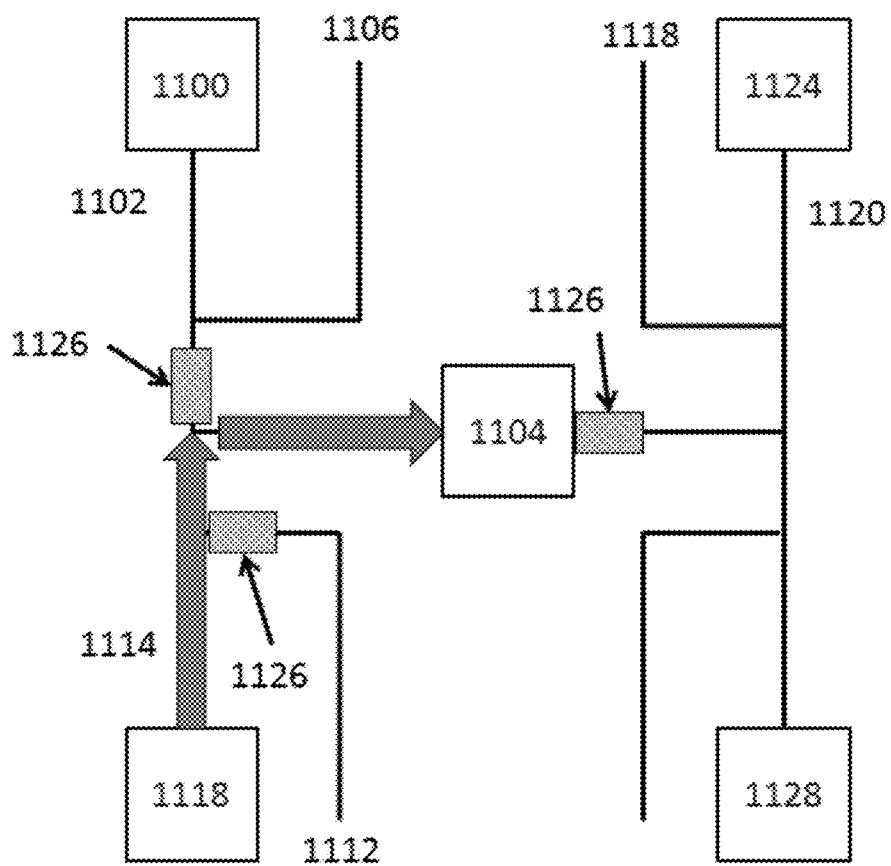

At this point, all of the residual first reagent has been flushed from the various lines and will therefore not contaminate subsequent injections of other reagents. With reference to FIG. 11E, the method can further include injecting a second reagent from the second reservoir 1118, through the second reagent line 1114 and into a sensor chamber 1104. Residual amounts of the second reagent 1126 can be deposited in adjacent channels, which can be displaced using the washing procedure described herein. As the systems shown in FIG. 10 and FIGS. 11A-E are symmetrical on two axis, the reagent supply and washing steps above can apply analogously to supply reagents from the other reagent reservoirs (e.g., 1118, 1124 and 1128 in FIG. 11E) without contamination.

Avoidance of contamination can improve the quality of sequencing data and reduce artifacts observed in sequence results. As described elsewhere herein, the fluidic systems and methods described above can avoid contamination of reagents that are supplied in succession to a sensor array, including contamination of nucleotide solutions that are applied to a sensor array as part of a sequencing by synthesis reaction For example, in some embodiments, using the system of FIG. 10 and/or the method of FIG. 11, where the reservoirs each comprise a solution of a given nucleotide (e.g., A, T, C or G), a nucleotide solution contacting a sensor array at a given point comprises at least about 85%, at least about 90%, at least about 95%, at least about 99%, at least about 99.5%, at least about 99.9%, at least about 99.95%, or at least about 99.99% of the desired nucleotide compared to the concentration of all nucleotides in the solution.

Moreover, as described above, the fluidic systems and methods described above can also reduce the transition time for supplying different reagent fluids to a sensor array. For example, in some embodiments, when using the system of FIG. 10 and/or the method of FIG. 11, the transition time between different reagent fluids contacting the sensor array may be less than about 45, seconds 30 s, less than about 25 s, less than about 20 s, less than about 15 s, less than about 10 s, less than about 7 s, less than about 5 s, less than about 3 s, less than about is or less.

Kinematic Mount Sensors

The devices, systems and methods described herein can include or include the use of a sensor to detect a change of impedance, change of conductivity, change of ion concentration and/or change of charge associated with the incorporation of a nucleotide onto a growing nucleic acid (e.g., during a sequencing reaction). The nucleic acid can be associated with a bead and the sensor can be electrically coupled to (e.g., within) the Debye layer of the bead or nucleic acid coupled to the bead. The sensor can comprise at least two electrodes and a securing member (e.g., a magnet), which can hold the bead at an appropriate position relative to the electrodes. In addition to the securing member, it may be helpful to further secure a bead at its appropriate position. In such cases, a kinematic mount (abbreviated as "KM") sensor can provide further support to keep a bead in place, particularly when fluid is being flown over the sensor.

A KM sensor can prevent bead movement over its securing member, for example, due to fluid flow. In cases where the securing member is a magnet, forces associated with fluid flow may be stronger than magnetic forces holding a bead in place and induce motion of the bead. Such motion can interfere with signal acquisition, resulting in a loss in signal stability, signal inaccuracies and/or lower signal-to-noise ratios. The configuration of a KM sensor prevents bead vibrations or other types of bead motion around its securing member. In a KM sensor, a bead associated with its securing member is also in physical contact with one or more electrodes of the sensor. Such a configuration can prevent bead motion and, thus, prevent a bead from becoming dissociated from a sensor during detection where forces associated with fluid flow overcome forces exerted by the securing member holding a bead in place. Moreover, such a configuration also results in physically touching electrodes to also be positioned within the Debye layer of an adjacent bead or nucleic acid coupled to the adjacent bead.

Improved immobilization can increase the signal and reduce the noise associated with detection. In some cases, the configuration of a KM sensor can position a bead in closer proximity to its securing member. For example, where a securing member is a magnet, the configuration of the KM sensor can bring a bead in close proximity to the magnet and thereby increasing the magnetic force holding the bead in place. Moreover, as the configuration of the KM sensor can position a bead such that it is in physical contact with one or more (or even all) electrodes of a sensor, stronger signals can be acquired since only signals indicative of impedance associated with the bead are measured, and not signals associated with bulk fluid surrounding the bead.

Moreover, in one aspect, the disclosure provides a sensor for sensing a biological molecule. The sensor comprises: (a) a first electrode having a first surface and a second electrode having a second surface, which electrodes are electrically isolated from one another in the absence of a bead situated adjacent to the first electrode and second electrode, which surfaces are oriented at an angle that is greater than 0° with respect to one another such that, during sensing, the bead is substantially immobile; and (b) a securing member that is adjacent to the first electrode and/or second electrode, where during sensing, the securing member positions the bead adjacent to the surfaces such that the electrodes are within a Debye layer of the bead.

In some cases, the surfaces are oriented at an angle that is greater than 5°, greater than 10°, greater than 15°, greater than 20°, greater than 25°, greater than 30°, greater than 35°, greater than 40°, greater than 45°, greater than 50°, greater than 55°, greater than 60°, greater than 65°, greater than 70°, greater than 75°, greater than 85°, greater than 89° or they are at a right angle (e.g., orthogonal) with respect to one another such that, during sensing, the bead is substantially immobile. In some cases, the biological molecule is a nucleic acid. In some cases, the securing member is adjacent to the first electrode and the second electrode. In some cases, the first electrode and/or the second electrode comprise an indentation for restricting movement of the bead. In some cases, the securing member comprises a magnet (e.g., an electromagnetic, a permanent magnet, a magnetic material, etc.).

In some cases, a securing member (e.g., magnet) of a sensor is not exposed to any fluids (e.g., buffers). For example, a securing member may be buried beneath a first electrode of the sensor. In some cases, a securing member (e.g., magnet) may comprise a Titanium Nitride (TiN) coating. If the TiN coating is highly porous, the securing member may be further coated with a protective layer of silicon nitride (SiN) or aluminum (Al) before the first electrode is deposited over the securing member during manufacturing of the sensor. Where the securing member is a magnet, the securing member can be positioned such that it exerts a magnetic force on an associated bead, bringing the bead into physical contact with the first electrode. In some cases, the magnetic force can also bring an associated bead into physical contact with a second electrode of the sensor.

Figure 12A:
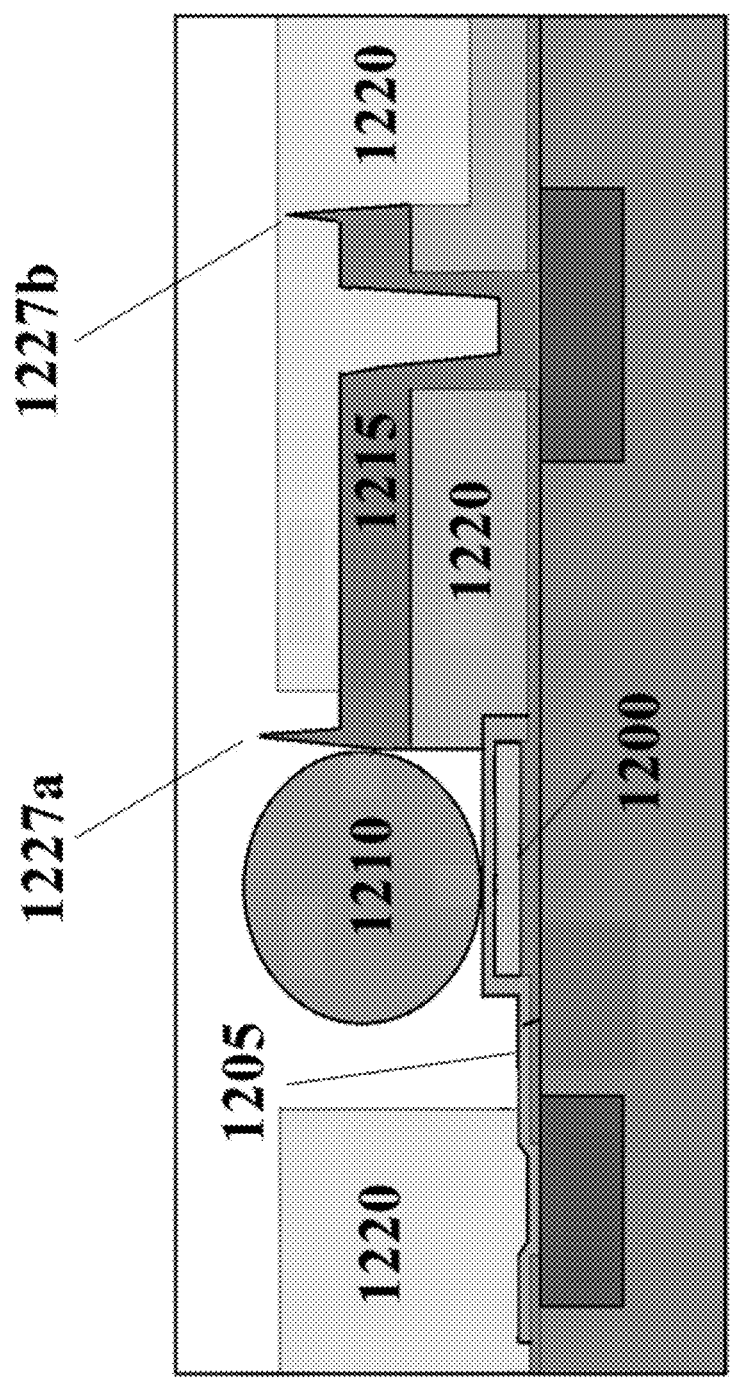
FIG. 12A schematically depicts an example sensor and associated bead described herein.
Figure 12B:
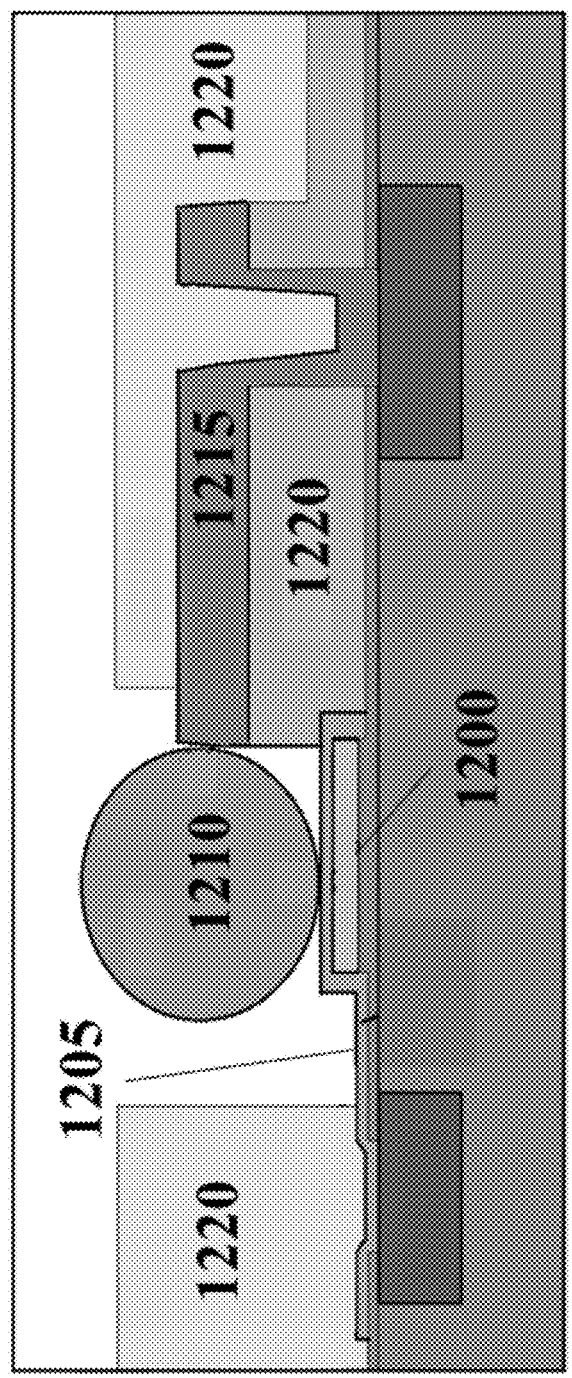
FIG. 12B schematically depicts an example sensor and associated bead described herein.

FIG. 12 schematically depicts an example KM sensor. The sensor has a magnet 1200 surrounded by a first electrode 1205, upon which a bead 1210 rests. The sensor includes a second electrode 1215 that physically contacts the bead 1210 at a position orthogonal to the first electrode 1205. The sensor can also comprise dielectric layers 1220 that can be used to provide an appropriate spatial patterning of conductive and non-conductive material in which to form a working electrode. The coupling of magnetic force from the magnet 1200 and the physical contact of the bead 1210 with the first electrode 1205 and second electrode 1215 improves immobilization of the bead 1210 such that it is in appropriate contact with the electrodes 1205 and 1215, particularly during fluid flow past the sensor. In some cases, the first electrode 1205 and/or the second electrode 1215 comprise one or more fences. As shown in FIG. 12A, second electrode 1215 comprises fences 1227a and 1227b. In other cases, the first electrode 1205 and/or the second electrode 1215 do not comprise a fence. An alternative configuration of the example sensor, not comprising electrodes with a fence(s), is schematically depicted in FIG. 12B.

Figure 13:
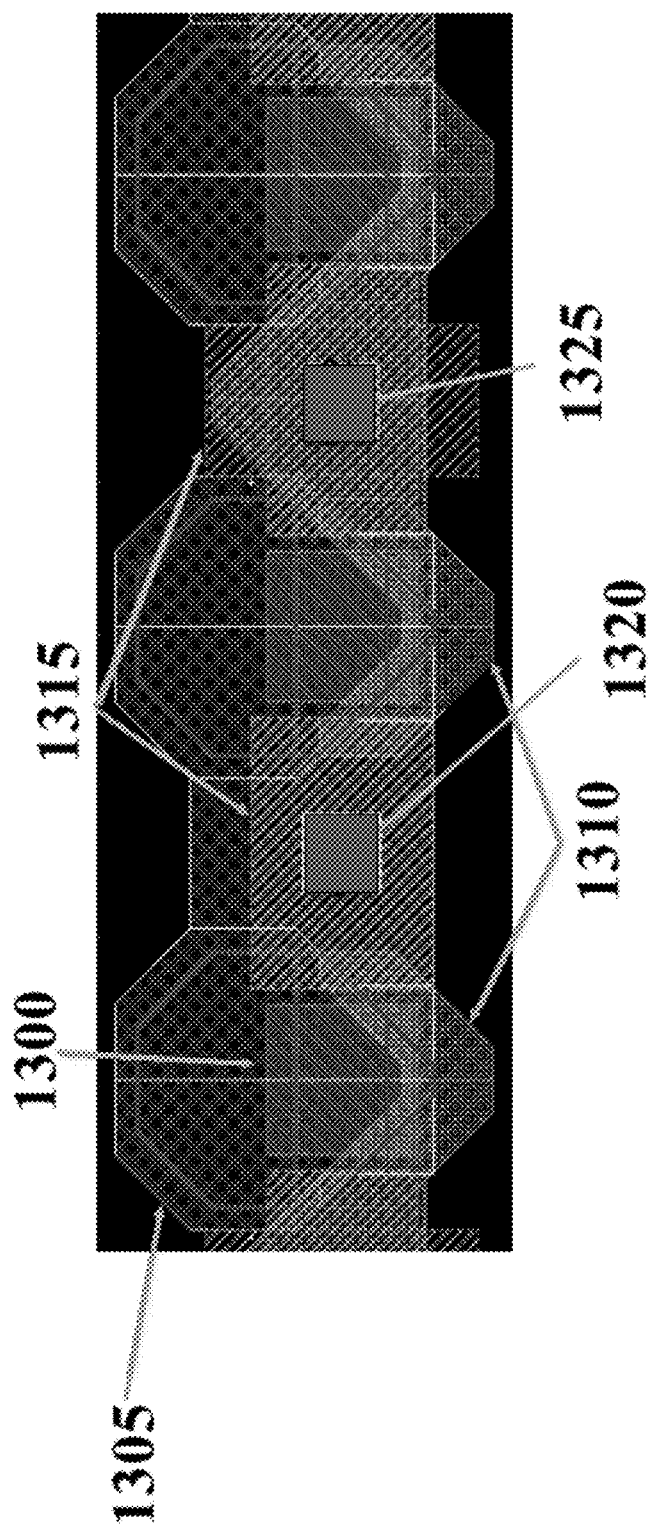
FIG. 13 schematically depicts an example sensor.
Figure 14A:
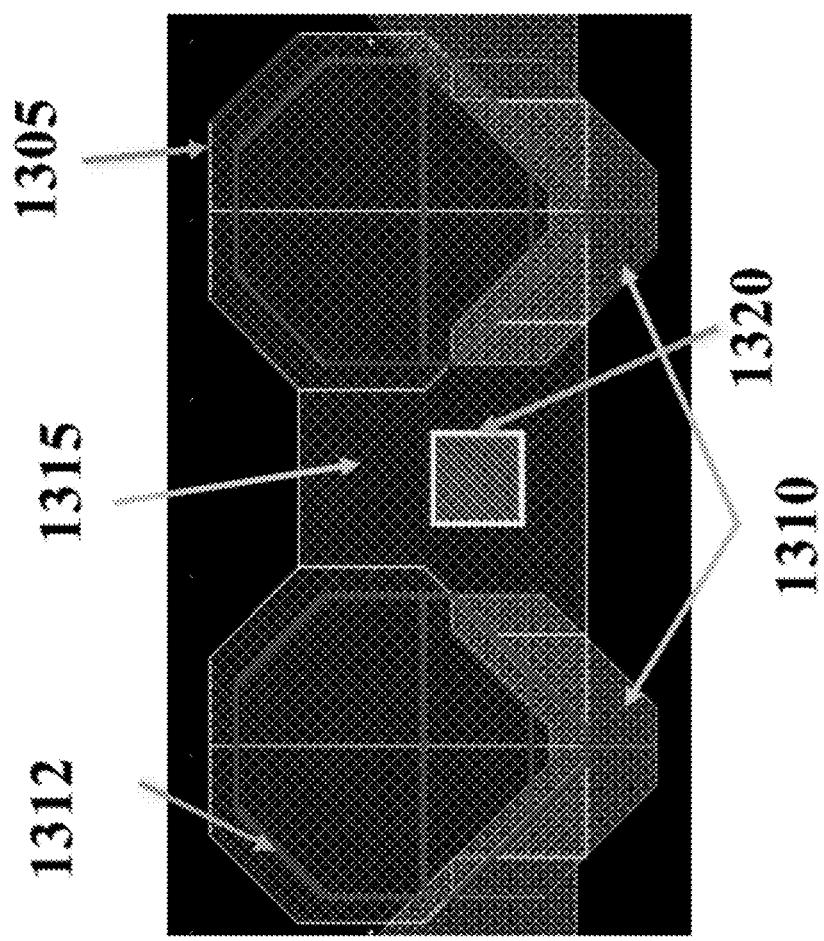
FIG. 14A schematically depicts a first electrode of an example sensor.
Figure 14B:
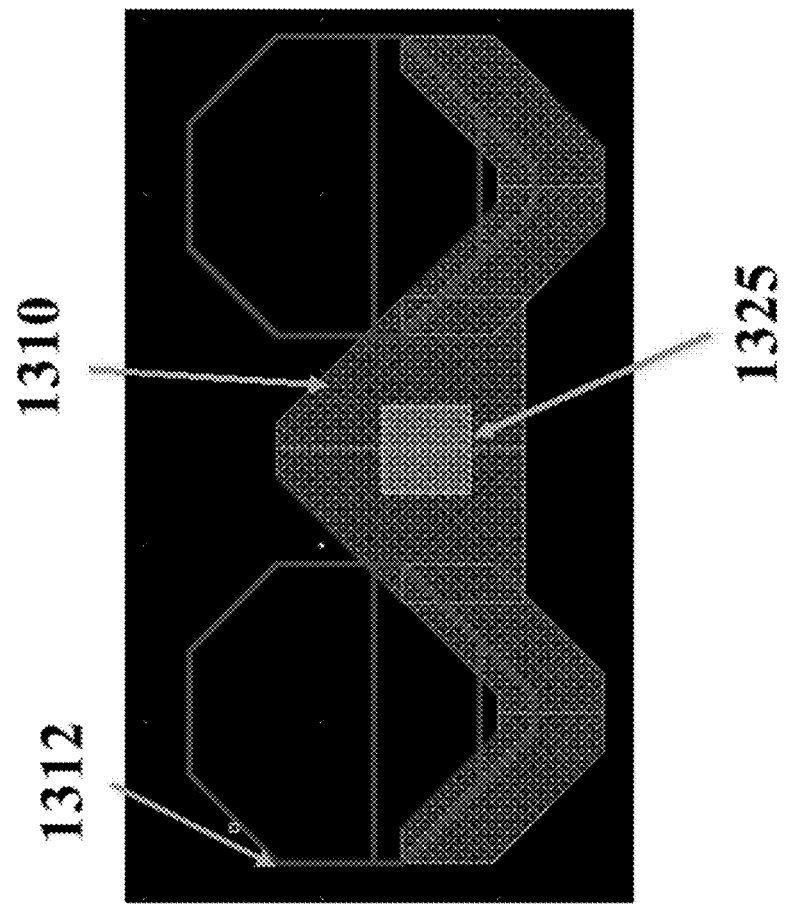
FIG. 14B schematically depicts a second electrode of the example sensor.

FIG. 13 shows a top view of three additional example KM sensors in a sensor array. Each sensor comprises a magnet 1300, a first electrode 1305 and a second electrode 1310. The bead can have any suitable diameter, including between about 0.8 and about 1.5 micrometers. The sensors are also associated with a pad 1315 associated with vias 1320 or 1325. The pad can comprise any suitable material(s) with non-limiting examples that include aluminum, chromium, copper, silicon, a silicon, a silicon based compound (e.g., silicon nitride), titanium, a titanium based compound (e.g., titanium nitride) and combinations thereof. The vias 1320 and 1325 connect first electrodes 1305 and second electrodes 1310 to the pad 1315. A partial layer view of the first electrode 1305 configuration in the sensors of FIG. 13 is schematically depicted in FIG. 14A and a partial layer view of the second electrode 1310 configuration in the sensors of FIG. 13 is schematically depicted in FIG. 14B. FIGS. 14A and 14B show socket openings 1312 not shown in FIG. 13.

The thickness of the first electrode 1205 or 1305 can be minimized in order for the securing member to be as close to an associated bead as possible. Where the securing member is a magnet, such positioning can allow the magnet to exert maximum magnetic force on the bead. In some cases, the first electrode 1205 or 1305 does not need to cover the entire bottom of a sensor opening (e.g., where it does not impose a restriction on an etch of a socket opening during manufacturing of a sensor). In some cases, the first electrode 1205 or 1305 can be used as a socket opening etch stop layer during manufacturing of the sensor where the first electrode 1205 or 1035 is slightly larger than the socket opening.

The second electrode 1215 or 1310 can have sidewall conductance and can be about have nanometer thickness at its sidewall. The width of the second electrode in the V-shape region (see FIGS. 13, 14A and 14B) can be minimized. In some cases, to minimize noise, all or a portion of a surface of the second electrode can be passivated. Moreover, in some cases, there is minimal or no overlap between the first electrode 1205 or 1305 and the second electrode 1215 or 1310. Moreover, as shown in FIGS. 12 and 14A and 14B, the first electrode 1205 or 1305 can be vertically separated. The first electrode 1205 or 1305 can be separated from the second electrode 1215 or 1310 by any suitable distance. For example, the vertical separation between the first electrode 1205 or 1305 and the second electrode 1215 or 1310 is at least about 1 nanometer (nm), at least about 5 nm, at least about 10 nm, at least about 50 nm, at least about 100 nm, at least about 200 nm, at least about 300 nm, at least about 400 nm, at least about 500 nm, at least about 1000 nm or more. In some cases, the vertical separation between the first electrode 1205 or 1305 and the second electrode 1215 or 1310 is at most about 1000 nm, at most about 500 nm, at most about 400 nm, at most about 300 nm, at most about 200 nm, at most about 100 nm, at most about 50 nm, at most about 10 nm, at most about 5 nm, at most about 1 nm or less.

In some cases, an appropriate separation distance can be chosen such that an associated bead comes into physical contact with the second electrode 1215 or 1310 sidewalls near the bead equator and/or such that a parasitic electrical path between the two electrodes is minimized. Moreover, in some cases, the two electrodes are deposited at the same time, such as when an associated socket opening is first opened and the deposition is over topography and pattern.

In some cases, the sensor may also include a resistive temperature detector (RTD) that may be separate from the first electrode 1205 or 1305. The RTDs can be covered with SiN and/or silicon dioxide ($SiO_2$) such that they do not come into contact with fluid flowing past the sensor. Moreover, the RTD may also comprise TiN, the temperature coefficient and resistivity of which can be helpful in optimizing the dimensions of the RTD structure.

In some cases, at least a portion of the electrodes are made out of $SiO_2$, including at least a portion of the top surfaces of the electrodes. Moreover, one or more non-electrode regions of the sensor may be passivated with polyamide. Moreover, various layers and components (e.g., electrodes, dielectric layers, intermediate layers, a securing member, etc.) of a sensor can comprise one or more of aluminum, silicon dioxide, silicon nitride, titanium nitride, copper, polyamide, magnetic material, and/or other layers.

While the KM sensors described herein are described with respect to nucleic acid, they can be used to detect any suitable biological species (or reaction associated with such a biological species) associated with a bead or particle, including proteins, protein binding reactions, nucleic acids hybridization reactions, nucleic acid sequencing reactions, bound ligands and ligand binding reactions.

Multi-Frequency and Multi-Phase Sensing

A sensor included in a device or system or utilized in a method described herein can perform measurements using a plurality of applied voltage waveforms having a plurality of frequencies and/or phases. Multiple frequencies and/or phases can provide additional data from which to determine the presence of an analyte (e.g., nucleic acid molecule). In some cases, the use of multiple frequencies and/or phases is complementary to sequencing under multiple conditions (e.g., various buffers) as described elsewhere herein.

In one aspect, the disclosure provides a method for detecting an analyte. The method comprises: (a) activating a sensor comprising at least two electrodes by (i) applying at least two voltage waveforms with different frequencies to the at least two electrodes, and (ii) deriving one or more first electrical parameters from first signals indicative of first impedances each associated with one of the at least two voltage waveforms; (b) coupling the analyte to a support proximate to the at least two electrodes or a molecule coupled to the support; (c) applying the at least two voltage waveforms to the at least two electrodes and deriving one or more second electrical parameters from second signals indicative of second impedances each associated with one of the at least two voltage waveforms; and (d) determining a presence of the analyte by comparing at least one of the first electrical parameters with at least one of the second electrical parameters.

In some cases, the analyte comprises a biological molecule, which may be, for example, a nucleic acid, a protein and/or a peptide. In the case of nucleic acid sequencing, the analyte may comprise a nucleotide base that is a component of a nucleic acid sequencing reaction. Moreover, in some cases, the support comprises a bead and/or at least one of the at least two voltage waveforms comprises a square wave.

Frequencies of the at least two waveforms can comprise frequencies along a continuous frequency sweep.

Additionally, the one or more first and/or second electrical parameters may selected from a resistance associated with the support; a fluid capacitance associated with fluid proximate to at least one of the at least two electrodes; an electrode capacitance associated with one or more of the at least two electrodes; and a combination thereof. In some cases, the first signals comprise a first current and a second current each associated with one of the at least two waveforms. The first impedances can be derived from the first current and the second current. In some cases, in (a), the one or more first electrical parameters are derived using the first impedances.

In some cases, the second signals comprise a first current and a second current each associated with one of the at least two waveforms. The second impedances can be derived from the first current and the second current and, in (c), the one or more second electrical parameters can be derived from the second impedances.

In some cases, one or more of the first impedances and/or the second impedances are an impedance associated with a Debye layer of the support or a molecule associated with the support. Moreover, in some cases, one or more of the at least two electrodes is positioned within a Debye layer of the support. Additionally, (a) and/or (c) may be performed in the presence of a fluid (e.g., a buffer) to which one or more of the at least two electrodes are exposed. In some cases, the deriving in (a) and/or (c) is completed with the aid of one or more computer processors.

Figure 15:
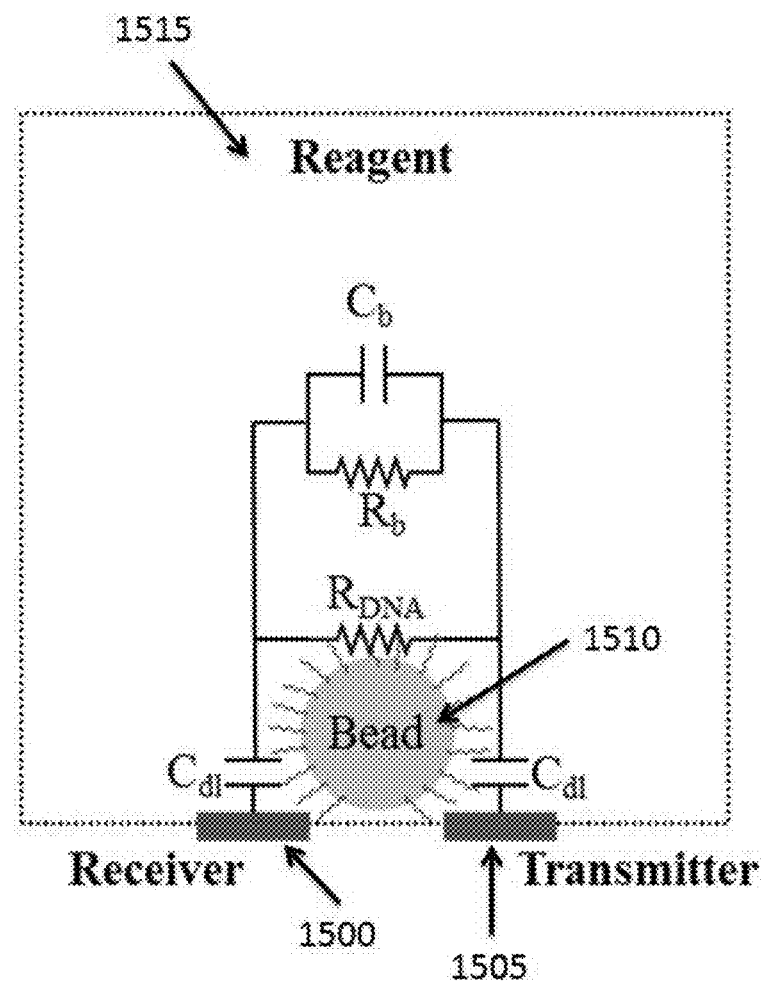
FIG. 15 schematically depicts an example electrical circuit.

FIG. 15 schematically depicts an electrical circuit associated with an example sensor. The electrical circuit comprises Transmitter 1500 and Receiver 1505 electrodes. An applied voltage waveform can be applied across the Transmitter 1500 and the Receiver 1505 electrodes and the resulting current flowing from the Transmitter 1500 to the Receiver 1505 can be measured. In the absence of the bead 1510, the Transmitter 1500 and the Receiver 1505 electrodes are electrically isolated. The electrical circuit further comprises a double-layer capacitance ($C_{dl}$) associated with each of the Transmitter 1500 and the Receiver 1505 electrodes; an electrical resistance ($R_{DNA}$) around the bead 1510, where the electrical resistance is associated with an analyte (e.g., nucleic acid, such as DNA) coupled to the bead 1510 and/or the bead 1510 itself; an electrical resistance ($R_b$) in a bulk reagent 1515 (e.g., buffer) and a capacitance ($C_b$) between the Transmitter 1500 and the Receiver 1505 through the bulk reagent 1515. Due to presence of multiple capacitances and resistances, and according to their resistor-capacitance (RC) circuit time constant (RC time constant), an electrical signal detected by the sensor can be frequency and/or phase dependent.

Figure 16:
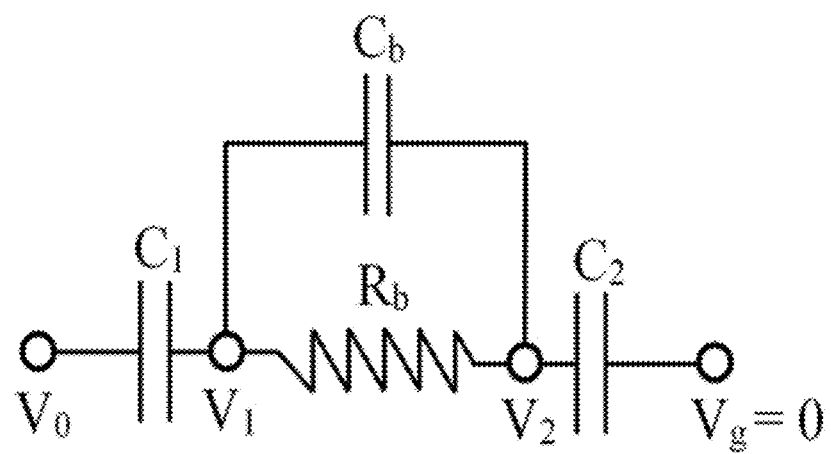
FIG. 16 schematically depicts an example lumped electrical circuit.

In some cases, the potential drop across the double layer can be approximated by the lumped electrical circuit model shown in FIG. 16. An unknown parameter in the circuit is the potential drop across two double-layers (e.g., $V_1-V_0$ or $V_2-V_g$) on the Transmitter 1500 and Receiver 1505 electrodes. Once determined, the potential drop across the two double-layers can be used for calculation of the double layer-capacitance and/or response current of the sensor. If the resistivity of the bulk reagent (e.g., buffer) is known or can be approximated, the current can be calculated from the ordinary differential equations (ODEs) shown as Equation 1, Equation 2 and Equation 3 where: for capacitor $C_1$ (Equation 1), $$i = \frac{d(C_1 V)}{dt} = \frac{d}{dt}(C_1 \cdot \Delta V_1), \Delta V_1 = V_0 - V_1;$$

for resistor $R_b$ (Equation 2), $$i = \frac{V_2 - V_1}{R_b} + \frac{d[C_b(V_2 - V_1)]}{dt};$$

and
for capacitor $C_2$ (Equation 3), $$i = \frac{d(C_2 V)}{dt} = \frac{d}{dt}(C_2 \cdot \Delta V_2), \Delta V_2 = V_2 - V_g = V_2.$$

Therefore, by solving these three ODEs (Equation 1, Equation 2 and Equation 3), the unknown variables (e.g., i, $V_1$ and $V_2$) can be determined. The current can be a good approximation of electrical signal obtained from the sensor without the bead 1510. Also, if the total resistance is calculated between the Transmitter 1500 and Receiver 1505 electrodes with a bead 1510 and coupled analyte (e.g., DNA), the output current from the sensor can be approximated.

If the two double-layer capacitances are identical, then the voltages can be expressed by Equation 4, which is $$\Delta V_1 = \Delta V_2 \rightarrow V_2 - V_1 = V_0 - 2\Delta V_1.$$

If a square applied voltage wave is applied, then the output current ($I_{out}$) can be solved using Equation 5, where $\Delta t$ is the integration time:

$$I_{out} = \frac{1}{\Delta t/2} \int_0^{\Delta t/2} i \, dt.$$

The double-layer capacitance can depend on the voltage drop across the double-layer. The value for the capacitance and voltage drop can be determined using a trial and error process. The double-layer capacitance ($C_{dl}$) per unit area of an associated electrode can be approximated as shown in Equation 6 based on modified Poisson-Boltzman model which considers the effect of ion size, which is:

$$C_{dl} = \frac{2 z e N_A c_b \lambda_D}{\psi_D} \sqrt{\frac{2}{v} \log\left[1 + 2v \sinh^2\left(\frac{z e \psi_D}{2 k_B T}\right)\right]}.$$

In Equation 6 above, z is valance, e is electron charge, $N_A$ is Avogadro number, $c_b$ is bulk concentration of the buffer, $\lambda_D$ is Debye length, $\psi_D$ is voltage drop across the double layer which is equal to $\Delta V_1$, $\upsilon$ is packing parameter, $k_B$ is Boltzmann constant and T is temperature. The packing parameter adds the effect of finite ion size to estimation of double layer capacitance and is estimated by $\upsilon = 2a^3 N_A c_b$ where a is ion size.

Either of these capacitances based on the applied voltage and frequency and find the final voltage drop and double-layer capacitance in the trial and error process. The output current of the sensor can be determined using Equation 7, which is $$i = \frac{d}{dt}(C_{dl}\Delta V_1) = \frac{V_0 - 2\Delta V_1}{R_b}.$$

Based on the trial and error process, the voltage drop across the double-layer as well as double-layer capacitance can be modified based on the modified Gouy-Chapman method, resulting in an approximation for double-layer capacitance as $$C_{dl} = \frac{\varepsilon}{\lambda_D}.$$

Figure 17A:
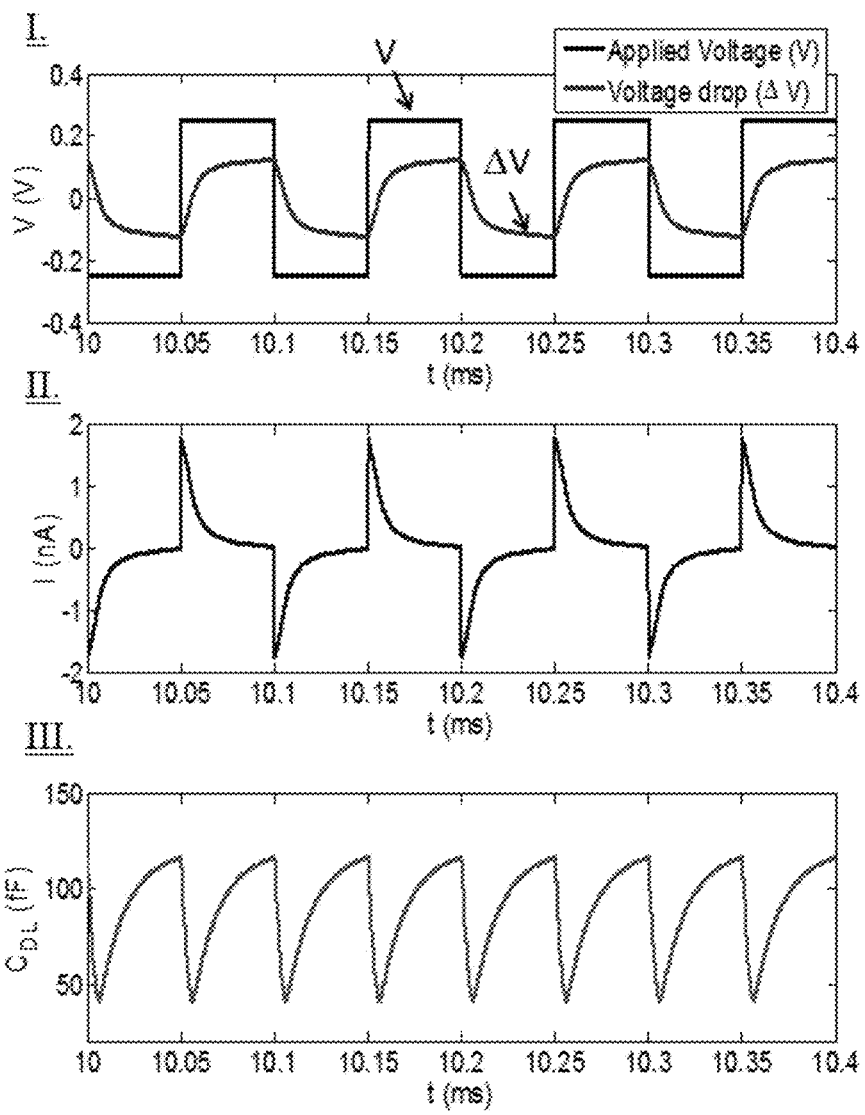
FIG. 17A graphically shows the applied voltage, voltage drop across the double layer, output current and double layer capacitance associated with an example sensor operated at 10 kHz.
Figure 17B:
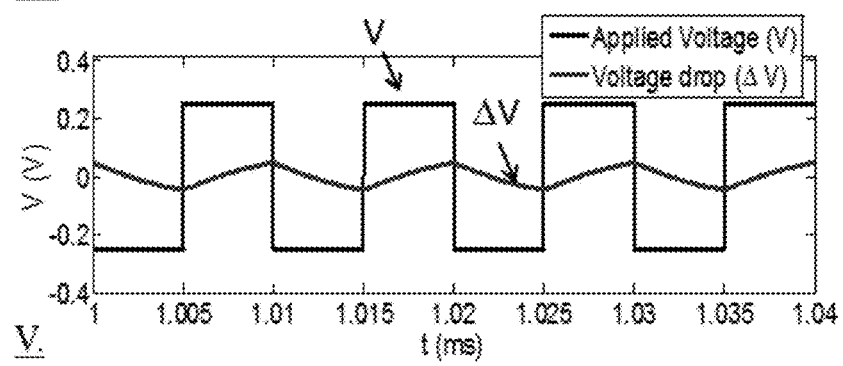
FIG. 17B graphically shows the applied voltage, voltage drop across the double layer, output current and double layer capacitance associated with an example sensor operated at 100 kHz.
Figure 17B:
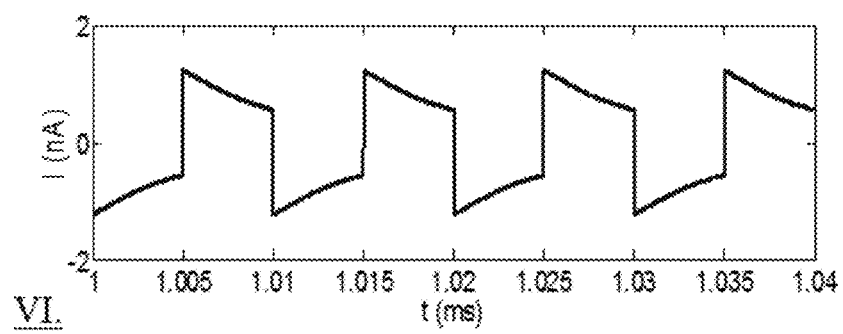
Figure 17B:
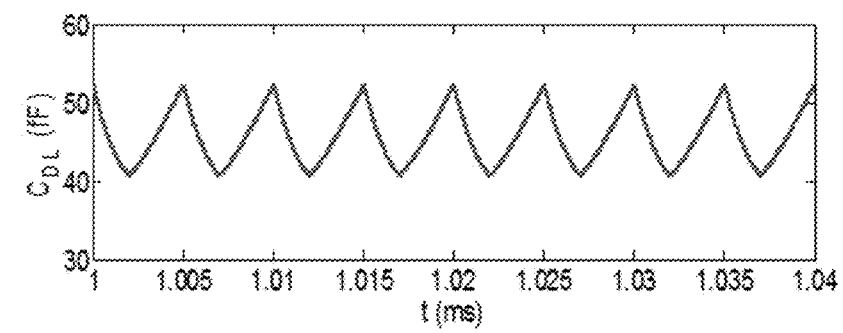
Figure 18:
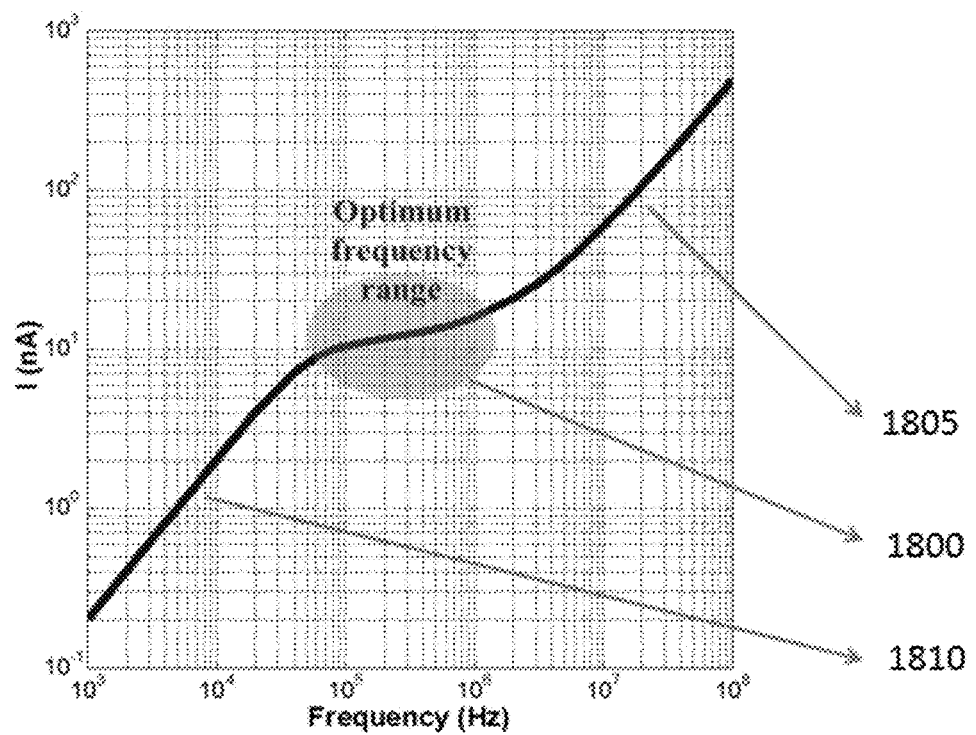
FIG. 18 graphically shows the frequency response of an example sensor.

FIG. 17A, FIG. 17B and FIG. 18 graphically depict the results of an example numerical simulation for a sensor. The response current and double layer capacitance can be calculated using numerical methods based on the applied square wave with a certain frequency. With reference to FIG. 17A, in the top panel (I), the applied voltage is shown as a square wave, with the voltage drop overlaid. In the top panel (I), the vertical axis is in units of volts (V) and ranges from −0.4V to 0.4V. In all panels (I, II and III), the horizontal axis is in units of milliseconds (ms) and range from 10 ms to 10.4 ms. The frequency is 10 kilohertz (kHz). The output current (I) is shown in the middle panel (II), where the vertical axis is in units of milliamperes (mA) and ranges from −2 mA to 2 mA. The double layer capacitance ($C_{DL}$) is shown in the bottom panel (III), where the vertical axis is in units of femtofarads (fF) and ranges from 0 fF to 150 fF.

FIG. 17B depicts the applied voltage (square wave, top panel IV), voltage drop across the double layer (top panel IV), output current (middle panel V) and double layer capacitance (bottom panel VI) for the sensor operated at 100 kHz. In all panels (IV, V and VI), the horizontal axis is time measured in ms ranging from 1 ms to 1.04 ms. All vertical axis are identical to those in FIG. 17A except for the bottom panel ($C_{dl}$), which ranges from 30 fF to 60 fF.

The frequency response of the sensor is graphically depicted in FIG. 18. The flat region 1800 of the frequency response indicates the frequency range that is preferred for measuring the resistance (i.e., the effect is dominated by resistance) in this example. From this calculation, the flat region is in the range of about 100 kHz to about 1 MHz. At higher frequencies 1805, the effect is dominated by parasitic capacitance. At lower frequencies 1810, the effect is dominated by double-layer capacitance. The vertical axis is current measured in nanoamperes (nA) and shown on a logarithmic scale ranging from $10^{-1}$ nA to $10^3$ nA. The horizontal axis is frequency shown on a logarithmic scale ranging from $10^3$ Hertz (Hz) to $10^8$ Hz.

As is provided herein, a signal can have frequency dependency. Also, the phase of input signal can have effect on the signal as the signal often has components in various phases. The methods and systems described herein can measure the signal at multiple frequencies and/or at multiple phases. The result of these measurements can be used to estimate changes in different components of the circuit, including those that are dependent on nucleotide incorporation during a sequencing-by-synthesis reaction.

In an additional aspect, the disclosure provides a method for detecting an analyte. The method comprises: (a) activating a sensor comprising at least two electrodes by (i) applying at least two voltage waveforms with different phases to the at least two electrodes, and (ii) deriving one or more first electrical parameters from first currents each associated with one of the at least two voltage waveforms; (b) coupling the analyte to a support proximate to the at least two electrodes or a molecule coupled to the support; (c) applying the at least two voltage waveforms to the at least two electrodes and deriving one or more second electrical parameters from second currents each associated with one of the at least two voltage waveforms; and (d) determining a presence of the analyte by comparing at least one of the first electrical parameters with at least one of the second electrical parameters.

In some cases, the analyte comprises a biological molecule such as, for example, a nucleotide base, a nucleic acid, a protein and/or a peptide. In some cases, the analyte comprises a nucleotide base that is a component of a nucleic acid sequencing reaction. In some cases, the support comprises a bead. Moreover, at least one of the at least two voltage waveforms may comprise a square wave.

Additionally, in (a), the deriving one or more electrical parameters can comprise deriving phase derivatives for the first currents and deriving a Fourier transform (e.g., a Fast Fourier Transform (FFT)) for the phase derivatives. In such cases, the method can further comprise deriving an impedance from the Fourier transform and, in some cases, deriving the one or more first electrical parameters from the impedance.

Moreover, in (c), the deriving can comprise deriving phase derivatives for the second currents and deriving a Fourier transform (e.g., Fast Fourier Transform (FFT)) for the phase derivatives. In such cases, the method can further comprise deriving an impedance from the Fourier transform and, in some cases, deriving the one or more second electrical parameters from the impedance.

Additionally, the one or more first and/or second electrical parameters can be selected from a resistance associated with the support; a fluid capacitance associated with fluid proximate to at least one of the at least two electrodes; a capacitance associated with one or more of the at least two electrodes; and a combination thereof. In some cases, one or more of the at least two electrodes is positioned within a Debye layer of the support. Furthermore, (a) and/or (c) may be performed in the presence of a fluid (e.g., a buffer). One or more of the at least two electrodes may be exposed to the fluid. Moreover, the deriving in (a) and/or (c) can be completed with the aid of one or more computer processors.

At different frequencies, the signal can be measured and used to solve a system of equations to calculate various components of an electrical circuit associated with a sensor. In a multi-phase analysis, the phase can be swept at a fixed frequency (i.e., varied over a range). The time response of a sensor can be calculated by calculating the derivative of the signal. A Fast Fourier Transform (FFT) of the time response can give an estimate of frequency response at the sensor. Then, each component of the electrical circuit can be calculated using the frequency response. In some cases, a multi-phase analysis comprises phase data acquisition, followed by calculation of the derivative of the signal to determine the time response of the sensor, followed by FFT of the time response, followed by combining all phases to calculate admittance and/or impedance and electrical circuit components.

Each FFT component ($y_i$) can be written as shown in Equation 8, which is:

$$y_i = \sum_{i=1,3...}^{N} A_i \cos(\varphi_i + i\varphi_j),$$

where A is amplitude, $\varphi_i$ is phase, $\varphi_j$ is initial phase and N is number of FFT components.

By re-arranging this component, $y_i$ can be written based on admittance components $X_i$ and $Y_i$, as shown in Equation 9, which is:

$$y_i = \sum_{i=1,3...}^{N} A_i\cos(\varphi_i)\cos(i\varphi_j) - A_i\sin(\varphi_i)\sin(i\varphi_j) = $$

$$\sum_{i=1,3...}^{N} X_i\cos(i\varphi_i) - Y_i\sin(i\varphi_j),$$

where, based on multiphase measurement at multiple $\varphi_a$ measurement ($\varphi_1, \varphi_2, \ldots, \varphi_n$), the n components of total admittance ($X_1, Y_1, X_3, Y_3, \ldots, X_n, Y_n$) can be reconstructed by solving a linear system of equations.

Moreover, for $i^{th}$ harmonics, the complex admittance can be calculated from Equation 10, which is:

$$i^{th}\ \text{Admitance} = X_i + jY_i.$$

For $i^{th}$ harmonics, the impedance of the system can be estimated using calculated admittance as shown in Equation 11, which is:

$$i^{th}\ \text{Impedance} = \frac{1}{i^{th}\ \text{Admitance}} = \frac{1}{X_i + jY_i}.$$

Next, the circuit components such as resistance and capacitances can be estimated by solving the non-linear system of equations using multiple harmonics of impedance (I=1, 3, ..., n). The number of harmonics for impedance can depend on the number of initial phases that are used for measurement as shown in Equation 12, which is:

Number of harmonics=2×Number of phases

The same process can be employed to use multi-frequency measurement to estimate impedance of the system (i.e., the admittance and subsequently impedance can be calculated directly from measurement at each frequency).

Figure 19A:
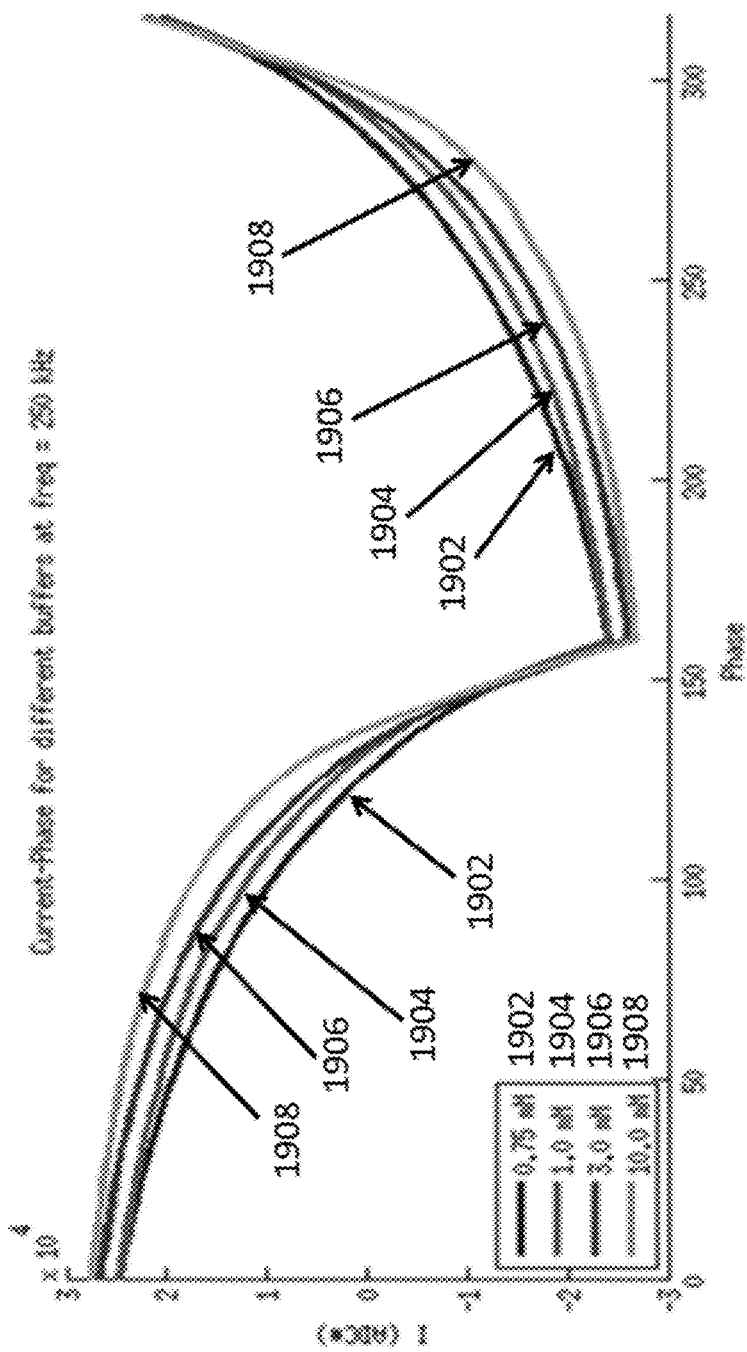
FIG. 19A graphically shows signals from an example sensor at different phases.
Figure 19B:
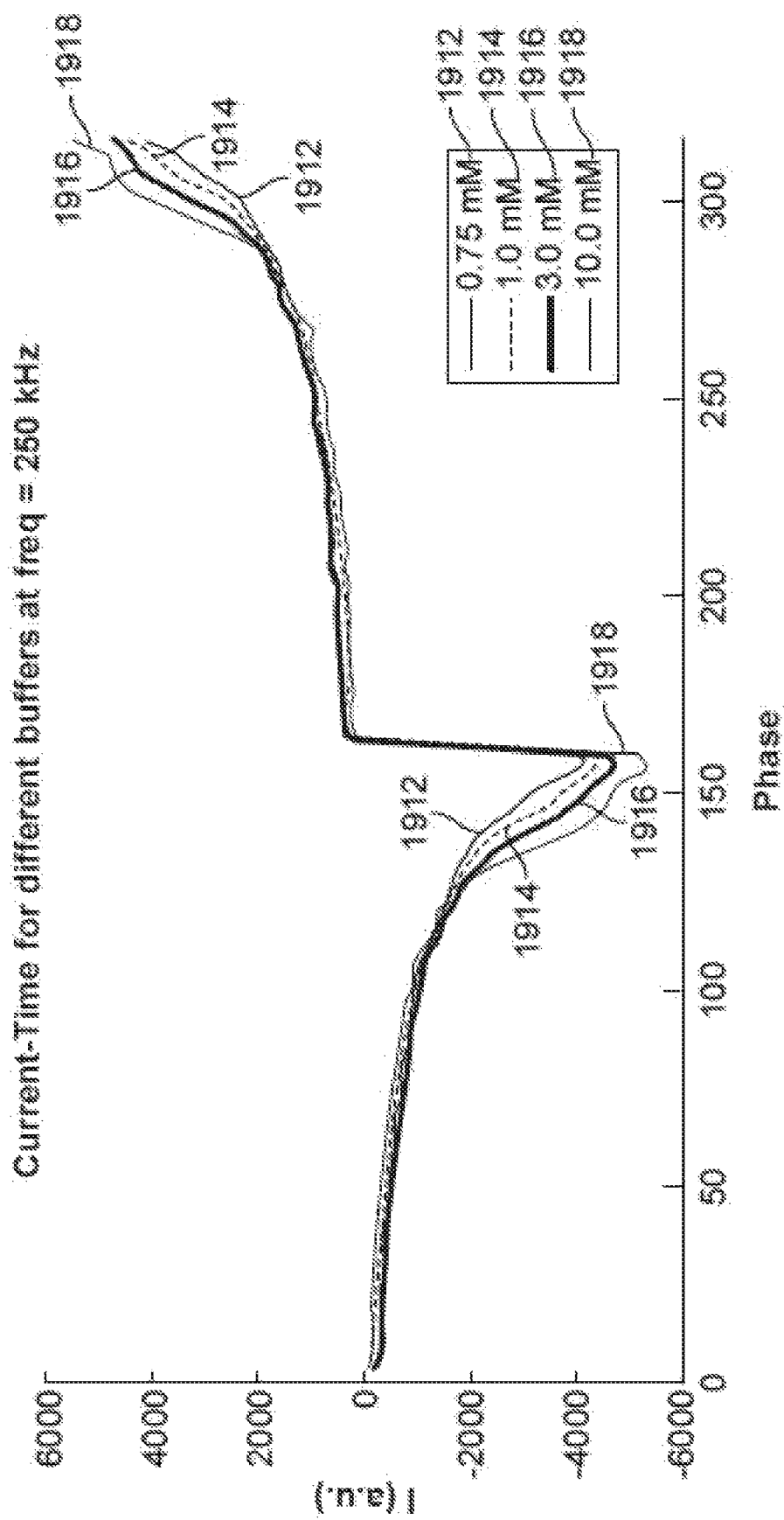
FIG. 19B graphically shows the time response of an example sensor based on phase data.

FIG. 19A, graphically shows signals from an example sensor operated at different phases and in different buffers at a frequency of 250 kHz. The vertical axis is a linear scale of current ranging from $-3 \times 10^4$ to $3 \times 10^4$ ADC# (analog to digital converter units). The horizontal axis is the phase ranging from 0 to 300 (multiples of a time constant of 12.5 ns). Data are presented for buffer concentrations of 0.75 mM 1902, 1.0 mM 1904, 3 mM 1906 and 10 mM 1908. With respect to FIG. 19A, the buffer is magnesium (II) sulfate ($MgSO_4$)-Tris-HCl. Moreover, FIG. 19B graphically depicts the time response of the example sensor based on the data presented in FIG. 19A. The data shown in FIG. 19B is obtained by taking the derivative of the various curves in FIG. 19A. The vertical axis ranges from −6000 a.u. (arbitrary units) to 6000 a.u. Curves are presented for buffer concentrations of 0.75 mM 1912, 1.0 mM 1914, 3 mM 1916 and 10 mM 1918.

Figure 20A:
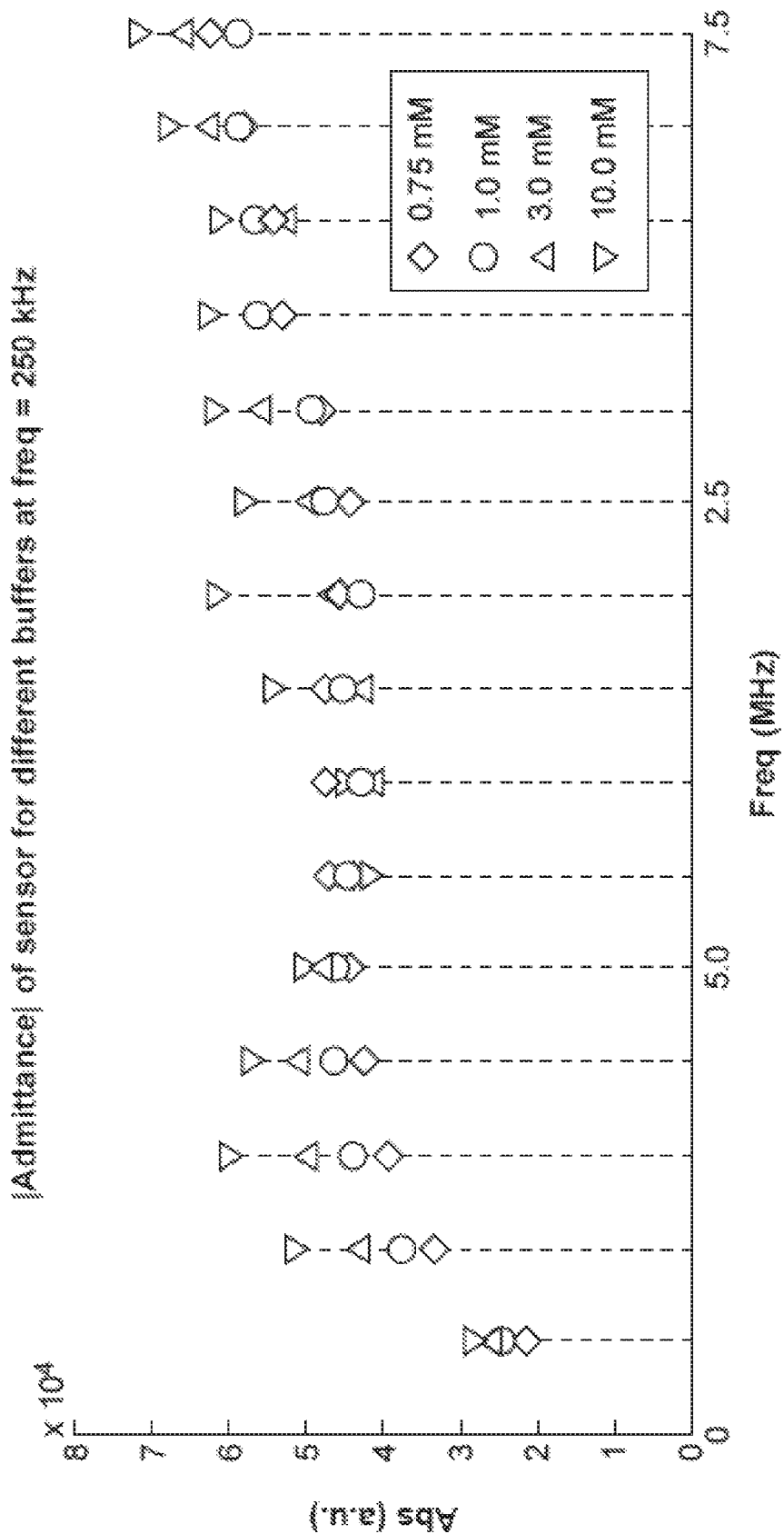
FIG. 20A graphically shows the admittance amplitude at various frequencies for an example sensor.
Figure 20B:
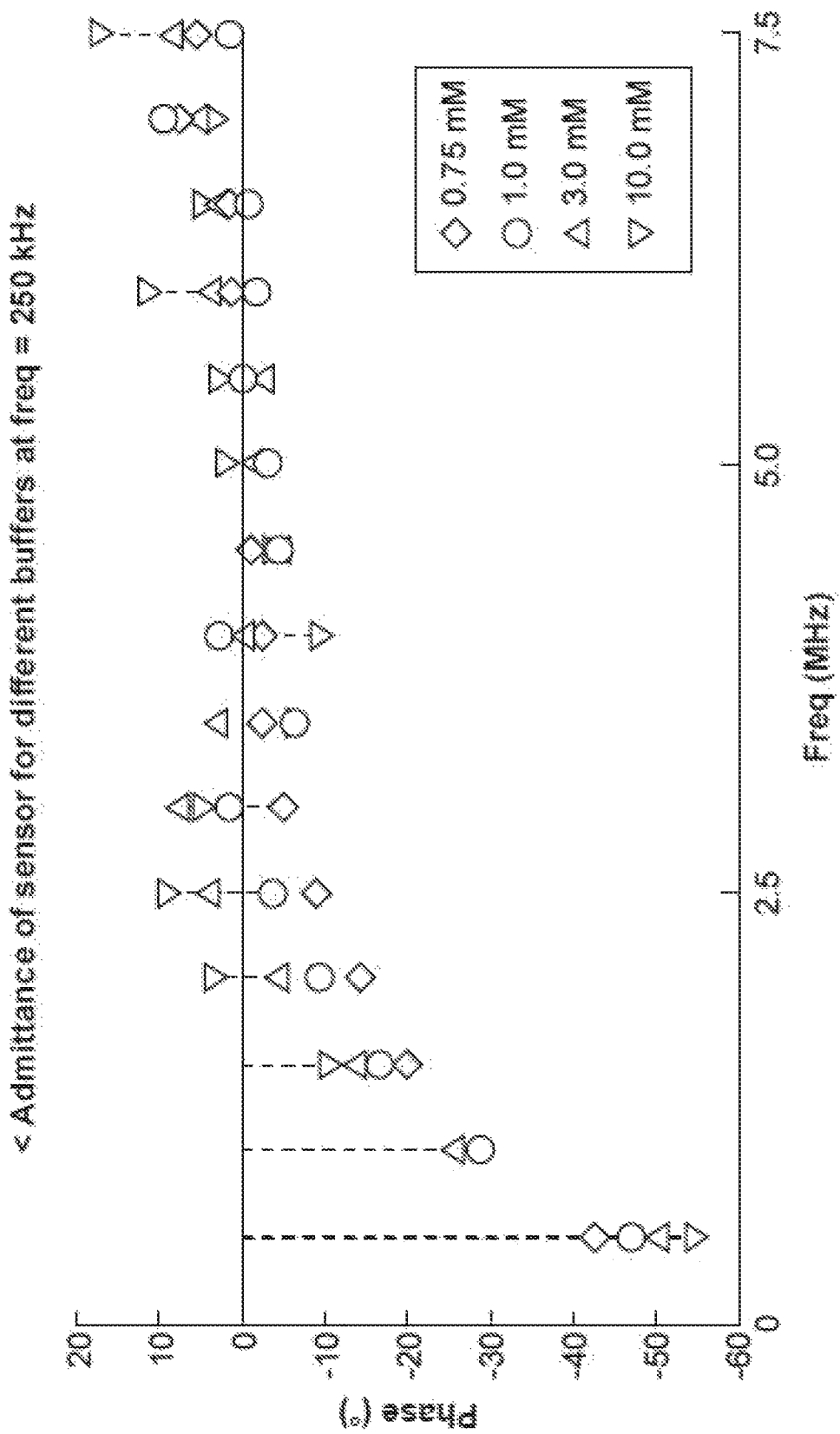
FIG. 20B graphically shows the admittance phase at various frequencies for an example sensor.

FIG. 20A graphically depicts admittance amplitude calculated for the example sensor discussed above with respect to FIG. 19A. The data shown in FIG. 20A are amplitude of an FFT of the data depicted in FIG. 19B. The vertical axis is Abs in units of a.u. ranging from 0 to $8 \times 10^4$ arbitrary units (a.u.). The horizontal axis is frequency ranging from 0 to 7.5 MHz. FIG. 20B graphically depicts admittance phase for the example sensor discussed above with respect to FIG. 19A. The data shown in FIG. 20B are phase of an FFT of the data depicted in FIG. 19B. The vertical axis is phase ranging from −60° to 20°. The horizontal axis is frequency ranging from 0 to 7.5 megahertz (MHz).

Figure 21A:
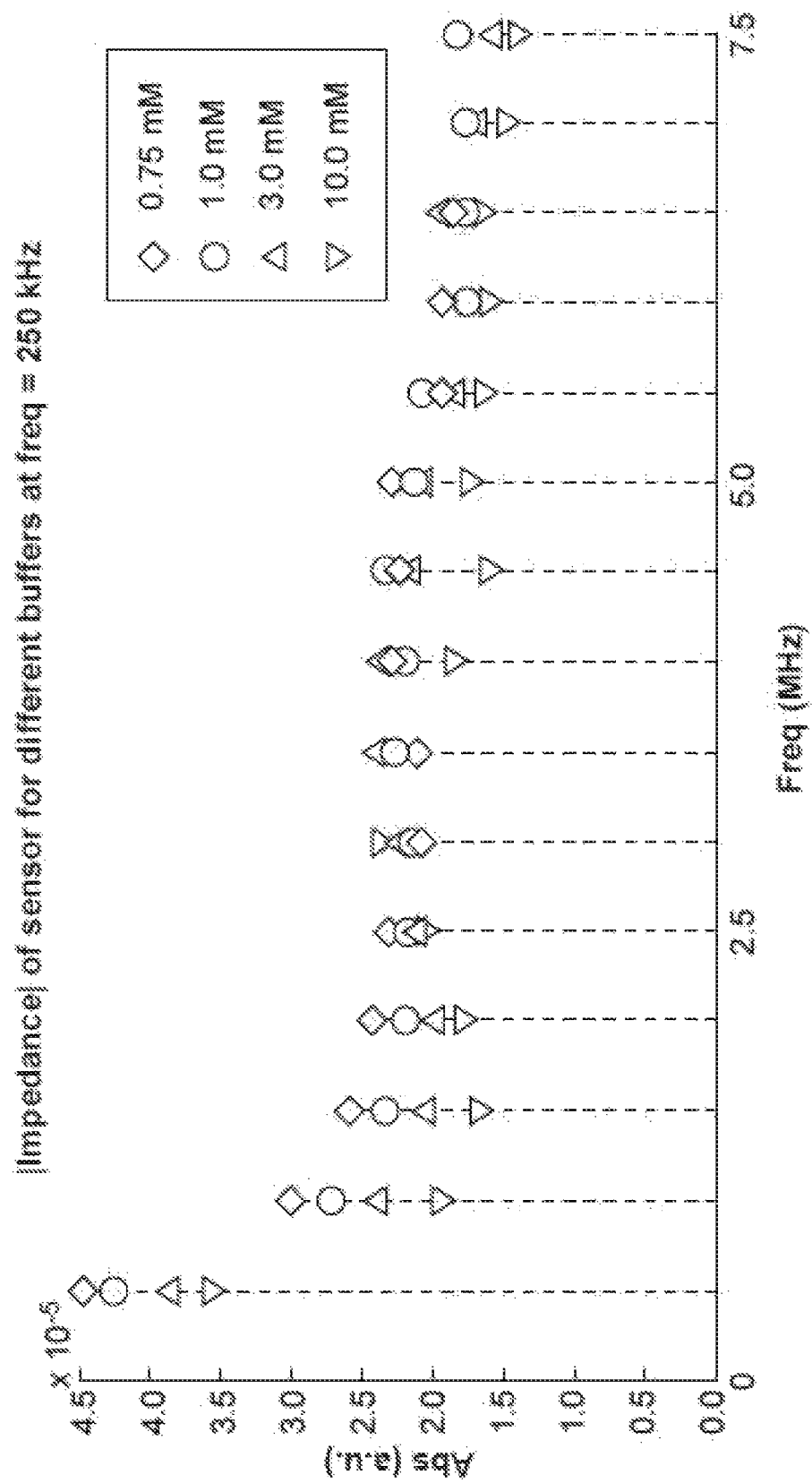
FIG. 21A graphically shows the impedance amplitude at various frequencies for an example sensor.
Figure 21B:
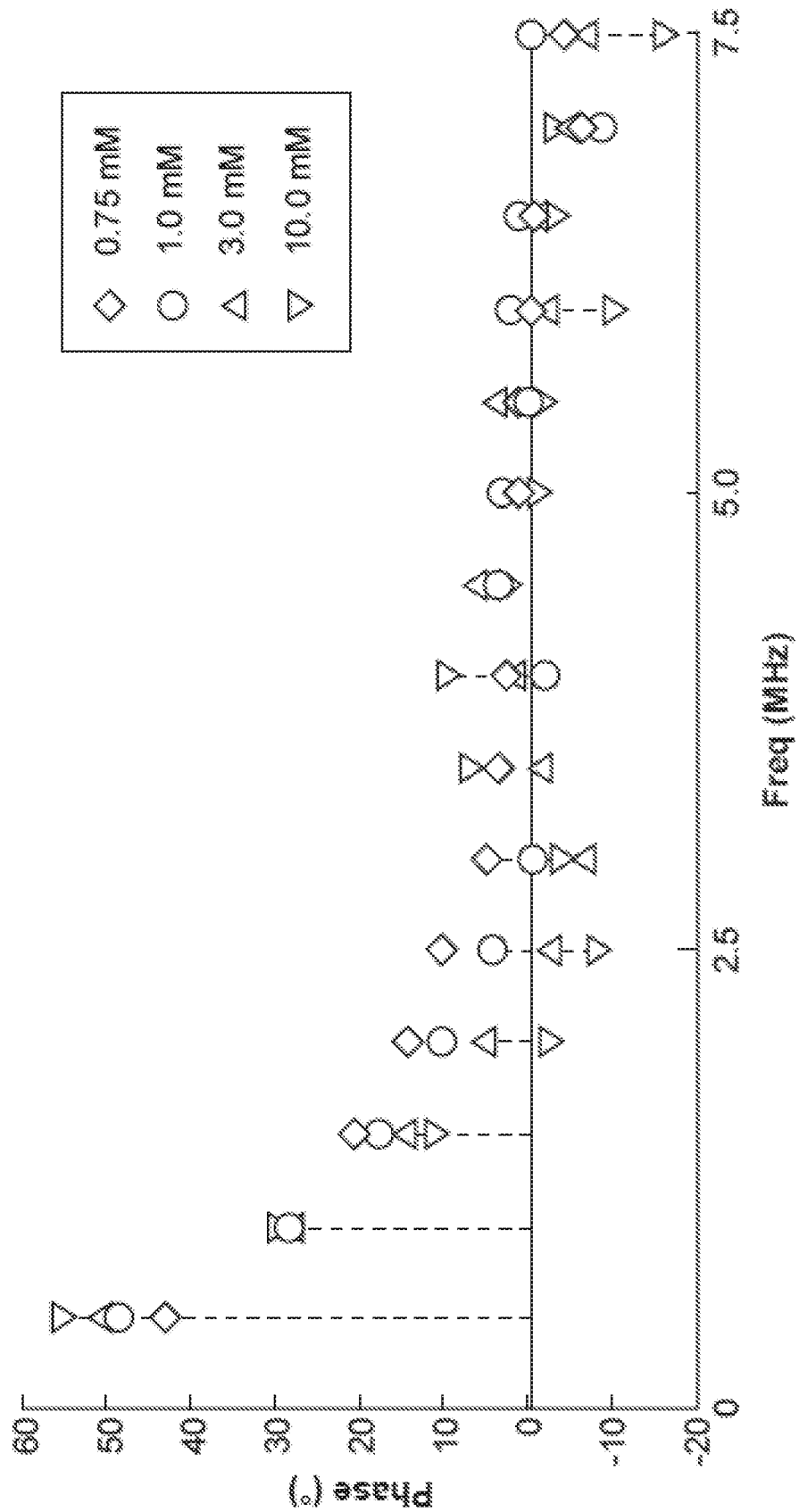
FIG. 21B graphically shows the impedance phase at various frequencies for an example sensor.

FIG. 21A graphically depicts impedance amplitude data for the example sensor (and its associated bead, analyte and buffer) discussed above with respect to FIGS. 19A-20B and are derived from the data of FIG. 20A and FIG. 20B. The vertical axis is Abs ranging from 0 to $4.5 \times 10^{-5}$ a.u. and the horizontal axis is frequency ranging from 0 to 7.5 MHz. FIG. 21B graphically depicts impedance phase data for the example sensor (and its associated bead, analyte and buffer) discussed above with respect to FIGS. 19A-20B and are derived from FIG. 20A and FIG. 20B. The vertical axis is phase ranging from −20° to 60° and the horizontal axis is frequency ranging from 0 to 7.5 MHz.

Figure 22:
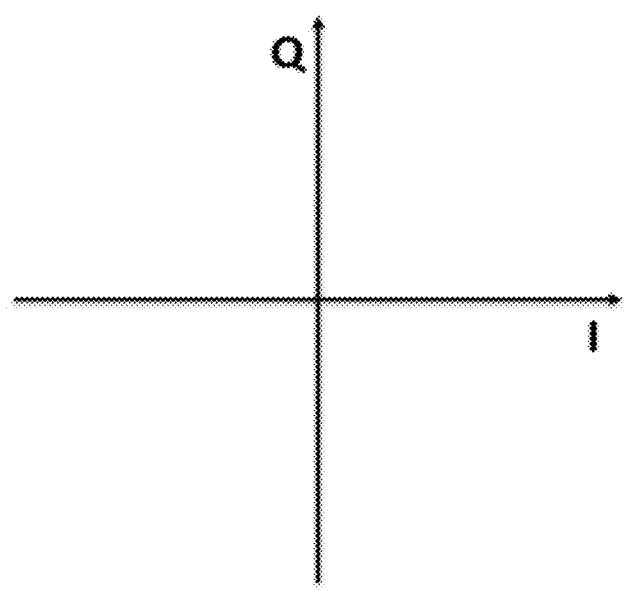
FIG. 22 graphically shows example I and Q components of two phase measurement.
Figure 23A:
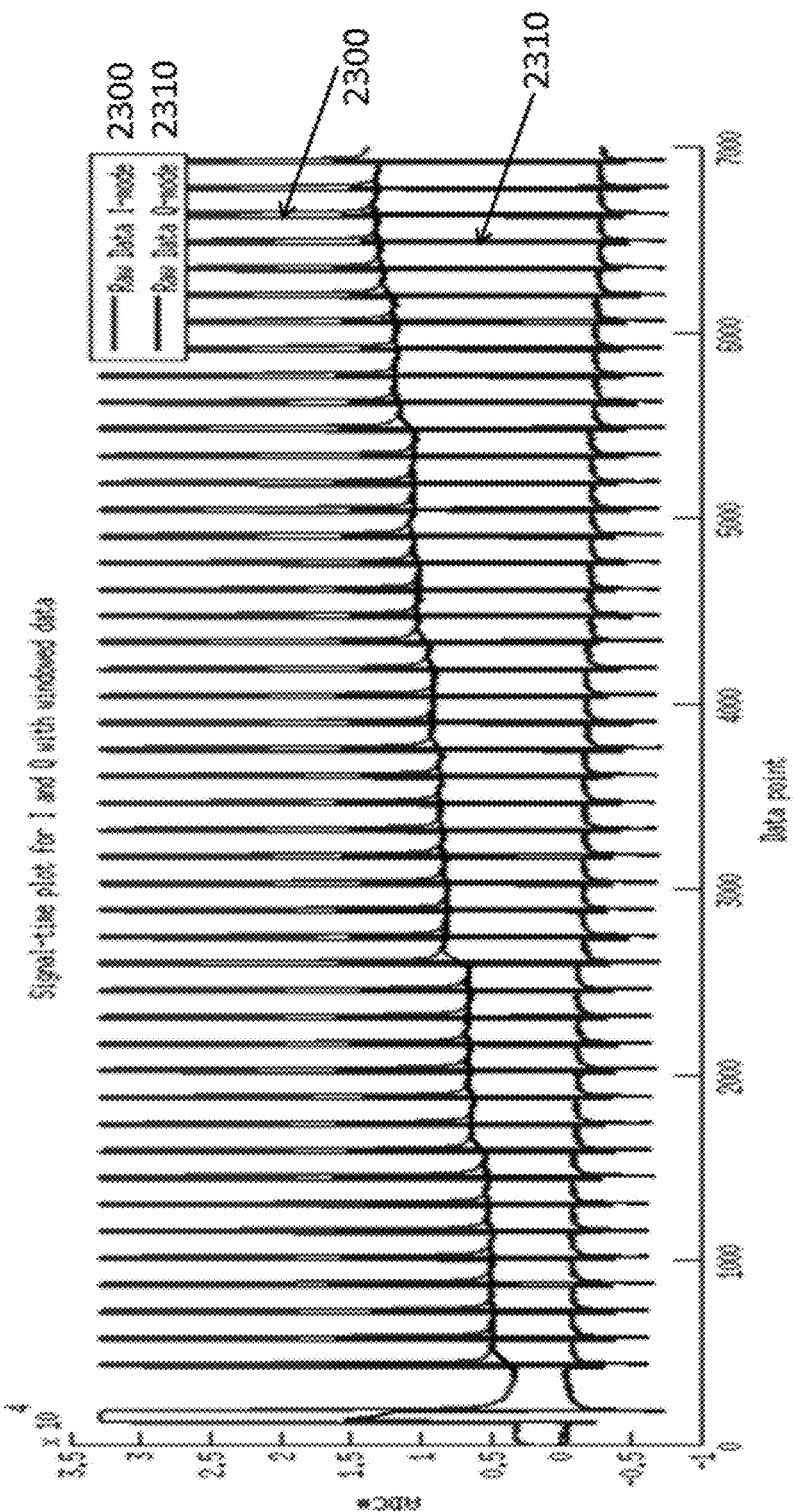
FIG. 23A graphically shows raw data derived from an example sensor, in I an Q mode.

A multi-phase measurement method described herein can be useful in making signal measurements at two independent phases (e.g., such as 0 and 90°). In this case, the signal can be expressed in terms of "I" and "Q" which are two perpendicular components of the actual signal, as is schematically shown in FIG. 22. For example, FIG. 23A shows raw data derived from operation of an example sensor in I and Q mode. The vertical axis ranges from $-1 \times 10^4$ to $3.5 \times 10^4$. The horizontal axis ranges from 0 to 7,000 data points. The data for I mode (2300) are shown overlaid with data for Q mode (2310).

Figure 23B:
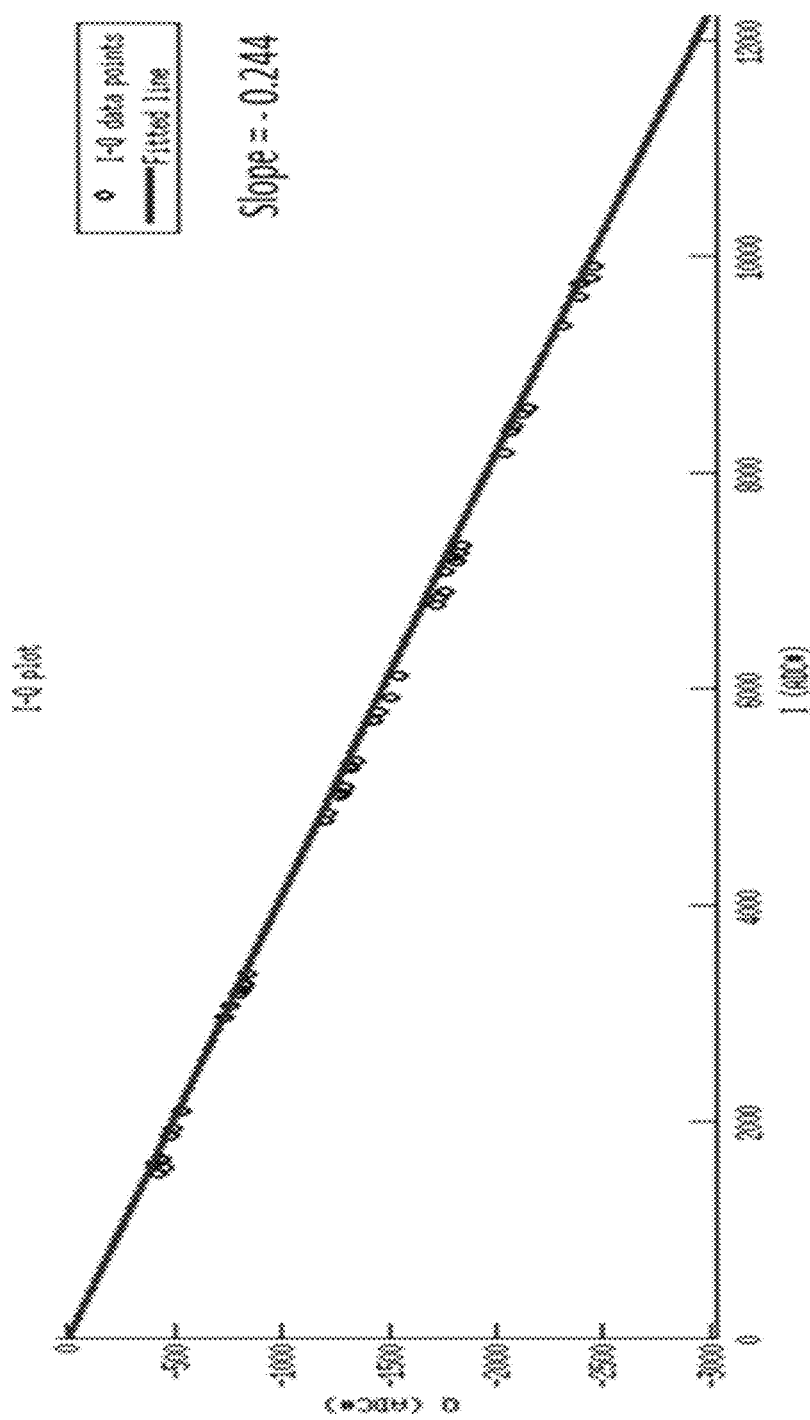
FIG. 23B graphically shows the line of action for measurements taken with an example sensor.

The sequencing data obtained from I and Q modes can show a linear relationship between I and Q modes, which linear relationship is referred to herein as a "line of action". A line of action can indicate a sequencing run can be completed at a single phase along the line of action. FIG. 23B graphically depicts an example of line of action for measurements taken with an example sensor. The parameter Q associated with Q mode is on the vertical axis ranging from −3000 to 0 ADC#. The parameter I associated with I mode is on the horizontal axis ranging from 0 to 12000 ADC#. As shown in FIG. 23B, the data has been fitted with a trend-line via linear regression, which trend-line has a slope of −0.244.

Figure 24:
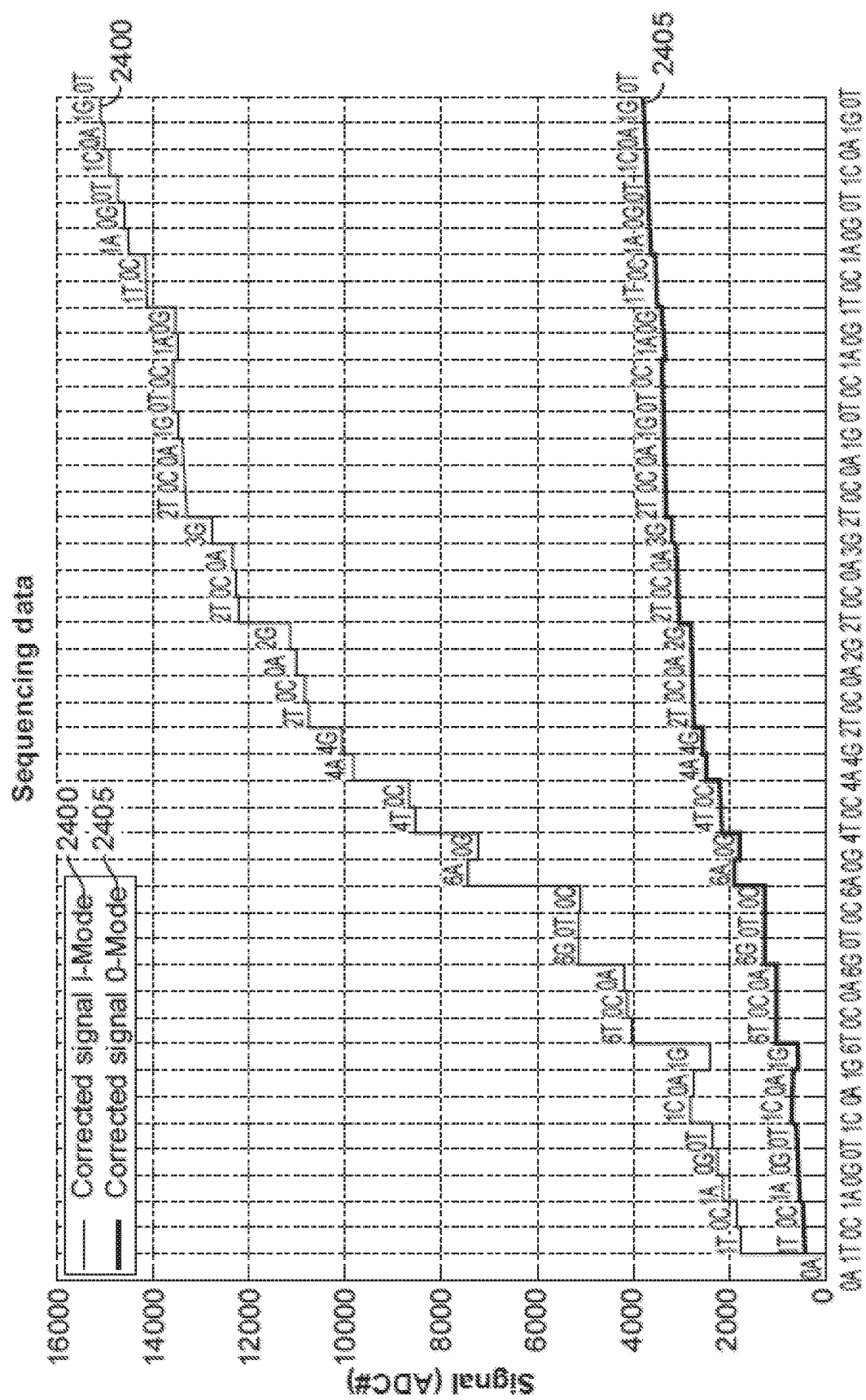
FIG. 24 graphically shows an example of sequencing data in I and Q modes.
Figure 25:
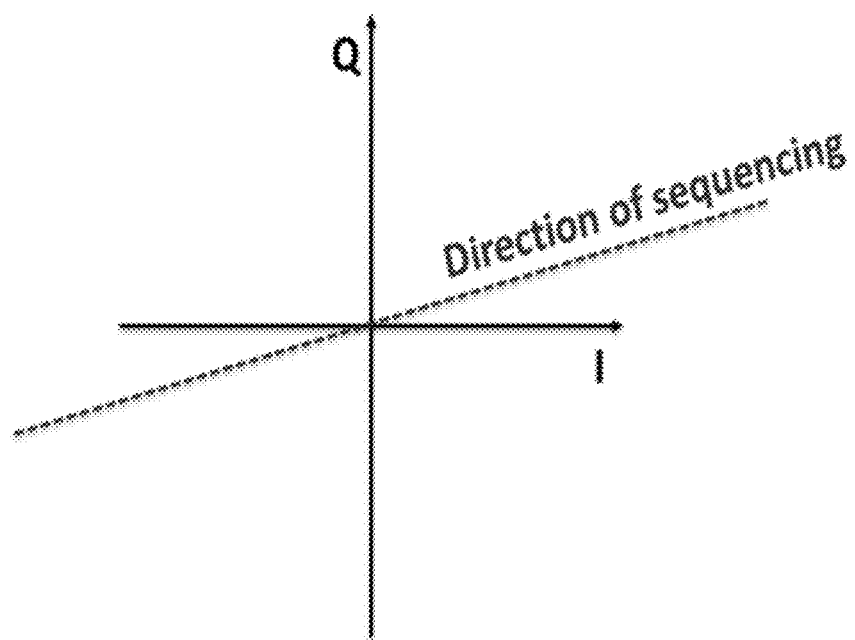
FIG. 25 graphically shows an example of sequencing using a single phase along a line of action.

Moreover, FIG. 24 graphically depicts another example of raw data obtained from an example sensor in I mode 2400 and Q mode 2405. FIG. 25 shows an additional example of sequencing using a single phase along a line of action. When performing a single measurement, it can be optimal to perform sequencing on the line of action, which in the example shown in FIG. 25, has an angle of about 20°.

Systems, devices and methods of the present disclosure may be combined with or modified by other systems, devices and methods, such as those described in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, PCT Patent Application No. PCT/US2015/020130 and PCT Patent Application No. PCT/US2015/026135, each of which is incorporated herein by reference in its entirety for all purposes.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for detecting a biological molecule, comprising:
   (a) activating a sensor comprising a circuit having at least two electrodes by applying at least two different voltage waveforms with different frequencies to said at least two electrodes, measuring one or more first signals associated with first impedances of said circuit, and deriving one or more first electrical parameters from said one or more first signals, wherein each of said first impedances is associated with one of said at least two different voltage waveforms;
   (b) bringing a solution comprising said biological molecule adjacent to said sensor under conditions sufficient to permit said biological molecule to couple to a support proximate to said at least two electrodes;
   (c) applying said at least two different voltage waveforms to said circuit having said at least two electrodes, measuring one or more second signals associated with second impedances of said circuit, and deriving one or more second electrical parameters from said one or more second signals, wherein each of said second impedances is associated with one of said at least two different voltage waveforms; and
   (d) comparing at least one of said one or more first electrical parameters with at least one of said one or more second electrical parameters to detect a presence of said biological molecule.

2. The method of claim 1, wherein said biological molecule comprises a nucleotide base, a nucleic acid, a protein or a peptide.

3. The method of claim 1, wherein said biological molecule is coupled to said support through a linker molecule.

4. The method of claim 1, wherein said support is a bead.

5. The method of claim 1, wherein said at least two different voltage waveforms comprise frequencies along a continuous frequency sweep.

6. The method of claim 1, wherein said first signals or said second signals comprise a first current and a second current each associated with one of said at least two different voltage waveforms.

7. The method of claim 6, further comprising deriving said first impedances or said second impedances from said first current and said second current.

8. The method of claim 1, wherein one or more of said at least two electrodes is positioned within a Debye layer comprising said support, and wherein said first impedances or said second impedances are associated with said Debye layer.

9. The method of claim 1, wherein in (b), said at least two electrodes are exposed to said solution.

10. The method of claim 1, wherein said biological molecule comprises a nucleotide base, and wherein said biological molecule is a component of a nucleic acid sequencing reaction.

11. The method of claim 1, wherein at least one of said at least two different voltage waveforms comprises a square wave.

12. The method of claim 1, wherein said one or more first electrical parameters or said one or more second electrical parameters comprise one or more members selected from the group consisting of: (i) a resistance associated with a support proximate to at least one of said at least two electrodes; (ii) a fluid capacitance associated with a fluid proximate to said at least two electrodes; and (iii) an electrode capacitance associated with one or more of said at least two electrodes.

13. The method of claim 1, wherein said at least two electrodes comprise a transmitter electrode and a receiver electrode, and wherein said first signals and said second signals are generated using an electrical flow path directed from said transmitter electrode to said receiver electrode.

14. The method of claim 13, wherein prior to (a) said transmitter electrode and said receiver electrode are electrically isolated, and wherein activating said sensor in (a) comprises forming said electrical flow path.

15. The method of claim 1, wherein the one or more second electrical parameters comprise a combined resistance associated with said support and said biological molecule.

16. The method of claim 1, wherein at least one of said at least two different voltage waveforms comprises multiple frequencies, multiple phases, or a combination thereof.

17. The method of claim 1, wherein said at least two different voltage waveforms comprise frequencies in a range of about 100 kilohertz to 1 megahertz.

18. The method of claim 1, wherein deriving one or more first electrical parameters from said one or more first signals comprises solving a system of equations to calculate a first admittance of said circuit using said one or more first signals, and wherein deriving one or more second electrical parameters from said one or more second signals comprises solving said system of equations to calculate a second admittance of said circuit using said one or more second signals.

* * * * *